US012399124B2

(12) United States Patent
Preira et al.

(10) Patent No.: US 12,399,124 B2
(45) Date of Patent: Aug. 26, 2025

(54) ULTRA-SENSITIVE DETECTION METHOD USING PHOTOLUMINESCENT PARTICLES

(71) Applicants: ECOLE POLYTECHNIQUE, Palaiseau (FR); CENTRE NATIONAL DE LA RECHERCHE SCIENTIFIQUE, Paris (FR)

(72) Inventors: Pascal Preira, Savigny-sur-Orge (FR); Maximilian Richly, Paris (FR); Cédric Bouzigues, Paris (FR); Antigoni Alexandrou, Palaiseau (FR); Thierry Gacoin, Bures-sur-Yvette (FR)

(73) Assignees: ECOLE POLYTECHNIQUE, Palaiseau (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 1130 days.

(21) Appl. No.: 16/635,515

(22) PCT Filed: Aug. 3, 2018

(86) PCT No.: PCT/EP2018/071194
§ 371 (c)(1),
(2) Date: Jan. 30, 2020

(87) PCT Pub. No.: WO2019/025618
PCT Pub. Date: Feb. 7, 2019

(65) Prior Publication Data
US 2020/0271586 A1     Aug. 27, 2020

(30) Foreign Application Priority Data

Aug. 4, 2017   (FR) ..................... 1757554

(51) Int. Cl.
| | | |
|---|---|---|
| *G01N 21/64* | (2006.01) | |
| *A61K 49/00* | (2006.01) | |
| *A61K 49/10* | (2006.01) | |
| *C09K 11/02* | (2006.01) | |
| *G01N 33/58* | (2006.01) | |
| *C01F 1/00* | (2006.01) | |
| *G01N 33/543* | (2006.01) | |

(52) U.S. Cl.
CPC ..... *G01N 21/6486* (2013.01); *A61K 49/0065* (2013.01); *A61K 49/105* (2013.01); *C09K 11/025* (2013.01); *G01N 21/6402* (2013.01); *G01N 21/6428* (2013.01); *G01N 33/582* (2013.01); *C01F 1/00* (2013.01); *G01N 2021/6439* (2013.01); *G01N 33/54346* (2013.01); *G01N 2458/40* (2013.01); *Y10S 977/92* (2013.01); *Y10S 977/957* (2013.01); *Y10S 977/958* (2013.01)

(58) Field of Classification Search
None
See application file for complete search history.

(56) References Cited

U.S. PATENT DOCUMENTS

| | | | |
|---|---|---|---|
| 2009/0079978 A1 | 3/2009 | Kimura | |
| 2009/0159812 A1* | 6/2009 | Livingston | ......... G01N 21/6428 |
| | | | 250/428 |
| 2010/0009458 A1 | 1/2010 | Ohtsuka | |
| 2011/0065209 A1* | 3/2011 | Heil | ................. G01N 33/54326 |
| | | | 422/69 |
| 2015/0010476 A1 | 1/2015 | Schoeffel et al. | |

FOREIGN PATENT DOCUMENTS

WO         2013132197 A1    9/2013

OTHER PUBLICATIONS

Schoeffel, M., et al., "Multifunctional Rare Earth Vanadate Nanoparticles: Luminescent Labels, Oxidant Sensors and Magnetic Resonance Imaging Contrast Agents", Ecole Polytechnique Thesis, pp. 1-244 (Year: 2012).*
Casanova, D., et al., "Optical in situ size determination of single lanthanide-ion doped oxide nanoparticles", Appl. Phys. Lett., pp. 253103-1 through 253103-3 (Year: 2006).*
Giaume, D., et al., "Functionalized Luminescent Oxide Nanoparticles as Biological Probes", Mater. Res. Soc. Symp. Proc., pp. 1-7 (Year: 2006).*
CN Office Action in Application No. 201880061006.6 Dated Aug. 3, 2022.
Abdesselem et al. "Multifunctional Rare-Earth Vanadate Nanoparticles: Luminescent Labels, Oxidant Sensors, and MRI Contrast Agents" ACS Nano, Vo. 8, No. 11, 11126-11137; Oct. 20, 2014.
Beaurepaire et al. "Functionalized Fluorescent Oxide Nanoparticles: Artificial Toxins for Sodium Channel Targeting and Imaging at the Single-Molecule Level" Nano Letters 2004, 4, 11, 2079-2083; Publication Date: Oct. 26, 2004.
Bouzigues et al. "Biological Applications of Rare-Earth Based Nanoparticles" ACS Nano 2011, 5, 11, 8488-8505 Publication Date: Oct. 8, 2011.
Roberto de la Rica et al. "Plasmonic ELISA for the ultrasensitive detection of disease biomarkers with the naked eye" Nature Nanotechnology vol. 7, pp. 821-824; Oct. 28, 2012.

(Continued)

*Primary Examiner* — Jake M Vu
(74) *Attorney, Agent, or Firm* — Maschoff Brennan

(57) ABSTRACT

A process for ultrasensitive in vitro detection and/or quantification of a substance of interest in a sample is performed by detecting the luminescence emission by photoluminescent inorganic nanoparticles. The process includes (i) use of photoluminescent particles comprising a photoluminescent inorganic nanoparticle consisting of a crystalline matrix having at least $10^3$ rare-earth ions, and coupled to a targeting agent for the substance to be analyzed, under conditions conducive to their association with the sample substance to be analyzed; (ii) exciting the rare-earth ions of the particles by an illumination device having a power of at least 50 mW and an excitation intensity of at least 1 $W/cm^2$; (iii) detecting the luminescence emission by the particles after single-photon absorption; and (iv) determining the presence and/or concentration of the substance by interpreting said luminescence measurement. This process can be used for in vitro diagnostic purposes and as an in vitro diagnostic kit.

27 Claims, 17 Drawing Sheets

(56) References Cited

OTHER PUBLICATIONS

Figure 1:
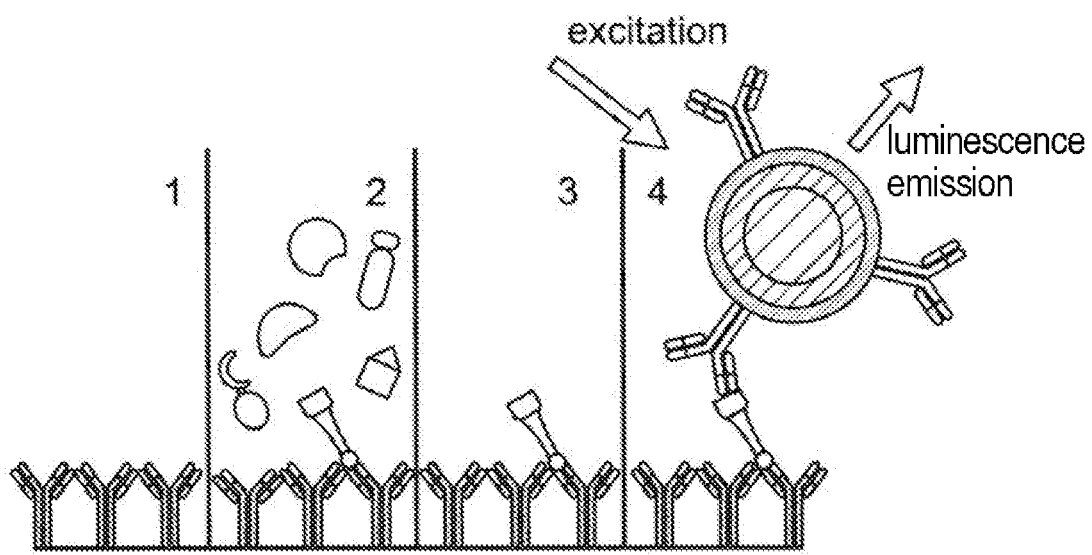

V. Dordevic et al. "The concentration quenching of photoluminescence in Eu3+-doped La2O3" Journal of Research in Physics, vol. 37, No. 1, 47-54; Dec. 24, 2013.
Dosev et al. "Application of luminescent Eu:Gd2O3 nanoparticles to the visualization of protein micropatterns" Journal of Biomedical Optics 10(6), 064006 (Nov./Dec. 2005).
Giljohann et al. "Gold Nanoparticles for Biology and Medicine" Angew Chem Int Ed Engl. 49(19):3280-94. Apr. 26, 2010.
Yi et al. "Synthesis, Characterization, and Biological Application of Size-Controlled Nanocrystalline NaYF4:Yb,Er Infrared-to-Visible Up-Conversion Phosphors" Nano Letters 2004, 4, 11, 2191-2196; Publication Date: Oct. 16, 2004.
Howes et al. "Colloidal nanoparticles as advanced biological sensors" Science; 346(6205):1247390. doi: 10.1126/science.1247390. Oct. 3, 2014.
Huignard et al. "Synthesis and Luminescence Properties of Colloidal YVO4:Eu Phosphor" hem. Mater. 12, 4, 1090-1094; Publication Date:Mar. 29, 2000.
Medintz et al. "Quantum dot bioconjugates for imaging, labelling and sensing" Nature Materials vol. 4, pp. 435-446; Published Jun. 1, 2005.
Meza et al. "Luminescence Concentration Quenching Mechanism in Gd2O3:Eu3+" J. Phys. Chem. A 2014, 118, 8, 1390-1396; Publication Date: Feb. 11, 2014.
Nam et al. "Nanoparticle-Based Bio-Bar Codes for the Ultrasensitive Detection of Proteins" Science.; 301(5641):1884-6. Sep. 26, 2003.
K. Riwotzki et al. "Wet-Chemical Synthesis of Doped Colloidal Nanoparticles: YVO4:Ln (Ln ) Eu, Sm, Dy)" J. Phys. Chem. B 1998, 102, 10129-10135; Publication date: Nov. 14, 1998.
Türkcan et al. "Observing the Confinement Potential of Bacterial Pore-Forming Toxin Receptors Inside Rafts with Nonblinking Eu3D-Doped Oxide Nanoparticles" Biophys J.; 102(10):2299-308. May 15, 2012.
Yuan et al. "Lanthanide-based luminescence probes and time-resolved luminescence bioassays" Trends in Analytical Chemistry, vol. 25, No. 5, May 2006.
Nan Wang et al. "Influence of metal oxide nanoparticles concentration on their zeta potential" J Colloid Interface Sci. Oct. 1, 2013;407:22-8. doi: 10.1016/j.jcis.2013.05.058. Jun. 20, 2013.
Giaume et al. "Functionalized Luminescent Oxide Nanparticles as Biological Probes" Mrs Proceedings, vol. 942, Jan. 1, 2006.
Drozdowicz-Tomsi et al. "Europium and Samarium doped Ga2O3 Nanoparticles as Potential New Fluorescent Labels" Nanoscience and Nanotechnology, 2006. ICONN '06. Jul. 3, 2006.
H. Li et al. "Simultaneous detection of two lung cancer biomarkers using dual-color fluorescence quantum dots" Analyst, 2011, 136, pp. 1399-1405 ; Jan. 10, 2011.
Geissler et al., "Quantum Dot Biosensors for Ultrasensitive Multiplexed Diagnostics" Angew. Chem. Int. Ed.2010,49, 1396-1401; Feb. 9, 2010.
Zhu et al. "Ultrasensitive and Selective Electrochemical Diagnosis of Breast Cancer Based on a Hydrazine—Au Nanoparticle—Aptamer Bioconjugate" Anal. Chem. 2013, 85, 2, 1058-1064; Publication Date:Dec. 5, 2012.
Cordeiro et al. "Gold Nanoparticles for Diagnostics: Advances towards Points of Care" Diagnostics (Basel). 2016;6(4):43. Published Nov. 22, 2016.
Riwotzki et al. "Colloidal YVO4:Eu and YP0.95V0.05O4:Eu Nanoparticles: Luminescence and Energy Transfer Processes" J. Phys. Chem. B 2001, 105, 51, 12709-12713; Publication Date: Dec. 1, 2001.
Tang et al. "Detection of Anthrax Toxin by an Ultrasensitive Immunoassay Using Europium Nanoparticles" Clin Vaccine Immunol, 2009, 16(3), pp. 408-413; Mar. 2009.
Härmä et al. "Europium Nanoparticles and Time-resolved Fluorescence for Ultrasensitive Detection of Prostate-specific Antigen" Clinical Chemistry 47:3; 561-568; Mar. 2001.
Corstjens et al. "A user-friendly, highly sensitive assay to detect the IFN-γ secretion by T cells" Clinical Biochemistry; vol. 41, Issue 6, Apr. 2008, pp. 440-444.
Jiang et al. "Preparation and Time-Resolved Luminescence Bioassay Application of Multicolor Luminescent Lanthanide Nanoparticles" Journal of Fluorescence; Jan. 2010, vol. 20, Issue 1, pp. 321-328.
Tanja et al. "Detection strategies for bioassays based on luminescent lanthanide complexes and signal amplification" Analytical and Bioanalytical Chemistry; Sep. 1, 2004, vol. 380, Issue 1, pp. 24-30.
Zhou et al. "Dissolution-Enhanced Luminescent Bioassay Based on Inorganic Lanthanide Nanoparticles" Angewandte Chimie, Aug. 11, 2014, 126(46), pp. 12706-12710.
Casanova et al. "Counting the Number of Proteins Coupled to Single Nanoparticles" J. Am. Chem. Soc. 2007, 129, 42, 12592-12593; Publication Date:Sep. 29, 2007.
Giaume et al. "Organic Functionalization of Luminescent Oxide Nanoparticles toward Their Application As Biological Probes" Langmuir 2008, 24, 19, 11018-11026; Publication Date:Sep. 5, 2008.
Casanova et al. "Optical in situ size determination of single lanthanide-ion doped oxide nanoparticles" Appl. Phys. Lett. 89, 253103; Published Dec. 18, 2006.
Son et al. "Luminescent Lanthanide Nanoparticles as Labels in DNA Microarrays for Quantification of Methyl Tertiary Butyl Ether Degrading Bacteria" Journal of Nanoscience and Nanotechnology, vol. 8, No. 5, May 2008, pp. 2463-2467(5).
Nichkova et al. "Microarray Immunoassay for Phenoxybenzoic Acid Using Polymer Encapsulated Eu:Gd2O3 Nanoparticles as Fluorescent Labels" Anal. Chem. 2005, 77, 21, 6864-6873; Publication Date: Sep. 23, 2005.
Pisanic et al. "Quantum dots in diagnostics and detection: principles and paradigms" Analyst. Jun. 2, 20141;139(12):2968-81. Apr. 28, 2014.
Hemmilä, I. et al., "Europium as a label in time-resolved immunofluorometric assays," Analytical Biochemistry, vol. 137, Issue 2, pp. 335-343 (Mar. 1984).
Cao, Z. et al., "Cross-talk-free simultaneous fluoroimmunoassay of two biomarkers based on dual-color quantum dots," Analytica Chimica Acta, vol. 698 , Issue 1-2 , pp. 44-50 (2011).

* cited by examiner

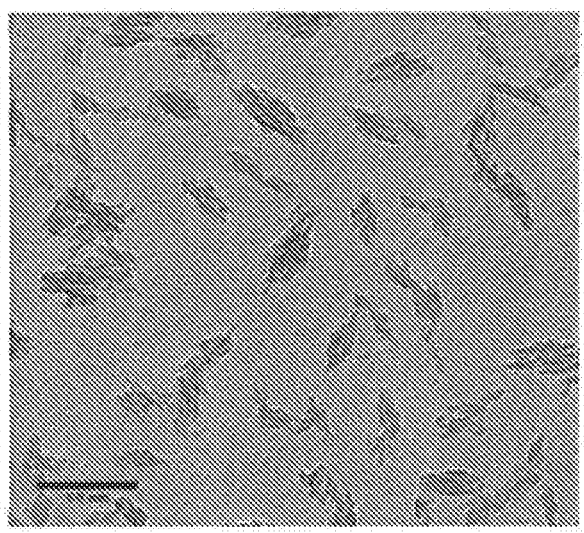
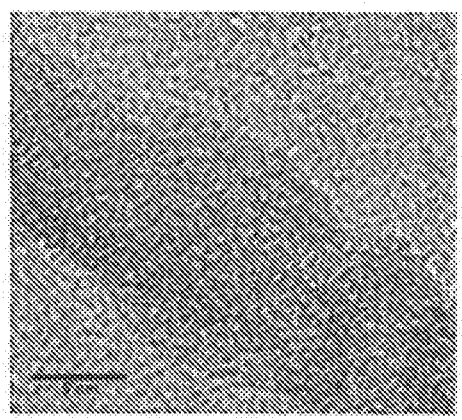
Fig. 3a  Fig. 3b
Fig. 3
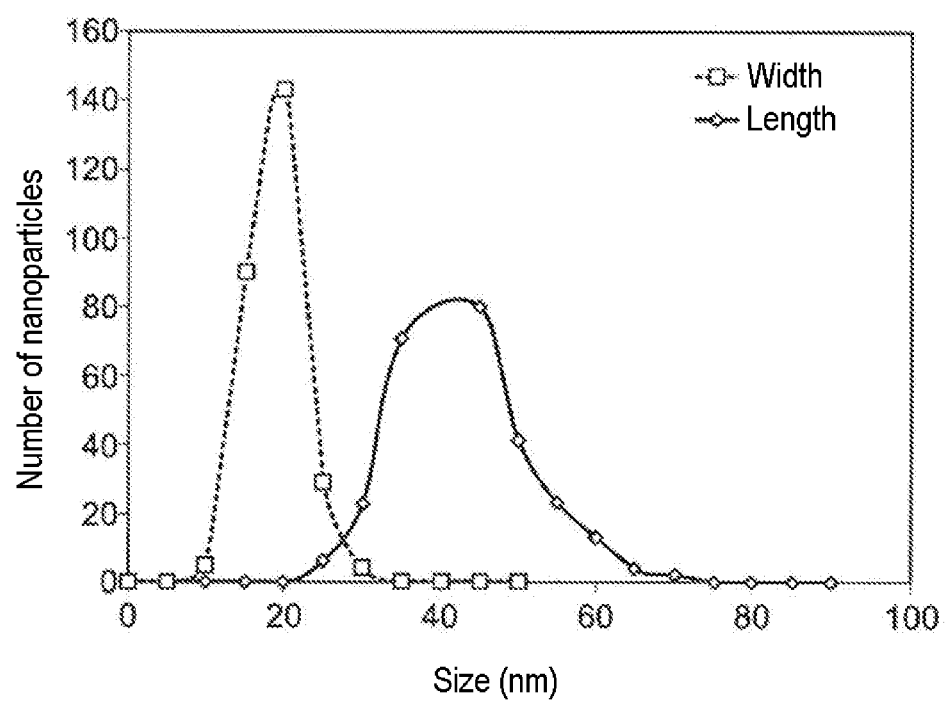
Fig. 4

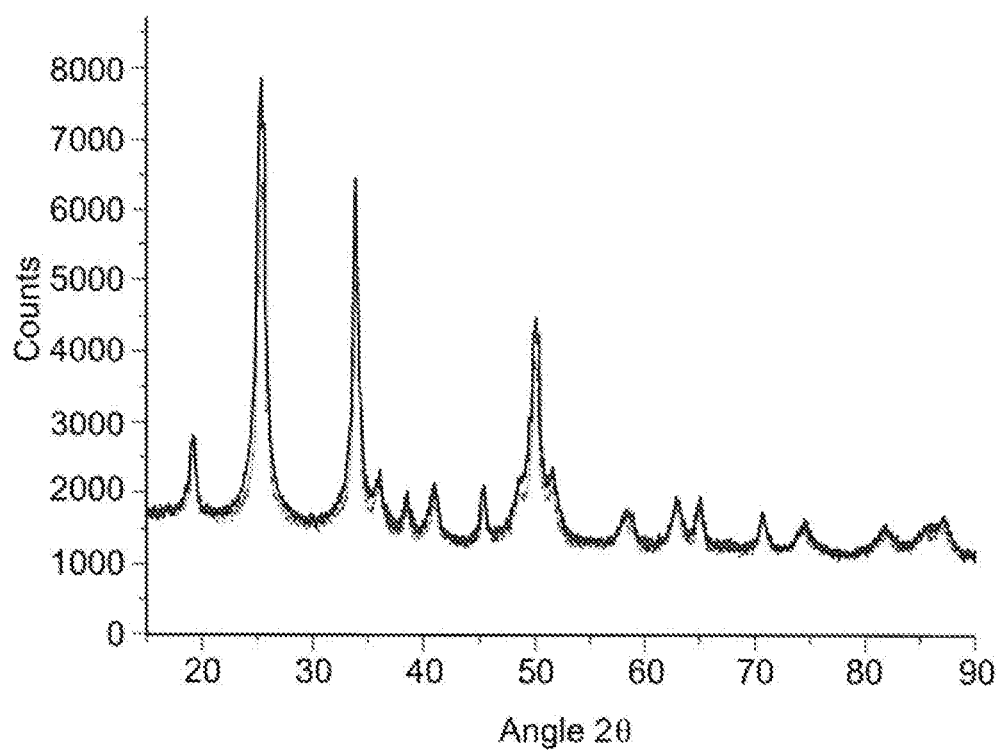
Fig. 5
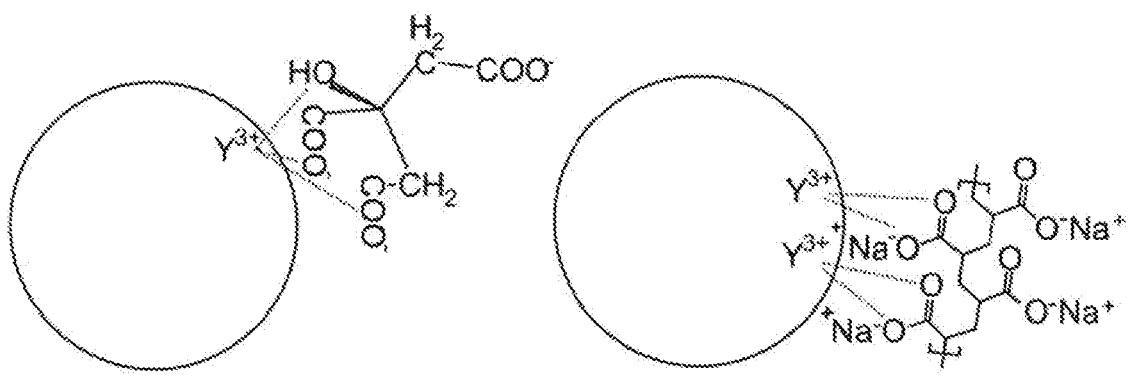
Fig. 6a        Fig. 6b
Fig. 6

Figure 10A:
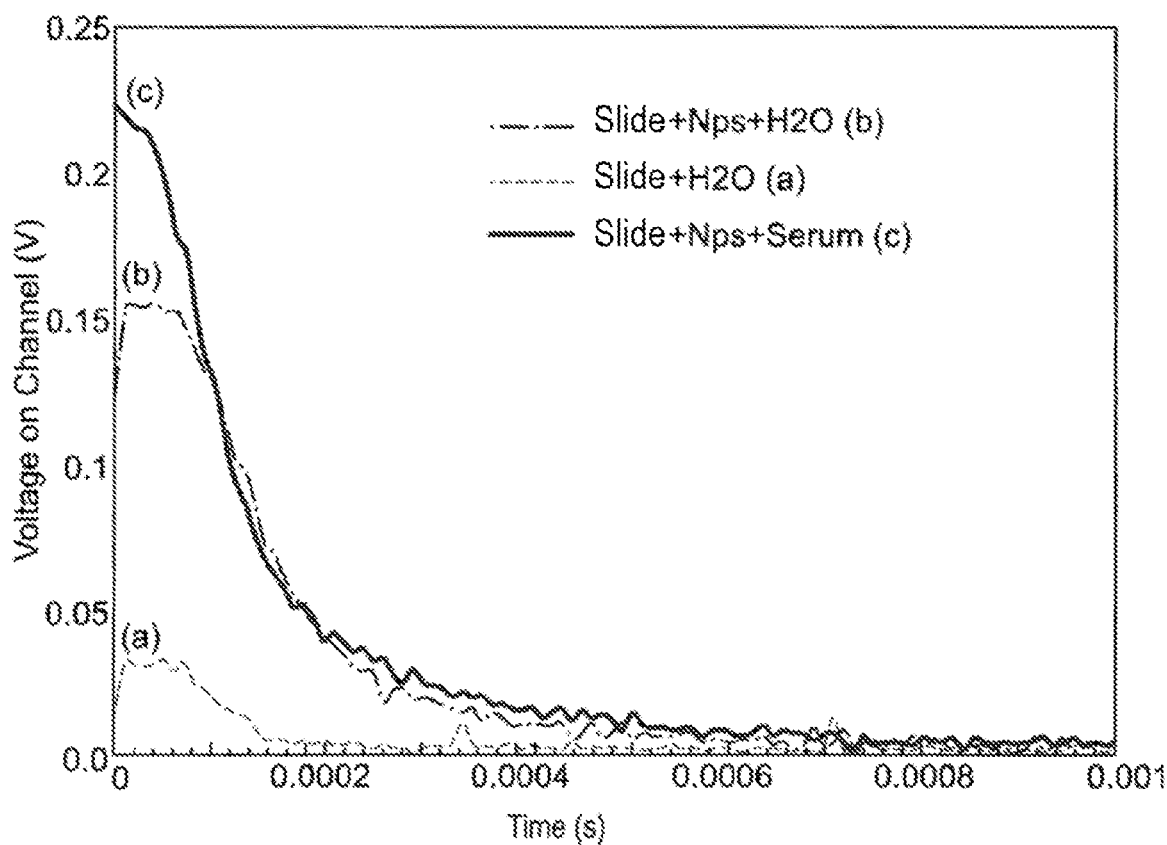

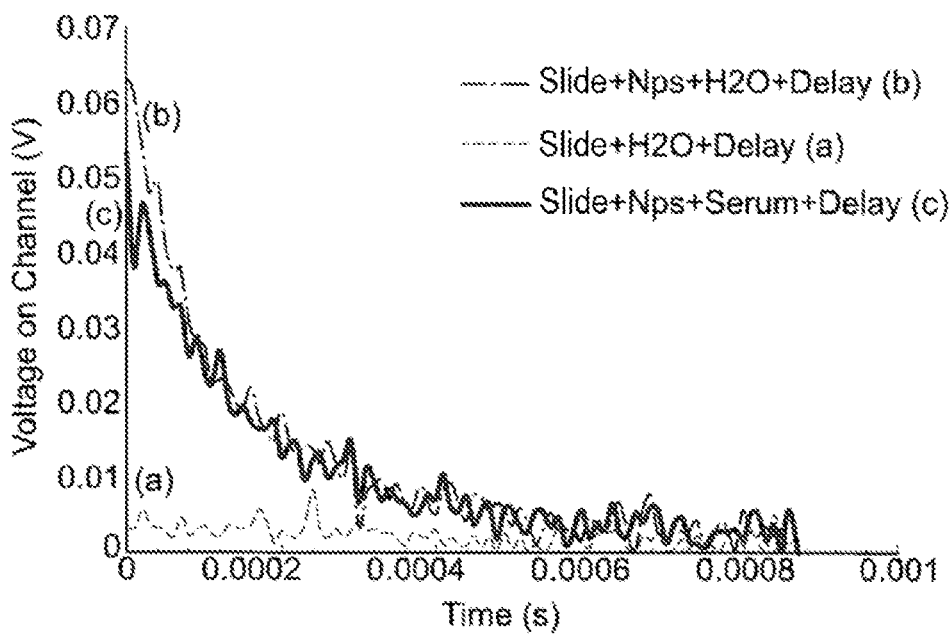
Fig. 10b
Fig. 10
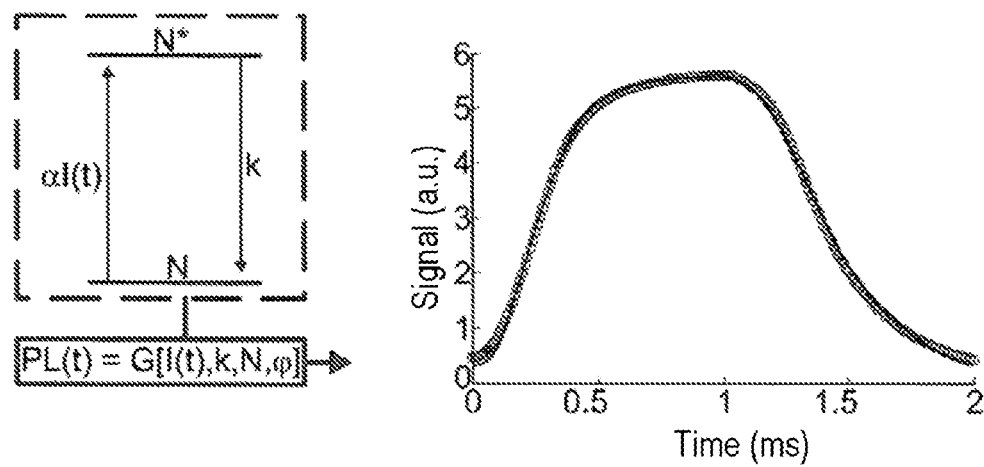
Fig. 11

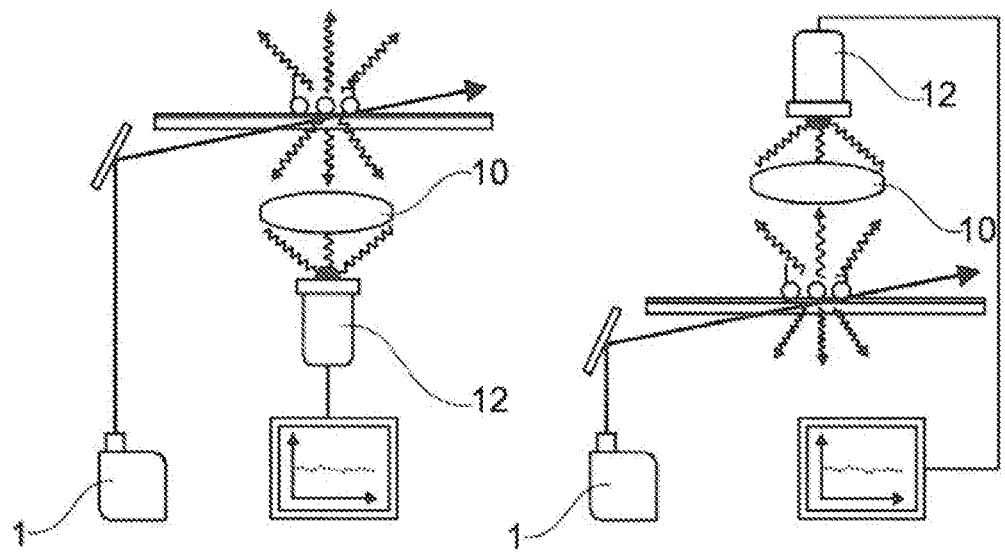
Fig. 12-a  Fig. 12  Fig. 12-b
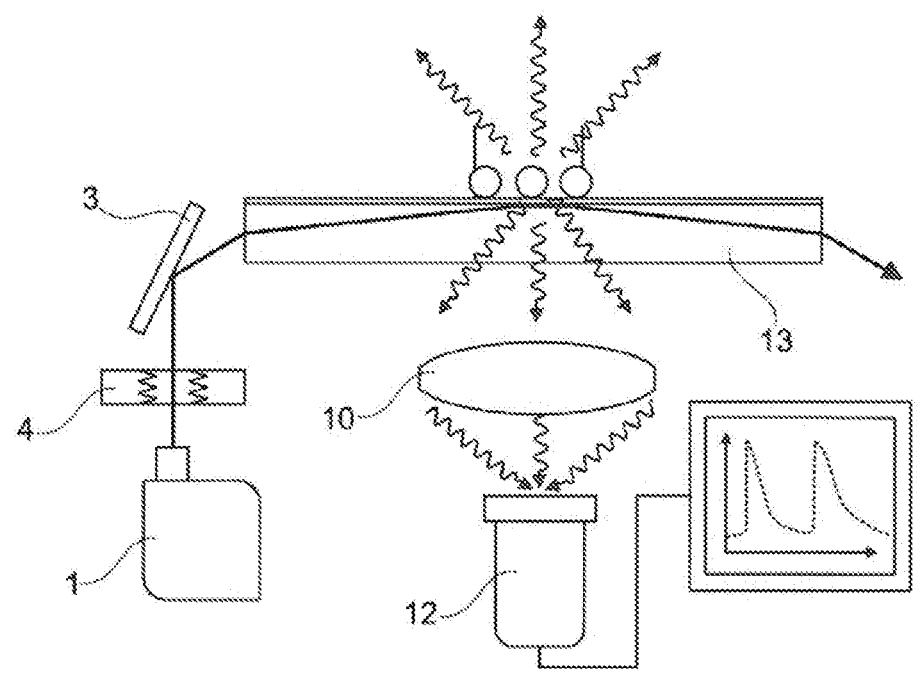
Fig. 13

ULTRA-SENSITIVE DETECTION METHOD USING PHOTOLUMINESCENT PARTICLES

The present invention relates to the field of research, bioanalysis and in vitro diagnostics. More particularly, its subject matter is a process for the ultrasensitive in vitro detection and/or quantification of substances of biological or chemical interest, for example biomarkers, antibodies, DNA, RNA and other compounds, in a sample, in particular a biological sample, by detection of the luminescence emission by photoluminescent inorganic nanoparticles with controlled optical and physicochemical properties.

The detection and/or quantification of concentrations of biomarkers, antibodies or DNA and RNA in biological samples (blood, serum, saliva, urine, cerebrospinal fluid, etc.) are essential for medical diagnosis.

In the field of research, in vitro or ex vivo diagnostics, medical analysis and bioanalysis, a number of methods have been proposed to detect and/or determine the presence of specific substances.

These methods are generally based on the use of a probe employed to detect and/or quantify a concentration in solution. These probes are coupled to a recognition compound, or targeting agent, to bind to the molecular species to be analyzed. This recognition compound can be a molecule, DNA, aptamer, protein or antibody. Then, the probes that have attached to the molecular species to be analyzed thanks to the recognition compound can be detected using one or more methods based, for example, on their luminescence, absorbance, chemical reactivity, radioactivity, etc.

The most commonly used biochemical assays are enzyme-linked immunosorbent assays (ELISA), which generally rely on the use of horseradish peroxidase as an enzyme to cause a reaction with a substrate and to quantify the chemical reaction taking place by measuring the absorbance of the reaction product in solution. The choice of the molecular recognition compound to which the probe is coupled is critical to the effectiveness of these probes. More precisely, the effectiveness of these methods depends on the specific affinity of the recognition compound with the target substance. As examples, the referenced publications [1] and [2] detail the features of these mechanisms.

Luminescent probes generally lead to a more sensitive detection than probes detected by their absorbance because, in the first case, measurements of light intensity are made against a dark background, whereas, in the second case, it is a matter of measuring a variation in light intensity (brightfield measurements).

Other assay methods currently available include electrochemiluminescence (ECLIA), fluorescence immunoassay (FIA) and radioimmunoassay (RIA).

However, these methods have various drawbacks that limit their final detection sensitivity, in particular limitations in terms of the luminescence properties of the probes used (ECLIA, FIA), safety risks, expensive equipment and the need for specialized users (not automated machines) to conduct RIA-type tests.

In particular, currently available luminescent probes have several disadvantages that do not allow their full potential as diagnostic sensors to be exploited. These drawbacks include, for example, the phenomenon of photobleaching in the case of organic fluorophores which, following irreversible structural changes induced by illumination, results in a disappearance of fluorescence, or the phenomenon of emission flickering in the case of semiconductor nanocrystals, or "quantum dots", in which case the probes periodically cease to emit and are therefore unsuitable for producing a constant signal. Other disadvantages result, for example, from the wide emission spectrum of luminescent probes. In fact, too wide an emission spectrum makes it difficult to filter out any background signal that may be present, and affects the quality of the signal and, in particular, the signal-to-noise ratio. In addition to the optical factors that contribute to the effectiveness of the probe in a bioassay, the practicality and ease of use of the probe should also be considered. For example, some particles, such as semiconductor nanocrystals, lose their luminescence characteristics after freezing, which is a disadvantage for the storage of bioconjugates. The ease of coupling the probes to the molecular compound to target the desired molecules is also an aspect to consider when choosing the right probe. For example, a number of particles, including semiconductor nanocrystals, are synthesized in organic solvents. As a result, use for biological applications requires additional surface preparation steps to achieve dispersion of these particles in water, a process that can be complex to implement and not very stable over time [3].

Furthermore, the colloidal properties of the particles/probes are critical to the conduct of bioassays. In fact, solutions with good colloidal stability are able to provide media of good homogeneity for the tests, and therefore better reproducibility of the test results.

Finally, complexity and cost are important aspects in the choice of diagnostic probes. For example, gold nanoparticles, and their properties in terms of surface plasmon resonance, have been proposed as diagnostic probes, but have not made inroads as probes for in vitro diagnosis, possibly because of the complexity of the detection method [4], or possibly high cost. Semiconductor crystals, in turn, are synthesized in organic solvents and require dispersion procedures in an aqueous medium, which makes their synthesis complex and therefore expensive. Their functionalization with chemical groups, allowing coupling to the molecular recognition compounds of the target molecules, also relies on weak chemical bonds, which therefore limits their stability and is detrimental to the reproducibility of detection tests.

Moreover, the in vitro detection methods currently available are not fully satisfactory, particularly in terms of the detection sensitivity that can be achieved, in order to broaden the scope of in vitro diagnostic methods, for example by allowing earlier detection of diseases or by allowing a diagnosis on the evolution of a disease or the effect of a therapeutic treatment.

To improve detection sensitivity, two commercial ultrasensitive immunoassay techniques have been developed. These are the methods developed by Quanterix and Singulex. They are based on the use of functionalized magnetic beads as reactive surfaces for the capture of target molecules. Quanterix technology then captures the individual beads functionalized with antibodies to the antigens. Each bead is trapped in a well and analyzed by standard ELISA. Singulex, in turn, uses the beads to concentrate the trapped analytes and then determines their concentration by counting the fluorescent signals using a confocal detection device and an excitation laser that scans the sample helically.

These two techniques, although they achieve higher performance in terms of detection sensitivity than the conventional detection technologies discussed above, are nevertheless highly complex and expensive. They require the use of equipment specifically dedicated to these detection techniques, which is not compatible with current automated in vitro diagnostic devices.

Semiconductor nanocrystals or "quantum dots" have also been proposed in ultrasensitive detection tests ([5], [6], [7], [8] and [9]). However, the effectiveness of these tests is limited by the drawbacks associated with this type of luminescent probe, as discussed above: complexity and high cost of their synthesis and functionalization, unsatisfactory colloidal stability, loss of luminescence properties after freezing.

Finally, methods based on the use of gold nanoparticles by exploiting phenomena such as the detection of surface plasmons, fluorescence quenching, silver deposition on gold nanoparticles, etc. ([9] to [13]), achieve high detection sensitivities but are generally highly complex.

Therefore, there remains a need to develop a detection/quantification method that achieves higher performance in terms of detection sensitivity than conventional technologies such as ELISA, ECLIA, FIA or RIA and does not have the drawbacks, particularly in terms of complexity and cost, of the ultrasensitive methods already proposed.

The present invention aims precisely at proposing a novel ultrasensitive detection method, based on the use of luminescent nanoparticles doped with rare-earth ions with controlled optical and physicochemical properties.

Thus, the invention, according to a first of its aspects, concerns a process for the ultrasensitive in vitro detection and/or quantification of a substance of biological or chemical interest in a sample, in particular a biological sample, by detecting the luminescence emission by photoluminescent inorganic nanoparticles, comprising at least the following steps:

(i) use of photoluminescent particles consisting, in whole or in part, of a photoluminescent inorganic nanoparticle consisting of a crystalline matrix having at least $10^3$ rare-earth ions, and coupled to at least one targeting agent for the substance to be analyzed, under conditions conducive to their association with the substance to be analyzed of the sample, said nanoparticles having an average size greater than or equal to 20 nm and strictly less than 1 μm, in particular between 20 nm and 500 nm, preferably between 20 nm and 200 nm and notably between 20 nm and 100 nm, and being capable of emitting luminescence after absorption of a photon;

(ii) excitation of the rare-earth ions of the particles associated with the substance to be analyzed by an illumination device, in particular of the laser type, with a power of at least 50 mW, preferably at least 500 mW, and an excitation intensity of at least 1 W/cm$^2$, preferably at least 10 W/cm$^2$;

(iii) detection of the luminescence emission by the particles, and (iv) determination of the presence and/or concentration of the substance by interpretation of said luminescence measurement, where appropriate by reference to a standard or calibration.

In the sense of the invention, the "analysis" of the substance in a sample covers the aspect of detection or qualitative characterization of the presence or absence of said substance, and also the aspect of determination or quantitative characterization of said substance.

The sample may be a biological specimen, in particular a human specimen, for example selected from blood, serum, plasma, saliva, urine and cerebrospinal fluid. The sample may also be diluted feces, vaginal or nasal swab or sputum.

A diluent may be used with the sample to be tested, especially when the liquid sample is plasma, serum, whole blood, nasal or vaginal smear or sputum, for example.

It may also be a solution containing biological molecules.

The process of the invention can thus be implemented for the detection and/or quantification of biomarkers, antibodies, DNA and/or RNA in a biological sample.

The process of the invention more particularly implements, in step (iii), the detection of luminescence by the particles after one-photon absorption.

According to the process of the invention, the detected signal thus corresponds to the luminescence emission by the photoluminescent nanoparticles after absorption of a single photon, in other words the emission at a wavelength longer than the excitation wavelength. The photoluminescent nanoparticles according to the invention are thus distinct from upconversion phosphor particles for which the detection of the luminescence emission is carried out after a two-photon absorption.

The ultrasensitive method according to the invention is advantageous in several ways.

First, as illustrated in the examples, the method of the invention achieves a performance in terms of detection sensitivity that is significantly higher than the performance of conventional ELISA, ECLIA, FIA or RIA type detection techniques.

Advantageously, the ultrasensitive method of the invention thus allows a detection at least 10 times, in particular at least 100 times, more sensitive than the ELISA type enzymatic immunodetection method using the same recognition and targeting antibodies.

The ultrasensitive method according to the invention thus allows detection and/or quantification of a substance of interest present in a sample in a content strictly below 10 pM, or even below 1 pM, or even below 0.1 pM, or even below 0.01 pM (10 fM). These concentrations depend on the target molecule and, in particular, on the affinity of the recognition compound, or targeting compound, coupled to the probe, but are comparable to those detectable by ultrasensitive methods (Quanterix or Singulex).

Moreover, the method of the invention is based on the use of nanoparticles doped with rare-earth ions, for example nanoparticles of formula $(A_{1-x}Ln_x)_a(M_pO_q)$ (I) as defined more precisely hereinbelow, such as nanoparticles of the type YVO$_4$:Eu or GdVO$_4$:Eu, YAG:Ce, which have particularly advantageous properties as luminescent probes.

For example, nanoparticles based on rare earth-doped yttrium vanadate have been described in detail [14] and [15].

These nanoparticles are particularly advantageous in terms of their excellent photostability, which allows the acquisition of a constant and prolonged signal, and the absence of flickering emission phenomena. In addition, they have a narrow emission spectrum and a large Stokes shift (of the order of 350 nm for Eu-doped nanoparticles) of the emission. These nanoparticles also contain several tens of thousands of ions that can be excited and responsible for luminescence. The increase in the excitation intensity thus induces an increase in the brightness of the particles, as saturation of the emission is only reached at impracticable intensities.

Finally, these nanoparticles do not lose their luminescence after freezing.

Rare earth-based photoluminescent nanoparticles have already been proposed as luminescent probes in various applications [16].

For example, Dosev et al. [17] take advantage of the luminescence properties of luminescent nanoparticles of Eu:Gd$_2$O$_3$ by excitation of the Gd$_2$O$_3$ matrix for the detection of protein microstructures deposited on a substrate. Yi et al. [18], in turn, use upconversion phosphors of photons of nature NaYF$_4$:Yb,Er, which absorb two near-IR photons to emit one photon in the visible.

Rare earth-based photoluminescent nanoparticles have also already been implemented for single particle detection as well as for single molecule tracking, taking advantage of the lack of flicker for single particle detection, in comparison with semiconductor nanoparticles or quantum dots ([19] and [20]). However, it was by no means foreseeable that these lanthanide-ion-based nanoparticles could be used for ultrasensitive detection and quantification of biomolecules, in the case of an overall detection of biomolecules. Indeed, apart from the absence of flickering, the luminescence properties of luminescent nanoparticles based on rare earths are considered inferior to those of quantum dots. In these particles, in particular those consisting of a metal oxide matrix in which certain ions are substituted by rare-earth ions, luminescence can be excited either by excitation of the matrix followed by a transfer of energy to the luminescent rare-earth ions, or by direct excitation in the visible range of the luminescent rare-earth ions. Concerning the excitation of the matrix, its absorption band is generally in the UV, which has two disadvantages: few lasers are currently available at these wavelengths, and existing lasers are bulky and expensive; and, at these absorption wavelengths, biomolecules absorb and emit strongly, which can produce interfering signals. Concerning the direct excitation of rare-earth ions, the extinction coefficient for a nanoparticle is lower than that of quantum dots but can be comparable to that of an efficient organic fluorophore [16]. In addition, direct absorption peaks of rare-earth ions in the visible are generally very spectrally narrow, which necessitates the use of a spectrally narrow laser for efficient direct excitation of luminescent rare-earth ions. This type of laser, particularly in the form of a compact and inexpensive laser diode, was not available for the wavelengths concerned for the direct excitation of luminescent rare-earth ions until very recently.

Yuan et al. [21], in a review article, present time-resolved luminescence bioassays using lanthanide-based nanoparticles. Lanthanide-based luminescent probes are particles comprising lanthanide complexes, which limit the number of lanthanide ions per particle for a given particle volume, or upconversion nanoparticles. For example, in publications using nanoparticles including lanthanide complexes, small diameter (8-9 nm) nanoparticles contain only between 3000 and 5000 ions [28]. Only nanoparticles of much larger sizes, especially those larger than 100 nm, can contain 30 000 or more ions [22] and [23].

Similarly, Corstjens et al. [24] use upconversion nanoparticles for the in vitro detection of IFN-gamma in human peripheral blood mononuclear cells. Upconversion nanoparticles are suitable for deep tissue imaging (typically excitation in the near IR region of Yb$^{3+}$ where tissue absorbs little compared with the visible). On the other hand, because excitation requires the absorption of two photons, high excitation intensities are required and the number of photons emitted is relatively low.

Lanthanide complexes or chelates are also proposed as luminescent probes for immunoassays in publications [23], [25], [26] and [27]. However, these complexes or chelates typically contain only a single lanthanide ion or, at best, a few (less than 10) lanthanide ions.

Finally, mention may also be made of the publication Zhou et al. [28] which proposes a detection method with improved sensitivity based on lanthanide-doped inorganic nanoparticles, following a complex protocol for dissolving the nanoparticles and detecting the emission of micelles containing the lanthanides thus formed.

Document EP 1 282 824, in turn, describes the use of surface-modified inorganic luminescent nanoparticles as probes for detecting biological or other organic substances. The detection method proposed in this document is based on the principle of ELISA detection. However, this document in no way proposes their use for ultrasensitive detection.

Mention may also be made of document U.S. Pat. No. 7,550,201, which proposes the use of lanthanide-ion-doped inorganic nanoparticles, notably for their application in diagnostics. However, this document in no way proposes their use for an ultrasensitive detection method.

Also, the publications Son et al. [36] and Nichkova et al. [37] propose the use of Eu:Gd$_2$O$_3$ nanoparticles as an alternative to organic fluorophores as probes for the detection of DNA and phenoxybenzoic acid, respectively. However, these documents in no way suggest their use for ultrasensitive detection.

Thus, it has never been proposed to take advantage of photoluminescent nanoparticles as previously defined, combining specific optical and physicochemical properties, in an ultrasensitive detection method according to the invention.

These photoluminescent nanoparticles can be obtained by conventional synthesis methods known to the person skilled in the art.

The crystalline matrix forming the photoluminescent inorganic nanoparticle may be an oxide matrix, for example a vanadate or phosphate matrix; a halogen matrix, for example a fluoride matrix; or a chalcogenide matrix, for example tellurium, sulfide, selenide.

Alternatively, advantageously, as detailed hereinbelow, the inventors have developed a novel way of synthesizing nanoparticles doped with rare-earth ions using tetraalkylammonium cations on the surface of the nanoparticles, and making it possible to achieve improved stability of the nanoparticles in aqueous medium and, advantageously, better reproducibility of their synthesis and the subsequent steps of functionalization and coupling to a targeting agent.

Finally, the ultrasensitive method of the invention proves to be particularly advantageous in terms of ease of implementation and cost, in comparison with the ultrasensitive technologies discussed above.

Advantageously, and unlike the complex technologies developed by Quanterix and Singulex, it implements a compact detection apparatus of limited cost, each component of which is readily available for purchase, for the excitation and measurement of luminescence emitted by the nanoparticles, as detailed hereinbelow, and does not require any apparatus component specifically dedicated to the ultrasensitive detection method of the invention. Advantageously, it is thus compatible with integration into an automated analysis device with limited ergonomic adaptation.

Figure 22:
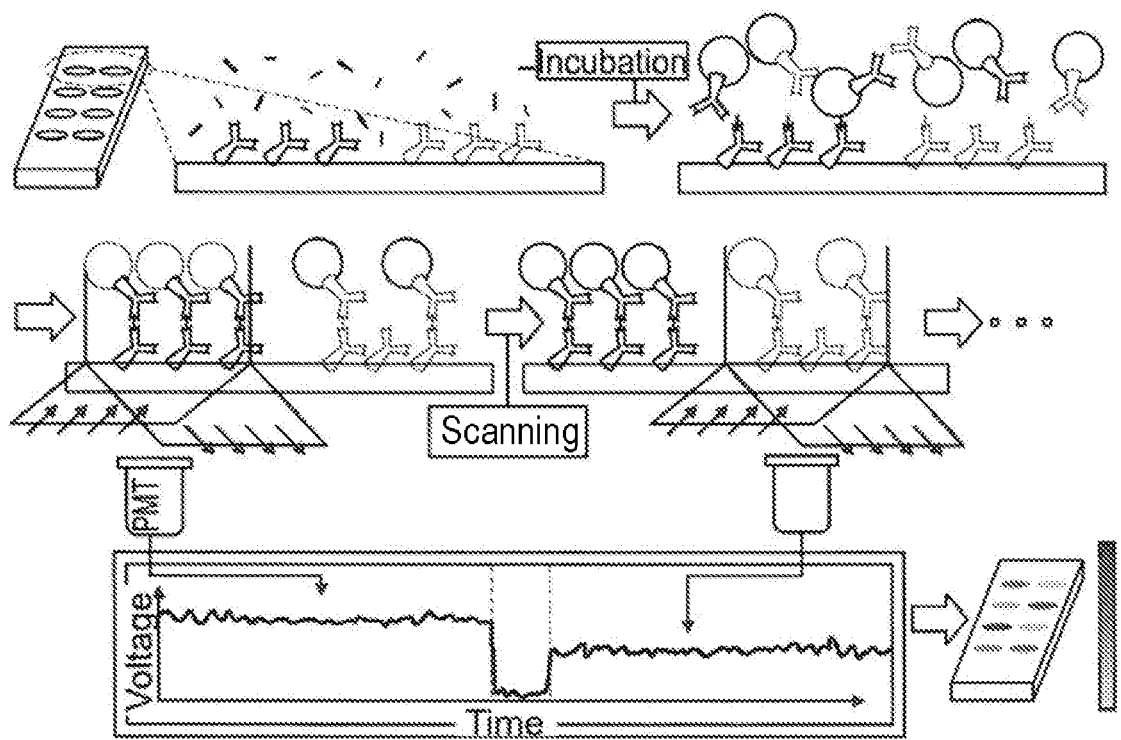

The method of the invention is further adapted for multiplexed analysis. Thus, the method of the invention can be implemented for the simultaneous detection and/or quantification of at least two different substances in a sample, following a procedure presented below (FIG. 22).

Also, as detailed hereinbelow, it is possible to take advantage of the long emission duration (greater than 1 μs, even greater than 10 μs, or even greater than 100 μs) of the particles of the invention to perform time-resolved detection, in particular delayed emission detection. A time-resolved luminescence measurement has been described, for example, in WO 03008974. The ultrasensitive method of the invention advantageously allows time-resolved luminescence detection to be performed using a low-sophistication, low-cost apparatus, in particular a mechanical chopper, a conventional photomultiplier and a 100 kHz A-D converter, as described hereinbelow.

The invention concerns, according to another of its aspects, the use of the process defined above for in vitro diagnostic purposes. Advantageously, the possibility by the ultrasensitive method of detecting ultralow levels of certain substances in biological samples makes it possible, for example, to use the method of the invention for the earlier detection of diseases, or to diagnose the course of a disease or the effect of a therapeutic treatment. In addition, this ultrasensitive detection method allows the use as biomarkers of substances whose concentration is currently too low to be detected with conventional methods. It also makes biomarkers detectable in easily accessible biological media (saliva, urine, blood, etc.) whose concentration is too low to be detected with conventional methods and requires invasive methods such as cerebrospinal fluid sampling, for example.

According to yet another if its aspects, the invention concerns an in vitro diagnostic kit, comprising at least:
photoluminescent particles consisting, in whole or in part, of a photoluminescent inorganic nanoparticle as defined above,
said particles being surface functionalized with chemical groups, for example carboxyl, amino, thiol, aldehyde or epoxy groups, provided by molecules, for example citric acid or polyacrylic acid, and/or coupled to molecules, for example streptavidin, said chemical groups or molecules being capable of allowing coupling of said particles with a targeting agent for the substance to be analyzed; or
said particles being already coupled to at least one targeting agent for the substance to be analyzed; and
a detection and/or quantification system comprising at least:
an illumination device, preferably of the laser type, with a power of at least 50 mW or even at least 500 mW, and an optical arrangement for shaping the laser beam making it possible to obtain an excitation intensity at the level of the sample of at least 1 W/cm$^2$, preferably at least 10 W/cm$^2$;
a device for detecting the light intensity emitted by the particles.

The illumination device may also include another source of excitation, such as a lamp or a light-emitting diode (LED).

Such an in vitro diagnostic kit allows the easy implementation of an ultrasensitive detection and/or quantification method according to the invention, for example for the determination of biomarkers or antibodies in a biological sample.

The diseases that can be diagnosed with the in vitro diagnostic kit of the invention are not limited and include all diseases revealed by the presence of a marker specific to the disease, of the type of molecule of biological interest (protein, nucleic acid, etc.), for which there are one or more specific binding partners (ligand, antibodies, complementary nucleic acids, aptamers, etc.).

Examples include infectious diseases (bacterial, parasitic, or viral, such as AIDS), inflammatory and autoimmune diseases, cardiological, neurological, or oncological diseases (for example, solid cancers such as breast or prostate cancer).

The ultrasensitive detection process of the invention is not limited to the above-mentioned applications. It can thus be used for the detection of GMO DNA in seeds, for example, or for the detection of a pollutant or a pathogen in water or in food for consumption.

Figure 24:
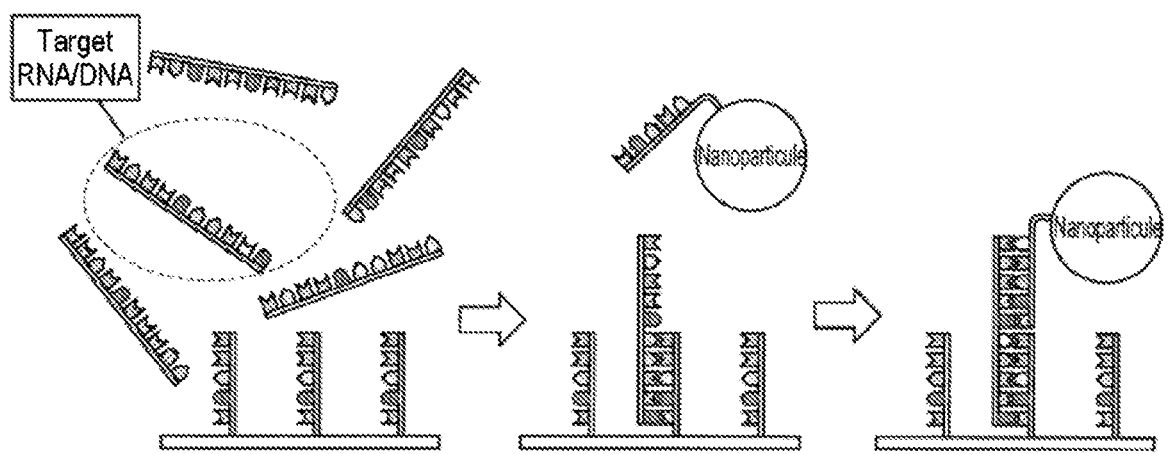
Figure 25:
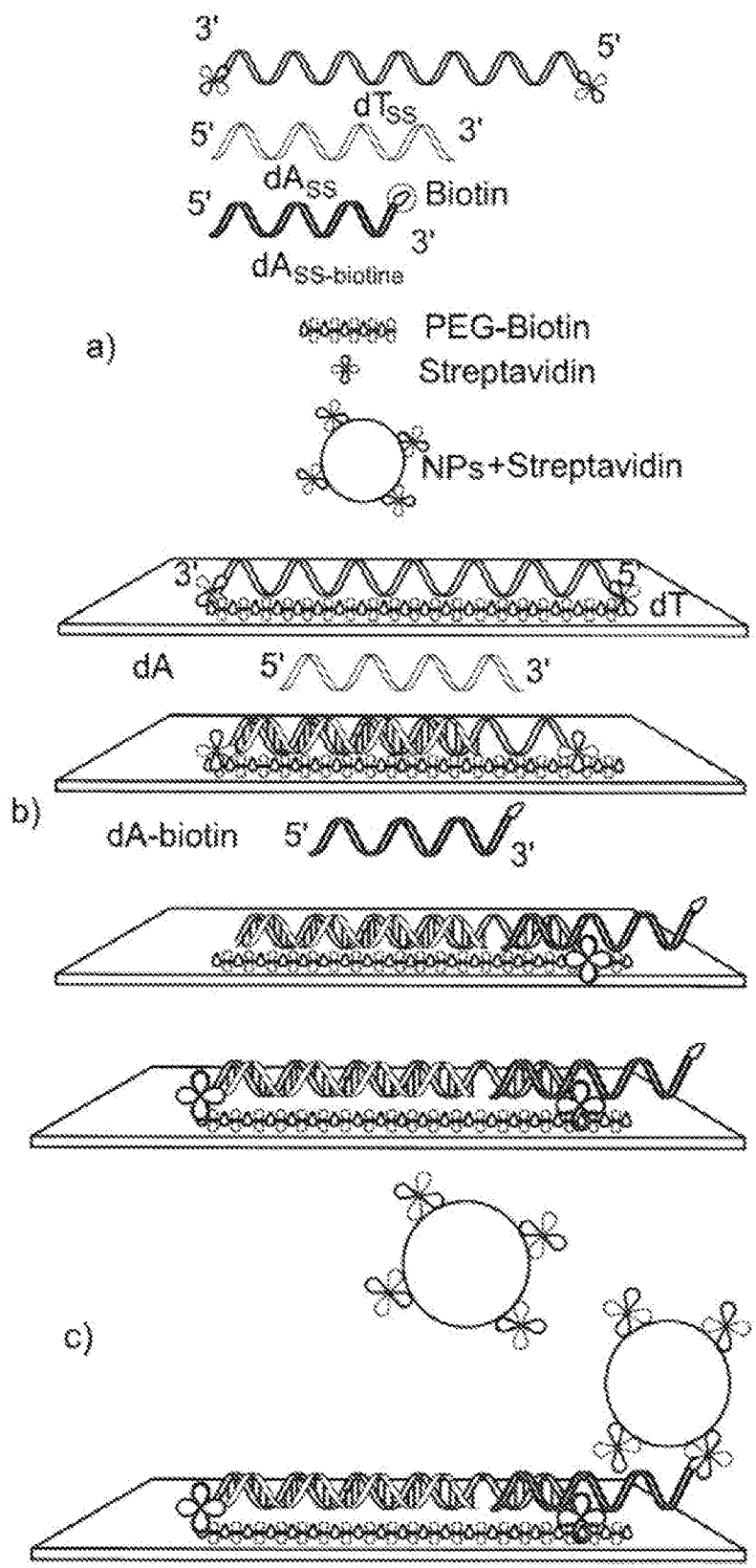

The applications of the ultrasensitive detection process according to the invention can thus extend from immunological fields to molecular genetics or to the detection of DNA and RNA, as illustrated in the appended FIGS. 24 and 25. It can be used to label one or more RNA strands of a biological sample, with a partially complementary probe fragment bound to a nanoparticle, and then detect them by hybridization on complementary fragments of another region grafted onto a solid substrate, following a similar approach to Affymetrix-type DNA chips. One significant feature of the invention then lies in the absence of the amplification step usually necessary for these approaches.

Hereinbelow, the term "nanoparticle" will be used more simply to refer to a photoluminescent inorganic nanoparticle consisting of a crystalline matrix doped with rare-earth ions.

Furthermore, the term "particle" is used to refer to a particle comprising at least said nanoparticle, for example consisting of said nanoparticle, on the surface of which can be located, according to a variant embodiment, tetraalkylammonium cations, and coupled by one or more targeting agent for the substance to be analyzed, as detailed hereinbelow.

Other features, variants and advantages of the process according to the invention will become clearer upon reading the description, examples and figures that follow, given by way of non-limiting illustration of the invention.

Hereinbelow, the expressions "between . . . and . . . ", "ranging from . . . to . . . " and "varying from . . . to . . . " are equivalent and are intended to mean that the bounds are included, unless otherwise specified.

Unless otherwise specified, the expression "comprising one" should be understood as "comprising at least one".

Luminescent Particles of the Invention

As mentioned above, the ultrasensitive detection process according to the invention is based on the detection of the luminescence emission of photoluminescent particles comprising, in particular consisting of, a photoluminescent inorganic nanoparticle having specific optical and physicochemical properties, and coupled to at least one targeting agent for the substance to be analyzed.

Photoluminescent Inorganic Nanoparticle

The properties of the nanoparticles used will condition the sensitivity that can be achieved by the method of the invention.

The inorganic nanoparticles of the invention consist of a crystalline matrix having at least $10^3$ rare-earth ions.

The rare-earth ions in the nanoparticles of the invention are not in the form of rare-earth ion complexes or chelates consisting of rare-earth ions in combination with suitable organic ligands, as for example described in the publication Yuan et al. [21].

Preferably, the nanoparticles of the invention comprise between 1000 and 6 000 000 rare-earth ions, in particular between 5000 and 500 000 and more particularly between 20 000 and 100 000 rare-earth ions.

The nanoparticles of the invention can be doped with rare-earth ions of the same nature or of different natures.

In particular, these may be lanthanide ions selected from europium (Eu), dysprosium (Dy), samarium (Sm), praseodymium (Pr), neodymium (Nd), erbium (Er), ytterbium (Yb), cerium (Ce), holmium (Ho), terbium (Tb), thulium (Tm) and mixtures thereof.

In particular, the lanthanide ions may be selected from Eu, Dy, Sm, Nd, Er, Yb, Tm and Tb and mixtures thereof, in particular from Eu, Dy, Sm, Nd, Er, Yb and mixtures thereof, and more particularly Eu.

The crystalline matrix forming the photoluminescent inorganic nanoparticle may be an oxide matrix, in particular a vanadate or phosphate matrix; a halide matrix, in particular a fluoride matrix; or a chalcogenide matrix, in particular a tellurium, sulfide or selenide matrix.

Fluoride matrices include, in particular, matrices of $YF_3$, $GdF_3$, $NaGdF_4$, $NaYF_4$, $NaLuF_4$, $Ba_4Lu_3F_{17}$, $Na_3ZrF_7$, $Na_5Zr_2F_{13}$ and $Na_7Zr_6F_{31}$.

According to a particular embodiment, the inorganic nanoparticles of the invention are of the following formula (I):

$$(A_{1-x}Ln_x)_a(M_pO_q) \quad (I)$$

wherein:
M represents one or more elements capable of associating with oxygen (O) to form a crystalline compound;
Ln corresponds to one or more luminescent lanthanide ion(s);
A corresponds to one or more constituent ion(s) of the crystalline matrix whose electronic levels are not involved in the luminescence process;
$0<x<1$, in particular $0.1 \leq x \leq 0.9$, in particular $0.2 \leq x \leq 0.6$, in particular $0.2 \leq x \leq 0.4$ and more particularly x is 0.4; and
the values of p, q and a are such that the electroneutrality of $(A_{1-x}Ln_x)_a(M_pO_q)$ is respected.

A can be more particularly selected from yttrium (Y), gadolinium (Gd), lanthanum (La), bismuth (Bi), lutetium (Lu) and mixtures thereof, in particular A can be selected from Y, Gd, La and mixtures thereof; in particular A represents Y or Gd, preferably A represents Y.

In particular, M in the above-mentioned formula (I) can represent one or more elements selected from V, P, W, Mo, As, Al, Hf, Zr, Ge, Ti, Sn, Mn and Si. Preferably, M represents one or more elements selected from V, P, Al, Hf, Zr, Ge, Ti, Sn, Mn and Si, and in particular selected from V, P, W, Mo, As and Al. The crystalline matrix of the nanoparticles used according to the invention may incorporate one or more types of $M_pO_q$ anions, In particular M may represent $V_{1-y}P_y$ with y ranging from 0 to 1.

According to a particular embodiment, p in the above-mentioned formula (I) is different from zero.

By way of example, a nanoparticle of the invention may be of formula (I) wherein M represents V and/or P, p is 1, so that the matrix of said nanoparticle comprises $VO_4^{3-}$ and/or $PO_4^{3-}$ anions.

In another example embodiment, M represents Al, A represents Y or Lu, p is 5 and q is 12, so that the $A_a(M_pO_q)$ matrix of said nanoparticle is the garnet $Y_3Al_5O_{12}$ (YAG) or $Lu_3Al_5O_{12}$ (LuAG).

According to another particular embodiment, a nanoparticle of the invention may be of formula (I) wherein M represents Hf or Zr, Ge, Ti, Sn, Mn, p is 2 and q is 7, so that the matrix of said particle is $A_aHf_2O_7$, $A_aZr_2O_7$, $A_aGe_2O_7$, $A_aTi_2O_7$, $A_aSn_2O_7$ or $A_aMn_2O_7$. In particular, A may represent La, Y, Gd or Lu, in which case a=2.

In another example embodiment, p is zero and A is Y or Gd, so that the $A_a(M_pO_q)$ matrix of said nanoparticle is of the type $Y_2O_3$ or $Gd_2O_3$.

According to a particular embodiment, the nanoparticles used in a method according to the invention may be more particularly metal oxide nanoparticles doped with one or more rare-earth ions, in particular with one or more lanthanide ions.

The rate of substitution of the ions of the crystalline matrix of the nanoparticles according to the invention, in particular of the metal oxide matrix, by rare-earth ions can be more particularly between 10% and 90%, in particular between 20% and 60%, notably between 20% and 40% and more particularly can be 40%.

It was counterintuitive to choose such high levels of doping. Indeed, generally speaking, the usual doping rates of luminescent nanoparticles doped with rare-earth ions are kept below 10% to avoid the quenching effect that occurs at higher concentrations [29] to [31].

Advantageously, the imperfect crystallinity of the nanoparticles according to the invention, as described more precisely below, makes it possible to eliminate the quenching effect. In addition, the process according to the invention, by directly exciting the rare-earth ions of the nanoparticles (and not only the matrix as is conventionally the case), makes it possible, in combination with greater doping with rare-earth ions, to access a greater number of absorbed excitation photons, and therefore a greater number of emitted and detected photons.

The photoluminescent nanoparticles of the invention have an average size greater than or equal to 20 nm and strictly less than 1 μm.

In particular, they have an average size between 20 nm and 500 nm, in particular between 20 nm and 200 nm and especially between 20 nm and 100 nm.

In particular, the average size of the photoluminescent nanoparticles of the invention may be greater than or equal to 25 nm, in particular greater than or equal to 30 nm, notably between 30 and 60 nm.

In particular, as illustrated in the following examples, the photoluminescent nanoparticles according to the invention may have an average size in the range of 30 to 50 nm.

Larger nanoparticles can be obtained, for example, by centrifugal size sorting of the particles as exemplified to retain only the largest particles in the size distribution, or can be obtained by grinding the solid material. Any other technique known to the person skilled in the art may also be used.

The photoluminescent nanoparticles used in the process of the invention thus have a sufficient volume to contain a large number of rare-earth ions, and thus emit a luminescent signal sufficient to allow the detection of low concentrations. By way of example, a spherical nanoparticle $Y_{0.6}Eu_{0.4}VO_4$ with a diameter of 30 nm contains 70 000 $Eu^{3+}$ ions (calculation of the number of ions according to reference [35] Casanova et al. APL 2006). In addition, the photoluminescent nanoparticles should not be too large to avoid steric hindrance when combined with the substance to be assayed immobilized, for example, on the surface of a support, as described hereinbelow.

The average size can be measured by transmission electron microscopy. Transmission electron microscopy images can be used to determine the shape of nanoparticles (spherical, ellipsoidal) and to deduce the average dimensions of nanoparticles. In the case of generally spherical particles, the average size refers to the average diameter of the particles.

In the case of ellipsoidal particles, the average size is the average size of a sphere of the same volume as the ellipsoid. It is generally assumed that the third axis of the ellipsoid, not visible in transmission images which are 2D projections, is equal in length to the smaller axis.

According to a particular embodiment, the nanoparticles of the invention are prolate, i.e. have a generally elongated ellipsoidal shape.

They may more particularly have a major axis length, denoted a, of between 20 and 60 nm; and a minor axis length, denoted b, of between 10 and 30 nm. In particular, the nanoparticles of the invention may have an average major axis length value, a, of 40 nm and an average minor axis length value, b, of 20 nm.

Advantageously, the nanoparticles of the invention have a low polydispersity. The polydispersity index, which can be deduced from MET measurements, may in particular be strictly less than 0.2.

According to a particular embodiment, the product between the doping rate of rare-earth ions, for example in europium (Eu), and the quantum efficiency of the emission by the nanoparticle is maximized.

This is particularly advantageous for an excitation, according to step (ii) of the process of the invention, of rare-earth ions by direct excitation, i.e. in resonance with the electron states of these ions, and not by excitation of the $A_a(M_pO_q)$ matrix as defined above, for example $AVO_{4(1-y)}(PO_4)_y$, and subsequent energy transfer to these ions.

This optimization of the product between the Ln-ion doping rate x and the quantum efficiency can be achieved using a high Ln-ion doping, for example between 0.2 and 0.6, and notably 0.4, without reducing the quantum efficiency, in particular by limiting the transfer processes between doping ions leading to concentration quenching. In particular, in order to maintain a high quantum efficiency, the nanoparticle has imperfect crystallinity. In fact, excellent crystallinity favors transfer processes between doping ions, especially when they are in close proximity to each other, as is the case with high doping, and therefore favors processes of de-excitation of the ions by non-radiative processes, linked to the surface and the presence of the solvent. In particular, a synthesis process at room temperature, or at least at a temperature not exceeding 600° C., is favorable for the imperfect crystallinity required for these nanoparticles.

The crystallinity of nanoparticles is considered "imperfect" when the coherence length determined by the X-ray diffractogram in at least one crystallographic direction is less than 80% of the particle size in that direction as measured from transmission electron microscopy images. Different types of imperfect crystallinity can be considered: polycrystallinity, defects, porosity, etc.

Advantageously, the nanoparticles used in the context of the process of the invention are capable of emitting more than $10^8$ photons before the emission stops, in particular more than $10^9$, or even more than $10^{10}$ photons. In many cases, especially in the case of Eu-doped $YVO_4$ or $GdVO_4$ particles, no cessation of emission is observed.

In a particularly advantageous variant embodiment of the invention, the relative variation of the luminescence signal in relation to the signal expected for linear behavior under the excitation conditions used in the context of the process of the invention, is always less than 30%.

In particular, the nanoparticles used in the context of the detection process of the invention are such that there is no saturation of the luminescence signal at high excitation intensities (in particular, greater than 1 W/cm$^2$). This is more particularly the result of the presence of a large number of rare-earth ions (greater than $10^3$ rare-earth ions) within the particle.

Advantageously, the detection process of the invention is therefore not restricted by saturation phenomena and other adverse effects, such as photodegradation, which can occur at high excitation with certain photoluminescent probes, such as organic fluorophores or fluorescent proteins. The absence of saturation and other effects thus advantageously permits excitation according to the process of the invention at high power (at least 50 mW) and high excitation density (at least 1 W/cm$^2$).

Furthermore, advantageously, the nanoparticles of the invention have a long emission lifetime. In particular, they may have an emission lifetime greater than or equal to 5 µs, in particular greater than or equal to 10 µs, notably greater than or equal to 20 µs, or greater than or equal to 50 µs.

Emission lifetime is understood as the lifetime of the excited state of the emitting nanoparticle and is determined in practice by the duration of the emission of luminescence photons after the excitation has stopped, i.e. the characteristic time of the exponential decline of luminescence after the excitation has stopped.

The ultrasensitive method of the invention advantageously makes it possible to take advantage of the long emission duration of the particles of the invention (a few hundred µs in the case of $Y_{1-x}Eu_xVO_4$ particles, in comparison with the lifetime of usual fluorophores of the order of nanoseconds), in order to carry out time-resolved detection, in particular delayed emission detection, with sufficient time resolution (10 µs), using a low-sophistication, low-cost apparatus, in particular a mechanical chopper, a conventional photomultiplier and a 100 kHz A-D converter, as described hereinbelow.

Advantageously, the nanoparticles of the invention exhibit good colloidal stability in solution.

The stability of nanoparticles in solution is particularly critical to meet the requirements for reproducibility of detection results from the use of these particles as probes.

The "zeta potential" is one of the elements representative of the stability of a suspension. For example, it can be measured directly with a Zetasizer Nano ZS from Malvern. This apparatus uses optical devices to measure the velocities of movement of the particles as a function of the electric field applied to them.

In particular, the nanoparticles of the invention advantageously present, at the end of their synthesis, a zeta potential, in absolute value, denoted $|\zeta|$, in aqueous medium at pH 5, greater than 30 mV.

More particularly, the nanoparticles of the invention advantageously have a zeta potential less than or equal to −28 mV, preferably less than or equal to −30 mV, in aqueous medium of pH≥5, in particular of pH≥5.5, and more particularly of pH≥6, and of ionic conductivity strictly less than 100 µs·cm$^{-1}$.

In particular, the nanoparticles of the invention possess a zeta potential less than or equal to −30 mV, in aqueous medium of pH≥6.5, in particular of pH≥7, notably of pH≥8, and of ionic conductivity strictly less than 100 µs·cm$^{-1}$.

The "zeta potential", denoted $\zeta$, can be defined as the potential difference existing between the interior of the solution, and the shear plane of the particle. It is representative of the stability of a suspension. The shear plane (or hydrodynamic radius) corresponds to an imaginary sphere around the particle in which the solvent moves with the particle as the particles move through the solution. The zeta potential can be determined by methods known to the person skilled in the art, for example by moving the particle with its solubilization layer in an electric field, as detailed hereinbelow.

This negative zeta potential of the nanoparticles less than or equal to −28 mV, in particular less than or equal to −30 mV, in aqueous medium at pH≥5, in particular at pH≥6.5, increases the phenomena of electrostatic repulsion of the nanoparticles in aqueous solution relative to one another, thus making it possible to suppress flocculation phenomena. Indeed, it is empirically known to the person skilled in the art that a high absolute zeta potential, especially above 28 mV, generally suppresses the effects of flocculation in media with low ionic strength.

According to a variant embodiment, a nanoparticle used in the ultrasensitive detection method according to the invention is a nanoparticle of the following formula (II):

$$A_{1-x}Ln_xVO_{4(1-y)}(PO_4)_y \qquad (II)$$

wherein:
- A is selected from yttrium (Y), gadolinium (Gd), lanthanum (La), lutetium (Lu), and mixtures thereof, in particular A is selected from Y, Gd, La and mixtures thereof and more particularly A represents Y;
- Ln is selected from europium (Eu), dysprosium (Dy), samarium (Sm), neodymium (Nd), erbium (Er), ytterbium (Yb), thulium (Tm), terbium (Tb), and mixtures thereof, preferably Ln represents Eu;
- $0<x<1$, in particular $0.2 \leq x \leq 0.6$ and more specifically x is 0.4; and
- $0 \leq y<1$, in particular y is 0.

According to a particular embodiment, the nanoparticle has the above-mentioned formula (II) wherein y is 0. In other words, the nanoparticle used in the process of the invention is of formula $A_{1-x}Ln_xVO_4$ (III), wherein A, Ln and x are as defined above.

According to a particular embodiment, A in the above-mentioned formula (II) or (III) represents yttrium (Y).

According to another particular embodiment, Ln in the above-mentioned formula (II) or (III) represents Eu.

Thus, according to a variant embodiment, the particles of the invention comprise a nanoparticle of formula $Y_{1-x}Eu_xVO_4$ (IV) wherein $0<x<1$, in particular $0.2 \leq x \leq 0.6$ and more particularly x is 0.4.

Preferably, the nanoparticles of formulae (II), (III) or (IV) used according to the invention have tetraalkylammonium cations on their surface.

Advantageously, the use of these voluminous counterions provides an improved colloidal stability of the particles in solution and prevents particle flocculation phenomena in particular. Without wanting to be bound by the theory, this improvement in terms of stabilization, resulting from the use of tetraalkylammonium counterions, compared for example to the use of sodium ions, is linked to the difference in the zeta potential of the particles. In fact, the use of tetraalkylammonium counterions induces a negative zeta potential of the particle of increased absolute value, in comparison with, for example, the use of sodium counterions.

It should be noted that this stability is important even in media with high ionic strength as is the case in the synthesis medium even before purification (ionic strength greater than 0.1 M). In particular, an aqueous suspension of particles according to the invention exhibits little or no flocculation phenomenon over periods of several weeks.

The immobilization of tetraalkylammonium type cations on the surface of the nanoparticles of the invention results more particularly from electrostatic interactions between negatively-charged ($O^{2-}$) surface ions of the nanoparticle of formula (II) and positively-charged tetraalkylammonium type counterions.

Thus, tetraalkylammonium cations are directly associated with the nanoparticle via electrostatic interactions with the negatively-charged surface ions of the nanoparticle. In particular, the immobilization of tetraalkylammonium cations on the surface of the nanoparticle does not involve any "spacer" groups.

More particularly, the term "tetraalkylammonium" cations refers to tetra($C_1$-$C_6$)alkylammonium cations, i.e. cations of formula $NR_4^+$ with R, which may be identical or different, representing a $C_1$-$C_6$-alkyl, in particular $C_1$-$C_4$-alkyl group.

Preferably, the "tetraalkylammonium" cations are tetra($C_1$-$C_3$)alkylammonium cations, i.e. cations of formula $NR_4^+$ with R, which may be identical or different, representing a $C_1$-$C_3$-alkyl group.

"$C_1$-$C_6$-alkyl" means a saturated, linear or branched aliphatic group having from 1 to 6 carbon atoms. Examples include methyl, ethyl, propyl, butyl, isopropyl, isobutyl, tertbutyl, etc.

The tetraalkylammonium cations are preferably selected from tetramethylammonium, tetraethylammonium, tetrapropylammonium, tetrabutylammonium cations and mixtures thereof.

According to a particular embodiment, the cations present on the surface of the nanoparticles of the invention are tetramethylammonium cations.

As indicated above, the tetraalkylammonium cations are present on the surface of the nanoparticles of the invention in an amount sufficient to provide the desired result in terms of the colloidal stability of the aqueous suspension of said synthesized particles, i.e. the desired zeta potential value.

The tetraalkylammonium cations present on the surface of the nanoparticles of the invention may be present in a ratio of 100 to 10 000 tetraalkylammonium cations per nanoparticle.

The nanoparticles of the invention may thus be nanoparticles of the following formula (II'):

$$A_{1-x}Ln_xVO_{4(1-y)}(PO_4)_y \cdot (NR_4^+)_z \qquad (II')$$

wherein:
- A is selected from Y, Gd, La, Lu and mixtures thereof, in particular A is selected from Y, Gd, La and mixtures thereof, preferably A represents Y;
- Ln is selected from Eu, Dy, Sm, Nd, Er, Yb, Tm, Tb and mixtures thereof, preferably Ln represents Eu;
- $0<x<1$, in particular $0.2 \leq x \leq 0.6$ and more particularly x is 0.4;
- $0 \leq y<1$;
- R, which may be identical or different, are as defined above, preferably represent a $C_1$-$C_3$-alkyl, in particular methyl group; and
- z represents the number of tetraalkylammonium cations $NR_4^+$ located on the surface of said nanoparticle, in particular z is between 100 and 10 000.

According to a particular embodiment, the nanoparticle has the above-mentioned formula (II') wherein y is 0. In other words, a nanoparticle of the invention may more particularly have the formula $A_{1-x}Ln_xVO_4 \cdot (NR_4^+)_z$ (III'), wherein A, x, Ln, R and z are as defined above.

According to a particular embodiment, A in the above-mentioned formula (II') or (III') represents yttrium (Y).

According to another particular embodiment, Ln in the above-mentioned formula (II') or (III') represents Eu.

Thus, according to a particular variant embodiment, a nanoparticle of the invention may more particularly have the formula $Y_{1-x}Eu_xVO_4 \cdot (NR_4^+)_z$ (IV'), wherein x, R and z are as defined above.

It is understood that the different embodiments mentioned above, notably concerning the nature of the photoluminescent nanoparticle and of the surface tetraalkylammonium cations, may be combined.

By way of example, a photoluminescent particle used according to the invention may comprise a nanoparticle of formula $Y_{0.6}Eu_{0.4}VO_4$ on the surface of which tetramethylammonium cations are optionally immobilized.

In particular, it may have the formula $Y_{0.6}Eu_{0.4}VO_4 \cdot (NR_4^+)_z$, z representing the number of tetraalkylammonium cations.

The nanoparticles according to the invention, in particular the nanoparticles of the above-mentioned formula (II), are predominantly crystalline and polycrystalline in nature, in particular of average crystallite size, as deduced by X-ray diffraction, as detailed in Example 1 below, between 3 and 40 nm.

Preparation of Nanoparticles

The rare-earth-ion-doped crystalline-matrix nanoparticles used in the process of the invention can be prepared by any conventional method known to the person skilled in the art.

Advantageously, the nanoparticles of the invention are easily synthesized, in aqueous medium, which has the advantage of dispensing with any subsequent solvent transfer step.

In particular, the nanoparticles of formula $A_{1-x}Ln_x VO_{4(1-y)}(PO_4)_y$ (II) can be formed by coprecipitation reaction, in aqueous medium, from precursors of said elements A and Ln, and in the presence of orthovanadate ions ($VO_4^{3-}$) and optionally phosphate ions ($PO_4^{3-}$).

The precursors of the elements A and Ln may be conventionally in the form of salts of said elements, for example nitrates, chlorides, perchlorates or acetates, in particular nitrates. The precursors of the elements A and Ln, and their amounts, are of course selected appropriately with regard to the nature of the desired nanoparticle.

For example, the synthesis of nanoparticles of formula $Y_{1-x}Eu_xVO_4$ (IV) can use, as yttrium and europium precursor compounds, yttrium $(Y(NO_3)_3)$ and europium $(Eu(NO_3)_3)$ nitrates.

Advantageously, the coprecipitation reaction is carried out in the presence of an effective amount of tetraalkylammonium cations.

The tetraalkylammonium cations are more particularly as defined above. They are preferably selected from tetramethylammonium, tetraethylammonium, tetrapropylammonium, tetrabutylammonium cations and mixtures thereof. They are preferably tetramethylammonium cations.

More particularly, "effective amount" means that the cations are used in an amount sufficient to provide the desired result in terms of colloidal stability of the aqueous suspension of said synthesized particles.

In particular, the tetraalkylammonium cations are used in an amount such that the nanoparticles obtained from the synthesis process of the invention have a zeta potential as indicated above. As illustrated in Example 1 below, the tetraalkylammonium cations in the coprecipitation reaction according to the invention are counterions of orthovanadate ions ($VO_4^{3-}$), and optionally of phosphate ions ($PO_4^{3-}$) (in the case where $y \neq 0$).

According to a particularly preferred embodiment, the orthovanadate ions ($VO_4^{3-}$) are generated in situ from a metavanadate salt, preferably ammonium metavanadate ($NH_4VO_3$).

The orthovanadate ions can be more particularly formed in situ by reaction of said metavanadate salt with a base (more precisely with two equivalents of strong base).

In particular, the base used for the in situ formation of orthovanadate ions from metavanadate salt is a source of tetraalkylammonium cations. It may be, for example, a tetraalkylammonium hydroxide, for example tetramethylammonium hydroxide.

The use of a metavanadate salt such as ammonium metavanadate for the synthesis of nanoparticles according to the invention proves particularly advantageous, in comparison with the use of sodium orthovanadate, in that it avoids the reproducibility problems associated with variations in the carbonate content of sodium orthovanadate.

By way of example, the synthesis reaction from ammonium metavanadate and tetramethylammonium hydroxide is shown in Example 1.

It may also be envisaged to use alkylammonium metavanadate (not commercially available) and another strong base, such as ammonium hydroxide.

The process for the preparation of the particles according to the invention may more particularly implement at least the following steps, consisting in:
(i) providing an aqueous solution, denoted solution (1), comprising orthovanadate ions ($VO_4^{3-}$), and optionally phosphate ions ($PO_4^{3-}$), and tetraalkylammonium cations;
(ii) adding to the aqueous solution (1), an aqueous solution, called solution (2), comprising said precursors of the elements A and Ln, in particular in the form of salts, notably of nitrates, under conditions conducive to the formation by coprecipitation of the nanoparticles of formula (II); and
(iii) recovering said nanoparticles of formula (II) on the surface of which are located tetraalkylammonium cations, formed at the end of step (ii).

The aqueous solution (1) can be prepared more particularly by mixing at least one metavanadate salt, in particular ammonium metavanate, and at least one base, source of tetraalkylammonium cations, for example a tetraalkylammonium hydroxide.

In the case of phosphate ions, a phosphate salt, such as sodium phosphate or ammonium phosphate, is added.

Thus, according to a particularly advantageous variant embodiment, the process of the invention comprises at least the steps consisting in:
(i) preparing an aqueous solution (1) by mixing, in aqueous medium, a metavanadate salt, in particular ammonium metavanadate ($NH_4VO_3$), and optionally a phosphate salt, and a base, source of tetraalkylammonium cations, in particular a tetraalkylammonium hydroxide;
(ii) adding to the aqueous solution (1), an aqueous solution (2) comprising said precursors of the elements A and Ln, in particular in the form of salts, in particular of nitrates; under conditions conducive to the formation by coprecipitation of said nanoparticles of formula (II); and
(iii) recovering the nanoparticles of formula (II) on the surface of which are located tetraalkylammonium cations formed at the end of step (ii).

According to a particular embodiment, the addition in step (ii) of the solution (2) to the solution (1) is carried out dropwise.

According to another variant embodiment, the solution (2) can be added to the solution (1) all at once, not dropwise.

The aqueous medium of the solutions (1) and (2) consists more particularly of water.

In a particular embodiment, the aqueous solution (2) containing the precursors of the elements A and Ln may also contain complexing agents of these elements, such as citrate, for example tetraalkylammonium citrate.

It is up to the person skilled in the art to adequately adjust the amounts of the various reagents, in particular of the orthovanadate ion precursors, optionally phosphate, and of said elements A and Ln, with respect to the desired nature of the nanoparticle of formula (II) according to the invention.

In particular, the stoichiometric proportions of the different reagents according to the formulae (II), (II'), (III), (III'), (IV) and (IV') must be observed. When optical excitation of the Ln ions is provided by direct excitation, i.e. in resonance with the electronic states of these ions, as is the case in the ultrasensitive method according to the invention, and not by excitation of the $AVO_{4(1-y)}(PO_4)_y$ matrix and subsequent energy transfer to these ions, as mentioned above, it is preferable to have a high value of x, preferably between 0.2 and 0.6, and preferably 0.4.

Advantageously, the process for preparing nanoparticles does not require any heating of the solution, unlike notably the hydrothermal methods proposed in publications [26] to [29]. In particular, all the steps (i) to (iii) for the synthesis of the particles according to the invention can advantageously be carried out at room temperature (20-25° C.).

Nevertheless, higher temperature preparation processes, for example of hydrothermal type, can produce nanoparticles of similar crystallinity, provided that the temperature does not exceed 600° C., thus allowing access to nanoparticles with imperfect crystallinity as mentioned above, and thus achieving a high quantum yield.

Step (iii) consists more particularly in purifying the solution of particles obtained, notably to remove excess counterions.

The purification steps may more particularly include steps of dialysis or of centrifugation and redispersion of the particles in aqueous medium, for example by sonication.

The particles can be redispersed in aqueous medium, in particular in water. As mentioned above, the aqueous colloidal suspension of the particles of the invention exhibits very good stability, even after storage for several months.

By way of example, the particles consisting, in whole or in part, of a nanoparticle of formula $Y_{1-x}Eu_xVO_4$ (IV), with $0<x<1$, can be prepared via at least the steps consisting in:
(i) providing an aqueous solution (1), comprising orthovanadate ions and tetraalkylammonium cations, said aqueous solution (1) preferably being obtained from the mixture, in aqueous medium, of ammonium metavanadate ($NH_4VO_3$) and a tetraalkylammonium hydroxide;
(ii) adding to the aqueous solution (1), an aqueous solution, called solution (2), comprising precursors of Y and Eu, in particular yttrium and europium nitrates, under conditions conducive to the formation by coprecipitation of the nanoparticles of formula (IV); and
(iii) recovering said nanoparticles of formula (IV) on the surface of which are located tetraalkylammonium cations, formed at the end of step (ii).

As mentioned above, at the end of their synthesis, the nanoparticles have a low polydispersity. The polydispersity index, which can be deduced from MET measurements, may in particular be strictly less than 0.2.

The synthesis of luminescent nanoparticles according to the invention, in particular of larger sizes, greater than a few tens of nanometers, can be carried out by any other approach known to the person skilled in the art, for example by grinding the solid material.

Targeting Agent

The particles used as luminescent probes according to the process of the invention are coupled (or grafted) to at least one targeting agent for the substance to be assayed in the sample to be analyzed.

"Targeting agent" means a compound allowing a bond with a substance of biological or chemical interest, and whose identification is sought.

The nature of the targeting agents used is, of course, selected with regard to the substance to be analyzed in the sample.

The particles used in the ultrasensitive method according to the invention are perfectly adapted to a wide variety of biological targeting, the specificities being dependent on the nature of the targeting agent(s) grafted onto the surface of the nanoparticle.

The targeting agent may be more particularly selected from a polyclonal or monoclonal antibody, an antibody fragment, a nanobody, an oligonucleide, a peptide, a hormone, a ligand, a cytokine, a peptidomimetic, a protein, a carbohydrate, a chemically modified protein, a chemically modified nucleic acid, a chemically modified carbohydrate which targets a known cell surface protein, an aptamer, a protein and DNA/RNA assembly or a chloroalkane used by HaloTag type markers. A SNAP-Tag or CLIP-Tag approach can also be used.

According to a particular embodiment, it is an antibody or antibody fragment.

Suitable antibody fragments comprise at least one variable domain of an immunoglobulin, such as single variable domains Fv, scFv, Fab, (Fab')$^2$ and other proteolytic fragments or nanobodies (single-domain antibodies such as $V_HH$ fragments obtained from camelid antibodies or $V_{NAR}$ fragments obtained from cartilaginous fish antibodies).

The term "antibodies" according to the invention includes chimeric antibodies; human or humanized antibodies, recombinant and modified antibodies, conjugated antibodies, and fragments thereof.

According to a particular embodiment, the antibodies or antibody fragments used according to the invention target markers specific to cancer cells.

The targeting agent can also be derived from a molecule known to bind a cell surface receptor. For example, the targeting fragment may be derived from low-density lipoproteins, transferrin, EGF, insulin, PDGF, fibrinolytic enzymes, anti-HER2, anti-HER3, anti-HER4, annexins, interleukins, interferons, erythropoietins, or colony-stimulating factors.

Coupling of the Particle with the Targeting Agent

It is up to the person skilled in the art to implement the appropriate coupling/grafting methods to adequately prepare the particles coupled to one or more targeting agents. The amount of targeting agent(s) used is adjusted in relation to the amount of particles.

The targeting agent can be grafted to the nanoparticle directly or via a spacer or linker.

The methods for coupling or grafting particles to biomolecules are well known to the person skilled in the art. It is generally coupled by covalent bonding, by surface complexation, by electrostatic interactions, by encapsulation, or by adsorption.

In some cases, including the case of covalent coupling, the particles may be prefunctionalized by chemical groups that can then react with another chemical group carried by the targeting agent to form a covalent bond.

Examples of chemical groups that may be present on the surface of the nanoparticles include carboxyl, amino, thiol, aldehyde and epoxy groups.

Amino groups can be provided by molecules such as amino organosilanes, such as aminotriethoxysilane (APTES). The advantage of APTES is that it forms a capsule around the nanoparticle via covalent bonds. The amines provided by APTES are thus very stable over time. Amino groups can be converted to carboxyl groups by reaction with succinic anhydride.

Carboxyl groups can be provided by molecules such as citric acid or polyacrylic acid (PAA).

For example, the nanoparticles of the invention can be surface functionalized with citrate, as illustrated in Example 1 below.

According to another particular embodiment, the nanoparticles of the invention can be surface functionalized by polyacrylic acid (PAA). In the case of functionalization with PAA, the longer the PAA is in place, the greater the number of coordination bonds (dative bonds) formed by each PAA molecule. For example, the PAA can have a degree of polymerization ranging from 3 to 10 000.

Advantageously, the functionalization of the nanoparticles with PAA leads to functionalized nanoparticles, and to nanoparticles resulting from the coupling of these functionalized nanoparticles with one or more targeting agents, which have excellent properties in terms of stability over time.

In other cases, the particles may be first coupled to molecules capable of allowing subsequent coupling with a targeting agent.

For example, the particles can be coupled to streptavidin capable of allowing coupling with a biotinylated targeting agent.

By way of example, Example 1 illustrates the coupling of nanoparticles with biotinylated antibodies by coupling streptavidin-coupled nanoparticles with biotinylated antibodies. It can also be carried out directly by coupling antibodies on nanoparticles functionalized with citrate or polyacrylic acid.

In other cases, the coupling of nanoparticles with antibodies can be achieved directly by coupling the antibodies to nanoparticles functionalized with APTES. The amino groups provided by APTES can be transformed initially into carboxyl groups by reaction with succinic anhydride, as mentioned above. The carboxyl groups can then be activated by any technique known to the person skilled in the art, in particular by reaction with 1-ethyl-3-(3-dimethylaminopropyl)carbodiimide (EDC) and N-hydroxysuccinimide (NHS), to then react with the amine functions on the surface of a polypeptide and form a covalent amide bond, when the targeting agent is a protein or an antibody.

The functionalization of the nanoparticles by APTES can be done advantageously by coating the nanoparticles with a layer of silica.

The coupling of the targeting agent to the surface of the nanoparticles can also be done by any other method known to the person skilled in the art.

It can also advantageously be done by coating the nanoparticles with a layer of silica, followed by a coating reaction with APTES (3-aminopropyltriethoxysilane), the amine functions of which are used to react with a bifunctional crosslinking agent having two NHS functions. The nanoparticles coupled to the cross-linking agents can then react with the amine functions on the surface of a protein (antibodies, streptavidin, etc.). This type of coupling process is notably described in references [32] and [33].

Advantageously, the particles used in the ultrasensitive detection method according to the invention have a low polydispersity. It is preferable that the polydispersity index, which can be deduced from TEM measurements or dynamic light scattering (DLS) measurements, be strictly less than 0.2. When this is not the case after particle synthesis or functionalization, a lower polydispersity can be obtained by size sorting by centrifugation or by any other technique known to the person skilled in the art.

Association of the Luminescent Probes with the Substance to be Analyzed

In a first step of the ultrasensitive detection method according to the invention, the photoluminescent particles are associated with the substance of the sample to be analyzed.

This step can be performed, similarly to conventional methods, for example the enzyme-linked immunosorbent assay (ELISA), on the surface of a support, as shown schematically in FIG. 1.

This variant embodiment will be discussed in more detail hereinbelow.

It involves notably the prior immobilization, as described in Example 2, of the substance of the sample to be analyzed, on the surface of a support.

In particular, step (i) of the process of the invention may comprise the following steps:
(a) have a support whose surface is previously passivated and functionalized with a targeting agent for the substance to be detected/quantified, for example a first monoclonal antibody, called the capture antibody;
(b) contact said sample to be analyzed with the support of step (a) under conditions conducive to the association of said substance with the targeting agent; and
(c) contact the photoluminescent particles coupled to at least one targeting agent with said support from step (b) to associate the particles with said substance immobilized on the surface of the support.

The support can be of different types. These may be slides, for example glass slides as used in the examples, multi-well plates, microplates, membrane gels, strips or microchannels. It can also be a plastic of good optical quality or any other material of sufficient optical quality.

The surface of the support is first passivated so that the luminescent particles do not attach to it in the absence of the substance to be analyzed.

Surface passivation can be carried out by any method known to the person skilled in the art.

For example, it may be passivation of the glass surface with a molecule comprising polyethylene glycol (PEG), for example with silane-PEG molecules. Preferably, the PEG can have a molar mass of 3000 to 20 000 g·mol$^{-1}$. The longer the PEG, the better the resulting passivation will be. However, the PEG should preferably not be too long so as not to present a steric hindrance to the binding of the substance to be analyzed.

The support is further surface functionalized by a first targeting agent for the substance to be detected/quantified. It may be more particularly an antibody, called the capture antibody, as shown in phase 1 of FIG. 1, notably when the substance to be analyzed is of the biomarker, protein or polypeptide type.

When the substance to be analyzed is of antibody type, the targeting agent may be of type antigen specific for the antibody to be detected.

Surface functionalization can be performed by any method known to the person skilled in the art. It can be done, for example, by spotter printing (depositing microdroplets of solutions containing the targeting molecules on the surface with the aid of a robot), by a contact printing technique which transfers molecules by contact between the topological patterns of a buffer (for example a polydimethylsiloxane PDMS buffer) and the surface of the substrate, or by other means known to the person skilled in the art for depositing the targeting agents on the surface of the substrate.

The sample to be analyzed is then brought into contact with the functionalized surface of said support in such a way as to allow the association of the substance to be detected/assayed with the targeting agent carried by the support (phases 2 and 3 of FIG. 1).

This step involves, as for example in a conventional ELISA, a step of incubating the sample on the surface of the support, and of washing/rinsing the support in order to remove the solution and the unbound molecules. After rinsing, only the targeting agent/assay substance complexes, for example antibody/antigen, remain attached to the surface of the support.

Finally, the photoluminescent particles, as described above, consisting, in whole or in part, of a photoluminescent nanoparticle and coupled to a targeting agent for the substance to be analyzed, for example an antibody, are coupled with the substance to be analyzed immobilized on the surface of the support (phase 4 of FIG. 1).

This step involves incubating the solution of photoluminescent particles on the surface of the functionalized support and then washing/rinsing the support to remove particles not bound to the support. After rinsing, only the targeting agent/assay substance/particle complexes coupled to at least one targeting agent, for example monoclonal antibody/antigen/polyclonal antibody-nanoparticle remain attached to the surface of the support. The incubation time can be adjusted by prior testing to maximize the luminescence emission signal, as shown in Example 4. Generally speaking, it can be between 45 minutes and 2 hours.

The coupling of particles coupled to a targeting agent with the substance to be analyzed may for example involve recognition of a ligand/anti-ligand pair, for example biotin or biotinylated compounds/avidin or streptavidin, hapten/antibody, antigen/antibody, peptide/antibody, such as digoxigenin (DIG)/anti-DIG antibody, sugar/lectin, polynucleotide/polynucleotide complement, etc., it being understood that one of the elements of these pairs constitutes the substance to be analyzed, or may also be coupled to the substance to be analyzed.

It is understood that the substance to be analyzed may be immobilized in several predefined and distinct areas of the surface of the support.

This can be notably achieved by implementing a localized functionalization of the support surface by said targeting agent (for example, capture antibodies), for example by spotter printing (deposition of microdroplets of solutions containing the targeting molecules on the support surface by means of a robot) or by a contact printing technique allowing a functionalization of the support surface according to certain patterns, for example defined by the buffer used to transfer the molecules, as illustrated in Example 2. It can be a deposition in several predefined areas of the same targeting agent. In this case, these multiple areas are used to detect the same substance in several different samples.

Such implementation is more particularly carried out when using the ultrasensitive detection method according to the invention for a multiplexed analysis.

In the context of multiplexed analysis, allowing the simultaneous detection and/or quantification of at least two different substances in a sample, the different substances to be analyzed in the sample can be immobilized in predefined and distinct areas on the surface of the support, for example by locally functionalizing the surface of the support with specific targeting agents for each of the substances to be analyzed. The surface is first passivated so that the photoluminescent particles do not attach to it in the absence of the substances to be analyzed.

In this case, the particles used should have multiple different targeting agents on their surface, and in particular at least one specific targeting agent for each of the substances to be analyzed. In this way, the substances to be analyzed will be quantified by the emission intensity of the particle in each area, the spatial location of the area in question indicating the nature of the substance. The implementation of the ultrasensitive method of the invention according to spatial multiplexing is illustrated schematically in FIG. 22.

It is also possible to combine multiplexed approaches for several samples and for several substances to be analyzed by locally functionalizing predefined and distinct areas of the support surface by specific targeting agents for each of the substances to be analyzed, and this repeatedly as many times as the number of samples to be analyzed. In this case, the emission intensity of the particle in each area indicates the presence and/or concentration of each substance to be analyzed in each sample, the spatial location of the area in question indicating both the nature of the substance and the number of samples.

The areas concerning different substances in each sample can be separated from each other by a watertight barrier. In this way, contacting the sample, containing the different substances to be analyzed, with all the areas concerning the same sample on the surface of the support (step (b) above) can be done in a single step and without increasing the required volume.

It is also possible for multiplexed detection to use at least two types of nanoparticles, doped with distinct rare-earth ions, having distinct emission wavelengths, for example $YVO_4$:Eu and YAG:Ce, and coupled to targeting agents for each of the substances to be analyzed. By detecting the luminescence signal using two different emission filters, each of the substances to be analyzed can be detected and/or assayed.

Preferably, in the context of such a multiplexed detection variant, at least two types of nanoparticles having distinct emission wavelengths, and each coupled to targeting agents for each of the substances to be analyzed, may be used so as to separate the luminescence signals obtained.

The combination of the two approaches can also be used (analysis of several different samples and several different substances in each sample), notably for the comparison of the concentrations of target molecules between at least two samples, this being carried out by comparing the intensities of the emission colors of each of the nanoparticles, each coupled to the specific targeting agent of each substance to be analyzed, for several deposition areas each corresponding to a different sample.

Alternatively, the combination of the two approaches can also be used—analysis in several different samples (samples of different origin, or of the same origin at different times, under different conditions, under different stimuli, etc.) of several different substances in each sample—notably for the comparison of target molecule concentrations between at least two samples. This is done by comparing the intensities of the emission colors of each of the nanoparticles, each coupled to the specific targeting agents of each substance to be analyzed, for several deposition areas corresponding to different target molecules. In this case, the comparison of the emission colors at a given spot provides a comparison of the concentrations of a molecule between the two samples.

Various other combinations of these approaches can be envisaged: for example, analyzing four substances using two types of nanoparticles with two different emission colors, each coupled to two of the four different targeting agents required for the recognition of the four substances to be analyzed, and two distinct areas of the support surface locally functionalized by two of the four specific targeting agents for each of the substances to be analyzed.

The invention is of course not limited to the variant embodiment described below wherein the substance to be analyzed is immobilized on the surface of a support (such as glass slides or multi-well plates, for example). Other configurations are conceivable for measuring the luminescence of photoluminescent particles associated with the sample substance to be analyzed.

Other configurations are conceivable for the association of the photoluminescent particles of the invention with the substance to be analyzed.

Variant embodiments may involve, for example, test strips wherein the analyte migrates from one end to the other by reacting with the target molecules, or a gel to separate the biological molecules and a membrane where the molecules are specifically bound and detected, similar to the Western blot method.

In other variants, the reaction surface is not of the solid support type, but can be for example another nanoparticle, a magnetic microbead, etc. The measurement can be for example carried out directly in the sample to be analyzed. If the sample is gaseous, this sample support can take the form of a closed volume to prevent dispersion of the test sample. The sample support can also take the form of a cell or cuvette, especially if the sample is in the form of a solution.

The ultrasensitive process of the invention can also be adapted for use in fluorescence-activated cell sorting (FACS) technologies. In this case, particles of the invention, coupled to targeting agents aimed at the recognition of substances making up the cell type to be analyzed, are brought into contact with the cells and the cytometry system must be adapted to include an excitation source, preferably a laser, at a wavelength adapted to the excitation of the luminescent rare-earth ions making up the nanoparticles.

The ultrasensitive process of the invention can also be adapted for use in immunocytochemistry and immunohistochemistry type technologies.

Luminescence Measurement

As mentioned above, the ultrasensitive method according to the invention more particularly implements a step (ii) of excitation of the rare-earth ions of the photoluminescent particles by an illumination device having a power of at least 50 mW, and an excitation intensity of at least 1 W/cm² and a step (iii) of detection of the luminescence emission by the particles after a single-photon absorption.

Detection Arrangement

The ultrasensitive method according to the invention is advantageously implemented with the aid of a low-sophistication, low-cost apparatus.

More precisely, it includes, in general terms:
an illumination device, preferably of the laser type, with a power of at least 50 mW and an excitation intensity of at least 1 W/cm²; and
a device for detecting the light intensity emitted by the particles.

The excitation source can also be a lamp or light-emitting diode (LED).

Figure 2:
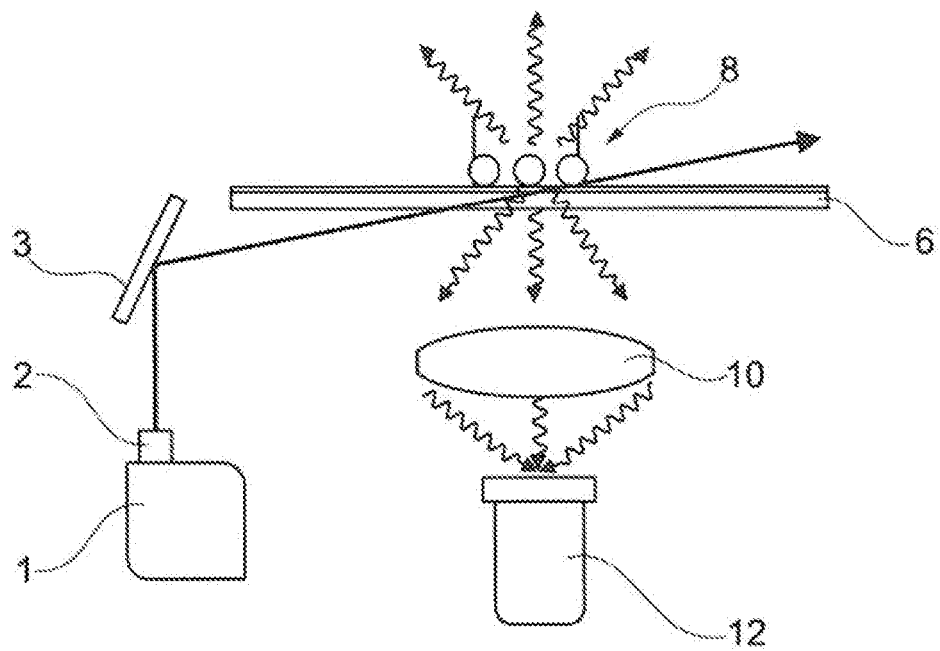

Reference will be made, hereinbelow, to FIGS. 2 and 12-13 appended hereto, which represent, in a schematic and partial manner, installations suitable for the implementation of the ultrasensitive process of the invention.

In addition, the apparatus may include a suitable support for immobilization of the substance to be analyzed from said sample, as described above.

According to a variant embodiment, the detection system according to the invention comprises a system for translating the support or the laser illumination device, making it possible to successively illuminate different localized areas of the support. Such a variant is notably used for the implementation of the method of detection of the invention for spatial multiplexing (FIG. 22), the translation system allowing the successive laser illumination of each of the predefined areas containing the substances to be analyzed in the same sample, or even in several different samples. The transmission signal is then recorded according to the illumination position of the support.

The laser illumination device can be more particularly composed of a laser source (1) with a power of at least 50 mW, in particular at least 500 mW, preferably at least 1 W, and an optical arrangement (2) for shaping the laser beam, whereby an excitation intensity of at least 1 W/cm², preferably at least 10 W/cm², can be achieved at the level of the luminescent particles.

High-power laser diodes for this embodiment, emitting notably at 465 nm, have recently become commercially available for the excitation of $Eu^{3+}$ ions.

Such an excitation intensity ensures the direct excitation of earth ions, i.e. in resonance with the electronic states of these ions, and not by excitation of the $AVO_{4(1-y)}(PO_4)_y$ matrix, or another metal oxide matrix, and subsequent energy transfer to these ions.

It was by no means obvious that these photoluminescent particles could be used as luminescent probes through direct excitation of rare-earth ions. Indeed, for most lanthanide ions, the electron transition linked to photon absorption is a so-called "forbidden" transition from one 4f electron configuration to another 4f electron configuration. Absorption is thus only slightly allowed due to a low mixing of d orbitals (the transitions d→f or f→d being allowed). The fact that the absorption-related electronic transition is "forbidden" results in a narrow spectral width of the absorption peak and a low extinction coefficient of these nanoparticles in solution.

In fact, even if photoluminescent particles consisting of a crystalline matrix doped with rare-earth ions have already been used, they are generally used through an excitation of their crystalline matrix, the latter generally absorbing much more strongly than the absorbing ions. However, as the crystalline matrix generally absorbs in the UV, the implementation of an excitation of the crystalline matrix has several disadvantages: on the one hand, lasers emitting in the UV are not very commercially available, often expensive and not very compact and, on the other hand, the excitation in the UV is likely to cause simultaneously the excitation of other biomolecules that may be present in the sample to be analyzed. In addition, absorption and scattering by the solid substrates used (glass, plastics, etc.) during the measurement are known to absorb significantly in the UV and, consequently, to induce interfering signals of high amplitude.

The laser illuminating device may also comprise an optical arrangement, in particular a system of at least one lens, arranged in the path of the laser beam so as to control the beam size at the area of the support presenting the particles associated with the substance to be analyzed.

The process of the invention, which is based on direct excitation of the rare-earth ions of the nanoparticles, makes it possible to overcome the disadvantages associated with excitation of the crystalline matrix.

Furthermore, as mentioned above, the use of high power and high excitation density according to the invention is not detrimental to the emission of luminescence by the nanoparticles implemented according to the invention which are not subject to saturation or photodegradation phenomena.

Preferably, the laser is monochromatic, with a spectral width comparable to the spectral width of the absorption peak of the luminescent lanthanide ions.

The excitation is carried out in the visible or near infra-red range.

For example, excitation can be carried out at a wavelength of 465 nm for $Y_{0.6}Eu_{0.4}VO_4$ type particles.

The optical arrangement for shaping the laser beam can conventionally include a system for collimating and reducing the size of the laser beam, for example by means of lenses, in particular two lenses, as described in Example 3. It can then be used to control the illuminated area in the area of the support presenting the particles associated with the substance to be analyzed so as to obtain an appropriate intensity (for example 10 W/cm$^2$) and an illumination whose dimensions are close to or smaller than those of the deposition spot (for example 1 mm in diameter).

The excitation in step (ii) can be more particularly carried out with a laser excitation beam oriented so as to form an angle of incidence with the vertical of the support having on its surface said particles associated with the substance to be analyzed, greater than or equal to 55° for a wide-angle illumination of the sample; in particular less than 60° in the case of a measurement carried out in aqueous medium on a glass or plastic substrate.

The use of a wide angle of incidence for the excitation laser beam reduces the volume of excited medium above the surface, thus reducing interference signals.

According to a particularly advantageous embodiment, the process of the invention involves excitation of the particles by evanescent waves, in particular by means of a total internal reflection fluorescence (TIRF) type laser illumination arrangement. This is made possible by achieving an angle of incidence of the excitation beam greater than or equal to 61°, in particular between 61° and 63°, in the case of a glass/water interface between the support and the sample to be analyzed.

It is up to the person skilled in the art to make the necessary adjustments to the detection device to obtain this incidence for evanescent wave excitation.

As shown in FIG. 13, it may notably comprise a parallelepiped with a refractive index greater than that of the reaction solution, for example, close to that of the material used for the support, allowing an angle of incidence of the excitation beam greater than the critical angle of the solid substrate/sample interface, in particular greater than or equal to 61° in the case of a glass/aqueous solution interface, so as to obtain a total reflection of the beam at the support/sample interface and an evanescent wave excitation of the particles associated with the substance to be analyzed.

According to another particularly advantageous embodiment, in the context of the use of particles with a long emission lifetime (in particular with an emission lifetime greater than or equal to 1 µs, in particular greater than or equal to 50 µs) is the use of time-resolved emission detection, in particular delayed detection of the signal emitted by the photoluminescent particles.

The person skilled in the art is able to adapt the detection system used to enable the luminescence emission to be used in a time-resolved manner.

For this purpose, a mechanical chopper (4) can be placed in the path of the incident laser beam, for example, as shown in FIG. 13.

The principle of operation of such a mechanical chopper and the methods of analysis of the resulting signal to isolate the luminescence signal from the nanoparticles are described in more detail in the following Example 3.2. The use of a mechanical chopper and a signal detection frequency of 100 kHz by the photomultiplier of the detection device makes it possible to avoid interfering fluorescence.

Such time-resolved detection thus makes it advantageous to limit the contribution to the luminescence signal of interfering species present in the sample (serum, blood, etc.) or in the solid substrates used (glass, plastic, etc.), by temporally separating interfering luminescence signals from the signal emitted by the nanoparticles, since these interfering signals generally have characteristic lifetimes of less than 1 µs, or even less than 100 ns, or even less than 10 ns.

It is understood that the various particular embodiments described above may be combined to realize different variant embodiments of the detection process according to the invention.

In particular, time-resolved detection and evanescent wave excitation of nanoparticles (TIRF arrangement) can be implemented together, as shown in FIG. 13, or not.

Thus, according to a preferred embodiment, the ultrasensitive detection process according to the invention advantageously combines an excitation of the nanoparticles by evanescent wave, in particular by means of a TIRF-type laser illumination arrangement, and a time-resolved detection of the emission, in particular a delayed detection of the emission (implementation of nanoparticles with a long emission duration, use of a chopper).

Thus, advantageously, in a process according to the invention, the lifetime of emission by the nanoparticles is greater than or equal to 1 µs, in particular greater than or equal to 50 µs, the detection of the light intensity in step (iii) comprising a time-resolved detection of the emission, in particular a delayed detection of the emission.

The combination of these two modes makes it advantageous to eliminate the emission due to particles in solution, other than those to be analyzed immobilized on the surface of the support, as well as any emission of interfering species present in the sample (serum, blood, etc.) or in the solid substrates used (glass, plastic, etc.).

Such a variant embodiment is particularly advantageous in that it dispenses with some of the conventional steps for the preparation of samples to be analyzed, and in particular rinsing and/or centrifugation steps, for example, in the case of rinsing during analysis to remove substances (molecules, proteins, peptides, etc.) contained in blood serum, other than those concerned by the analysis to be carried out (rinsing to go from phase 2 to phase 3 indicated in FIG. 1) or to remove particles which have not attached themselves to the surface of the support and remain in solution during phase 4 indicated in FIG. 1) or, for example, centrifugation steps preceding the actual analysis, as shown in FIG. 1, to remove blood cells from blood samples, which are usually time-consuming and performed manually, in particular for centrifugation steps.

Luminescence emission detection can be performed by measuring the light intensity emitted at a luminescence wavelength of the photoluminescent particles used. By way of example, in the case of the use of $Y_{1-x}Eu_xVO_4$ nanoparticles, the emitted light intensity can be measured at the luminescence wavelength of $Eu^{3+}$, i.e. 617 nm.

The light intensity detection device may comprise a single detector, in particular of the photomultiplier, photodiode, avalanche photodiode type, or a detector of the light-sensitive device array type consisting of a 2D area of sensing pixels such as a CCD or EM-CCD camera or CMOS camera. A 2D detection device allows simultaneous measurement of the emission signal of nanoparticles from different areas corresponding to different samples and/or different substances to be analyzed on the surface of the support and does not require any movement of the support or the excitation beam.

Preferably, the light intensity detection device comprises a single detector, in particular a photomultiplier, whereby a less expensive detection device can be realized.

It may also include an optical arrangement, in particular a system of at least one lens with a large numerical aperture, to focus the luminescence emission towards the detector, in particular towards the photomultiplier.

Interference filters can also be placed in the path of the emitted beam to spectrally eliminate interfering signals.

The detection can be carried out in reflection, downwards, as shown schematically in FIG. 12-a, i.e. on the side of the surface of the support receiving the laser excitation beam.

Alternatively, it can be operated in transmission, upwards, as shown schematically in FIG. 12-b. The collection of the luminescence from above is preferred in the case of an evanescent wave excitation, so as to avoid the passage of the luminescence photons through the parallelepiped allowing the realization of the evanescent wave.

Analysis of the Luminescence Measurement

The process of the invention finally comprises a step (iv) of determining the presence and/or the concentration of the substance by interpreting the luminescence measurement.

It is understood that the detection system according to the invention may additionally include any means for analyzing the luminescence emission, for example a converter for recording and evaluating the luminescence signal.

The interpretation of the luminescence measurement may be made by reference to a preestablished standard or calibration.

More precisely, the amount of the substance to be analyzed in the sample can be determined by reference to a preestablished calibration curve by means of measurements carried out with samples of known amount of said substance, preferably under conditions identical to those of the study of the sample, these identical conditions including in particular the solvent and the pH of the medium.

Advantageously, as illustrated in Example 3, the ultrasensitive process according to the invention makes it possible to detect and quantify a substance of interest in a sample in a content strictly below 10 pM, in particular below 1 pM, or even below 0.1 pM, or below 0.01 pM (i.e. 10 fM).

In fact, it allows a detection at least 10 times, in particular at least 100 times or even 1000 times more sensitive than the ELISA-type enzyme immunodetection method, using the same recognition and targeting antibodies.

In Vitro Diagnostic Kit

The invention also concerns, according to another of its aspects, an in vitro diagnostic kit, comprising at least:
  luminescent particles consisting, in whole or in part, of a photoluminescent inorganic nanoparticle as defined above,
  said particles being surface functionalized with chemical groups, for example carboxyl, amino, thiol, aldehyde or epoxy groups, provided by molecules, for example citric acid or polyacrylic acid, and/or coupled to molecules, for example streptavidin, said chemical groups or molecules being capable of allowing coupling of said particles with a targeting agent for the substance to be analyzed; or
  said particles being already coupled to at least one targeting agent for the substance to be analyzed;
  a detection and/or quantification system comprising at least:
    a laser illuminating device with a power of at least 50 mW or at least 500 mW, and an optical arrangement for shaping the laser beam so that an excitation intensity of at least 1 W/cm$^2$, preferably at least 10 W/cm$^2$, is obtained at the sample level
    a device for detecting the light intensity emitted by the particles.

The in vitro diagnostic kit according to the invention may additionally include a suitable support for immobilization of the substance to be analyzed of said sample, as described above.

This may be a support whose surface has been passivated and functionalized with a targeting agent for the substance to be detected/quantified, for example with a first antibody, as described above.

In a first variant embodiment, the in vitro diagnostic kit according to the invention may comprise photoluminescent particles according to the invention already coupled to a targeting agent, in particular to antibodies, called "detection antibodies" to distinguish them from capture antibodies immobilized at the level of the support.

The particles coupled to the targeting agent can be obtained as described above.

In another variant embodiment, the kit may comprise particles which are not coupled to a targeting agent, from which the user or practitioner may prepare the particles coupled to one or more targeting agents for implementation in the ultrasensitive method according to the invention.

According to a particular embodiment, the in vitro diagnostic kit according to the invention may thus comprise several containers comprising, in an isolated manner, said uncoupled particles on the one hand and one or more targeting agents on the other.

Alternatively, the in vitro diagnostic kit according to the invention does not include a targeting agent, the user or practitioner being able to obtain the targeting agent, for example biotinylated, of his choice, separately by any competent supplier.

The preparation of the particles coupled to the targeting agents involves in the context of this variant embodiment the mixing of the uncoupled particles according to the invention with the targeting agent, in concentration ratios predetermined by the contents of the containers in the case of the presence of the targeting agent within the in vitro diagnostic set according to the invention, or determined by the user, for example as described in Example 1.

The particles not coupled to a targeting agent used in an in vitro diagnostic kit according to the invention may be notably particles coupled to molecules, for example streptavidin, capable of allowing the coupling of said particles with a targeting agent, for example biotinylated, for example a biotinylated antibody.

Other pairs of molecules can be envisaged for this type of coupling, for example hapten/antibody, antigen/antibody, peptide/antibody, such as digoxygenin (DIG)/anti-DIG antibody, sugar/lectin and polynucleotide/polynucleotide complement.

Alternatively, the particles not coupled to a targeting agent used in an in vitro diagnostic kit according to the invention may in particular be particles surface functionalized with chemical groups capable of allowing the coupling of said particles with a targeting agent for the substance to be analyzed, for example carboxyl, amino, thiol, aldehyde or epoxy groups, provided by molecules, such as for example citric acid or polyacrylic acid.

As examples, the particles may be functionalized with citrate or polyacrylic acid, the preparation of the particles coupled with the targeting agents involving the activation of carboxylic functions, as described in Example 1, followed by mixing the particles not coupled with the targeting agent.

It is understood that the functionalization of the surface of nanoparticles may have more than one layer. For example, as mentioned above, the particles of the invention may comprise a layer of preparation or stabilization of the surface of the nanoparticles, such as a layer of silica, followed by a layer of functionalization by active chemical groups, such as a layer consisting of aminopropyltriethoxysilane (APTES).

The examples and figures presented below are given only by way of non-limiting illustration of the invention.

FIGURES

FIG. 1: Schematic representation of the principle of detection of biomolecules: surface functionalized with a capture antibody (phase 1); contact of the sample to be analyzed (phase 2), washing (phase 3) and association of the photoluminescent particles coupled with a targeting agent (here an antibody) with the substance immobilized on the surface of the support followed by washing to remove the non-immobilized particles (phase 4);

FIG. 2: Schematic representation of a detection device according to the invention, composed notably of a laser source 1, a system for collimating and reducing the size of the laser beam 2, a mirror 3 for directing the laser beam, a support 6 for the samples, and a system for detecting the emitted photons comprising a lens with a large numerical aperture 10 and a photomultiplier 12;

FIG. 3: Transmission electron microscopy (TEM) images of the nanoparticles obtained in Example 1 (Scale bar: 60 nm (FIG. 3a) and 5 nm (FIG. 3b), respectively);

FIG. 4: Histogram of nanoparticle size determined from TEM images for a set of about 300 nanoparticles according to Example 1;

FIG. 5: X-ray diffractograms obtained for nanoparticles synthesized according to Example 1 (black line), and 3 (gray line);

FIG. 6: Schematic representation of the nanoparticles of the invention functionalized with citrate (FIG. 6a) or with polyacrylic acid (PAA) (FIG. 6b). For clarity, only one citrate or PAA molecule is shown. It is understood that each nanoparticle may have many citrate or PAA molecules on its surface.

Figure 7:
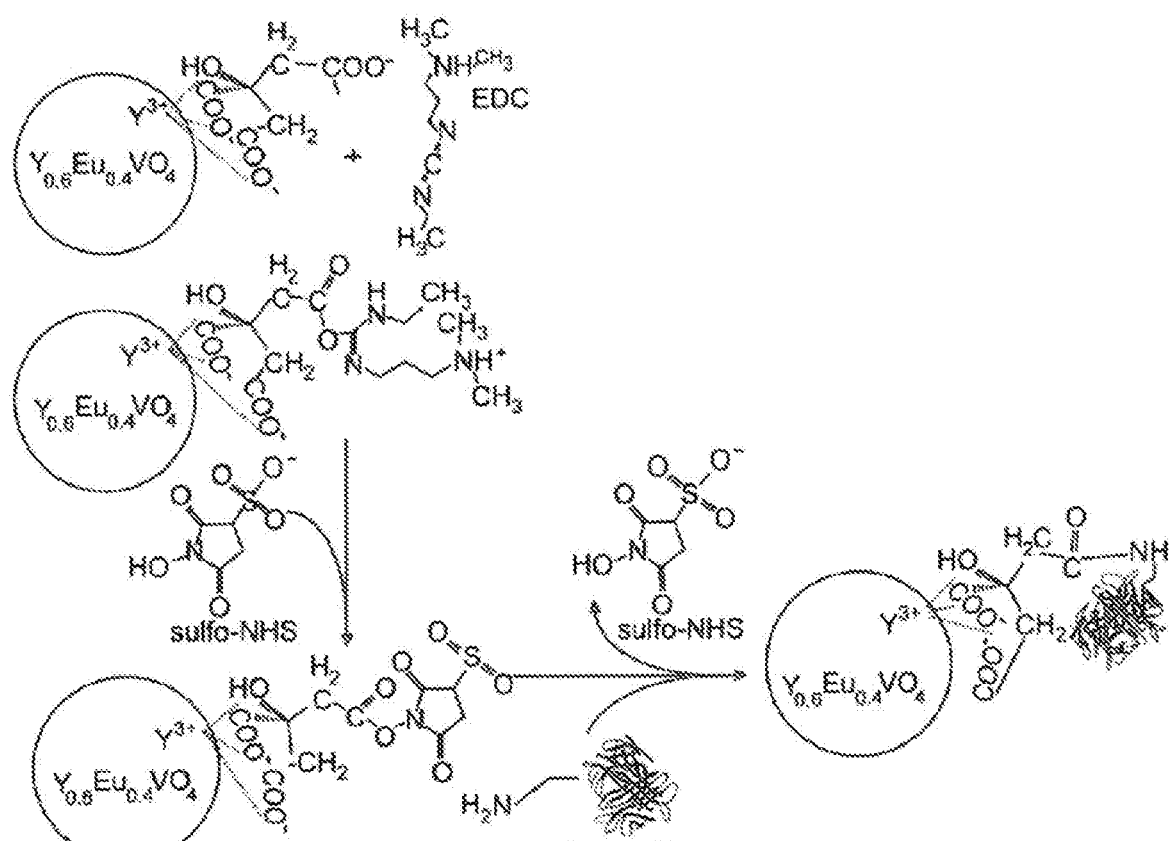
Figure 8:
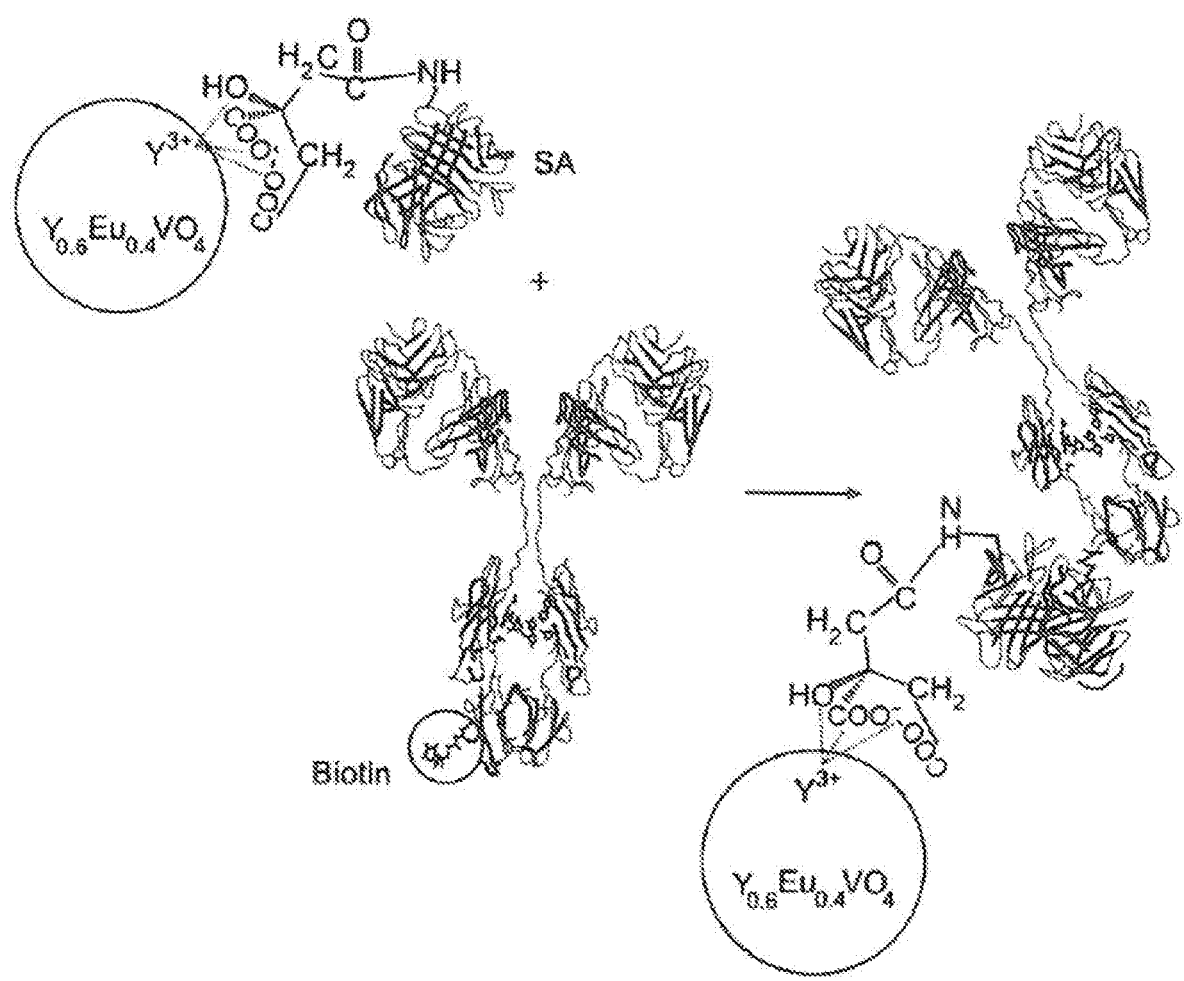
Figure 9:
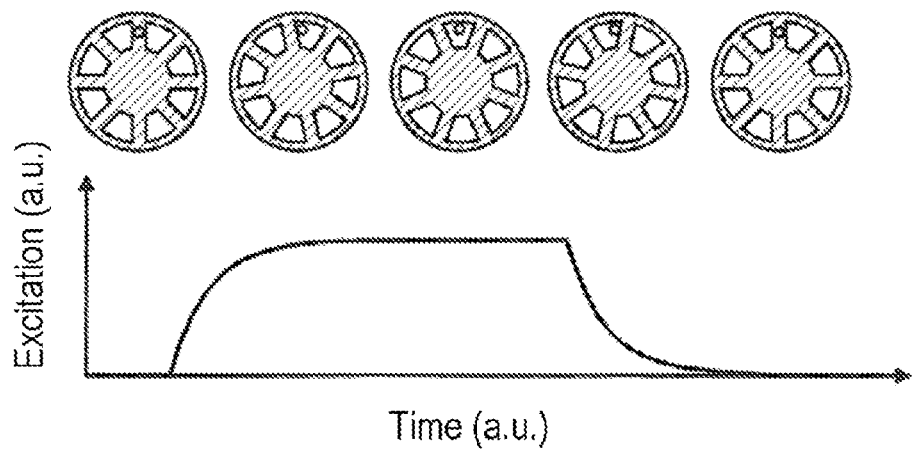
Figure 14A:
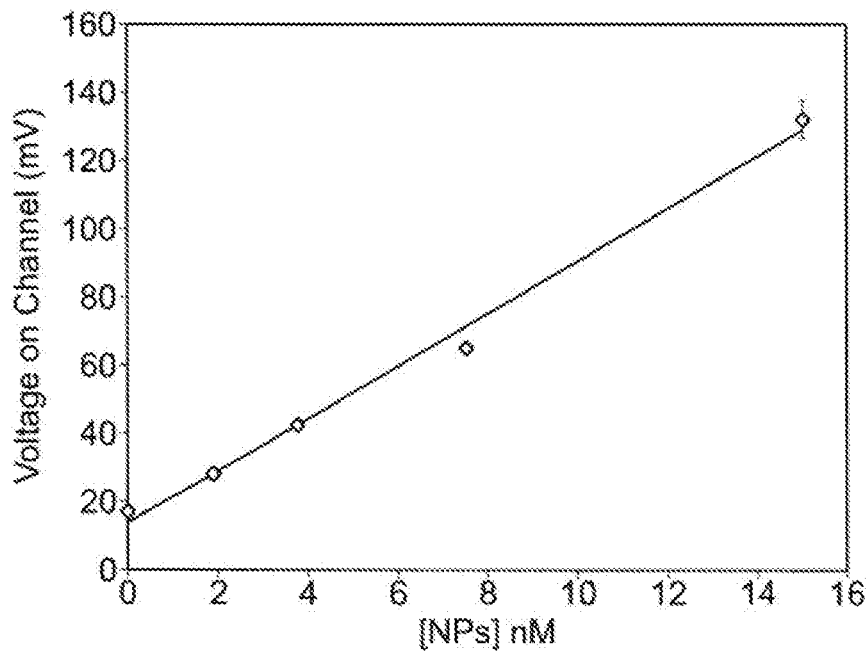
Figure 14B:
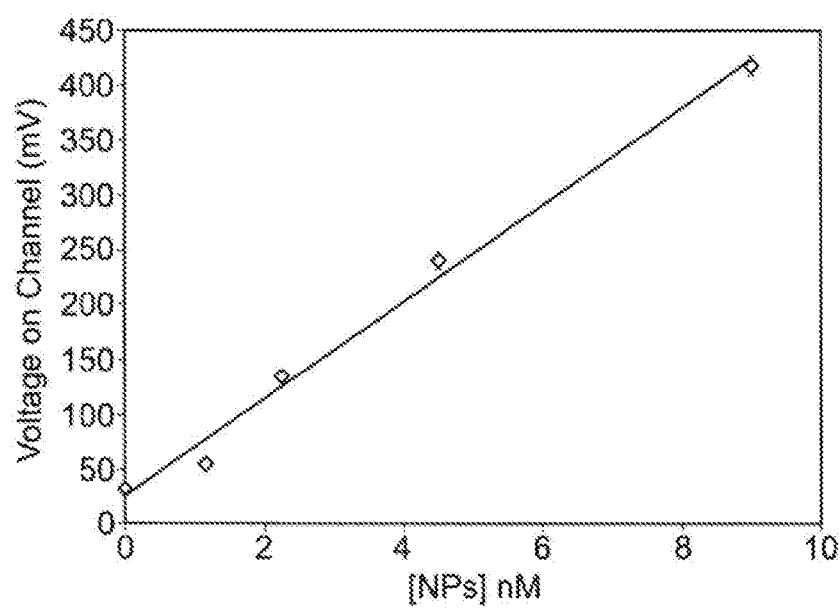
Figure 15:
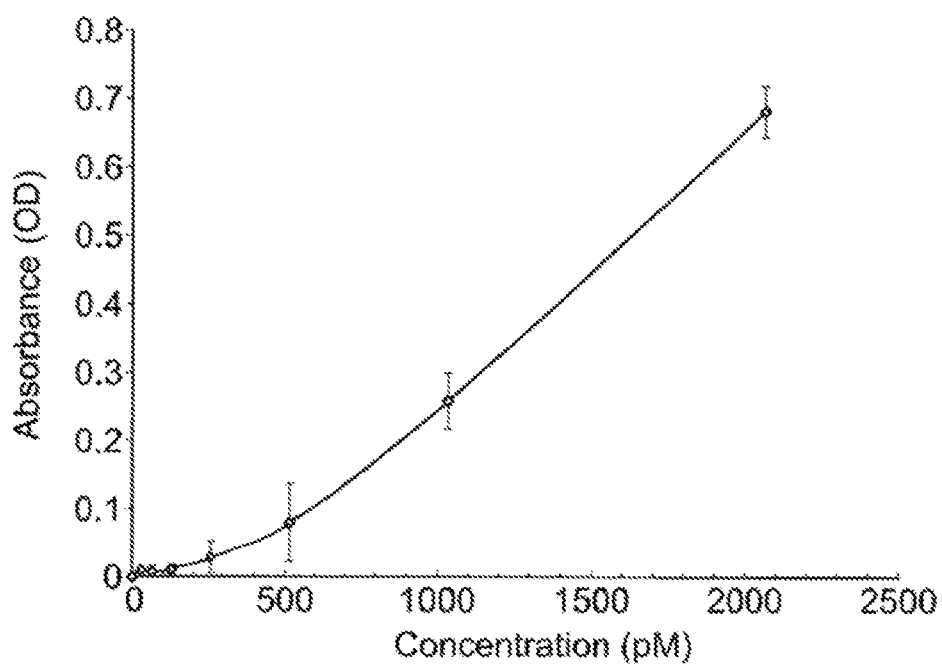
Figure 16:
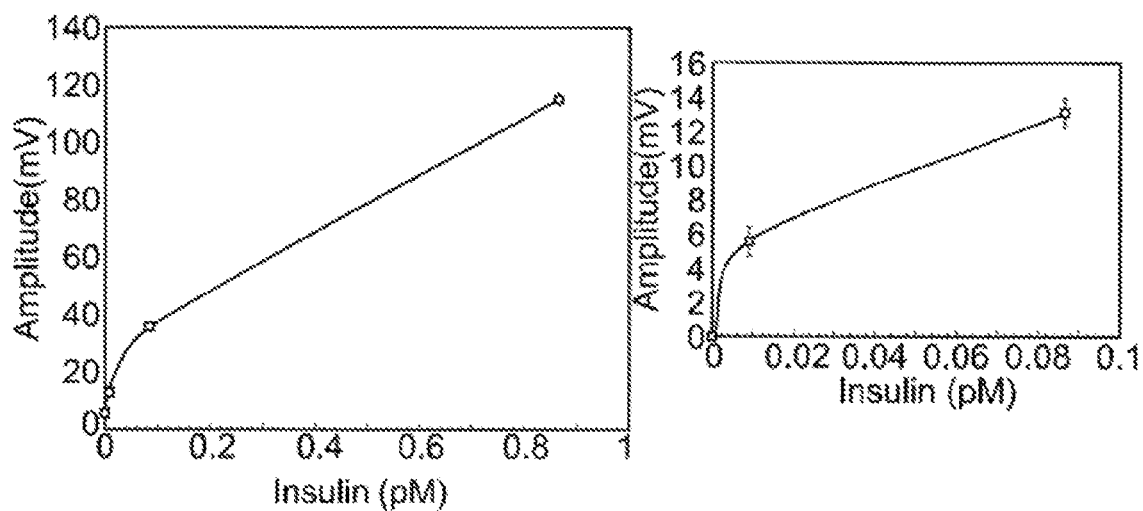
Figure 17:
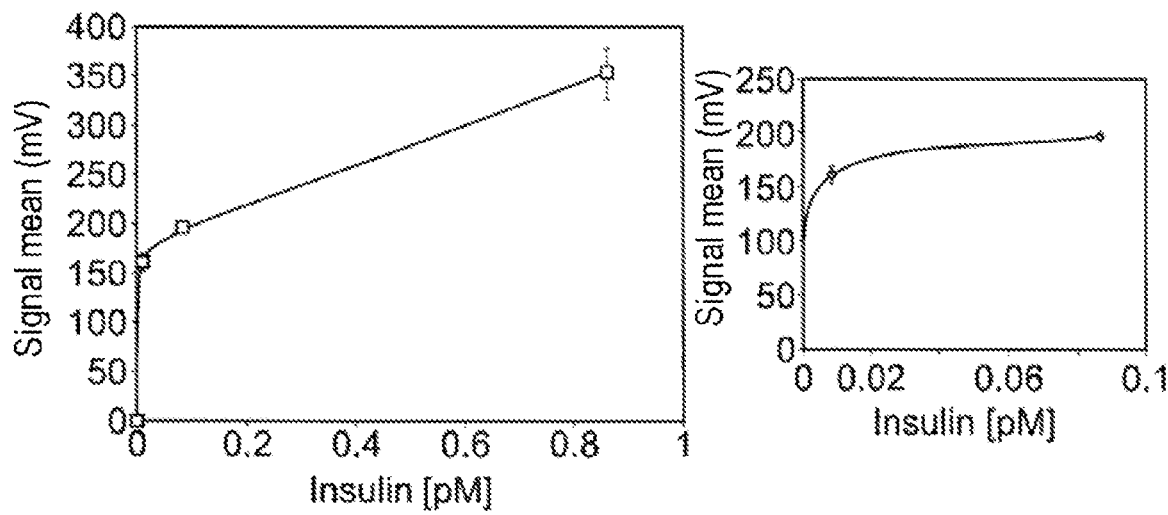
Figure 18:
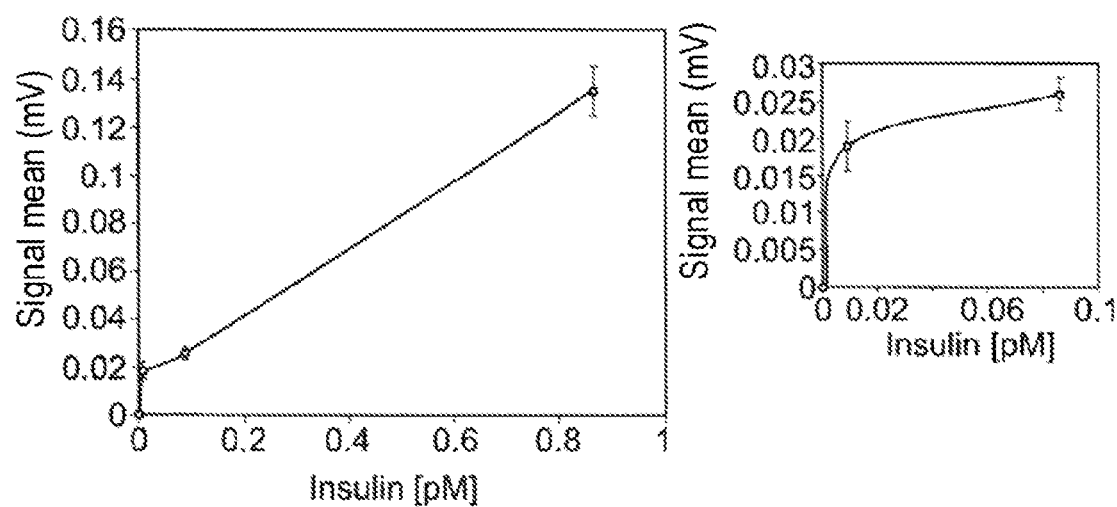
Figure 19:
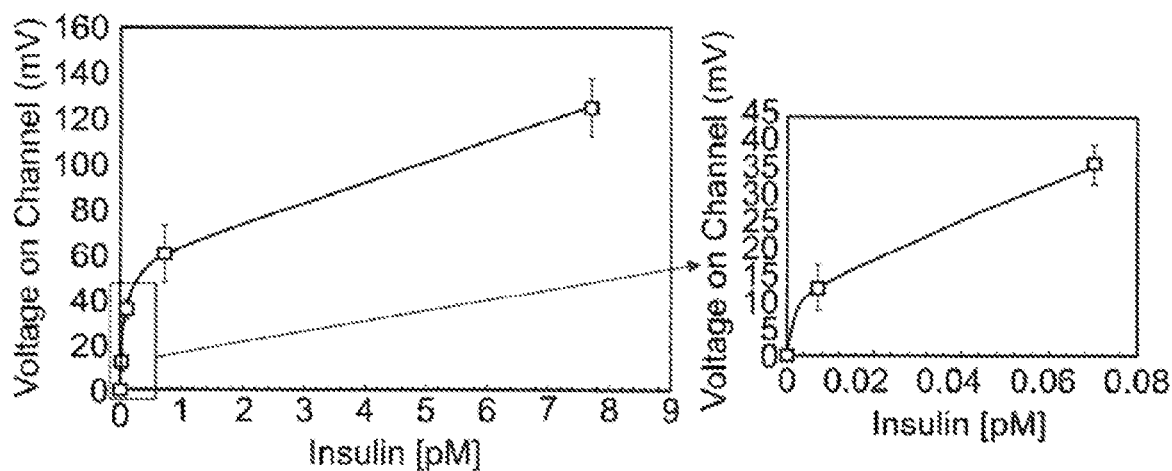
Figure 20:
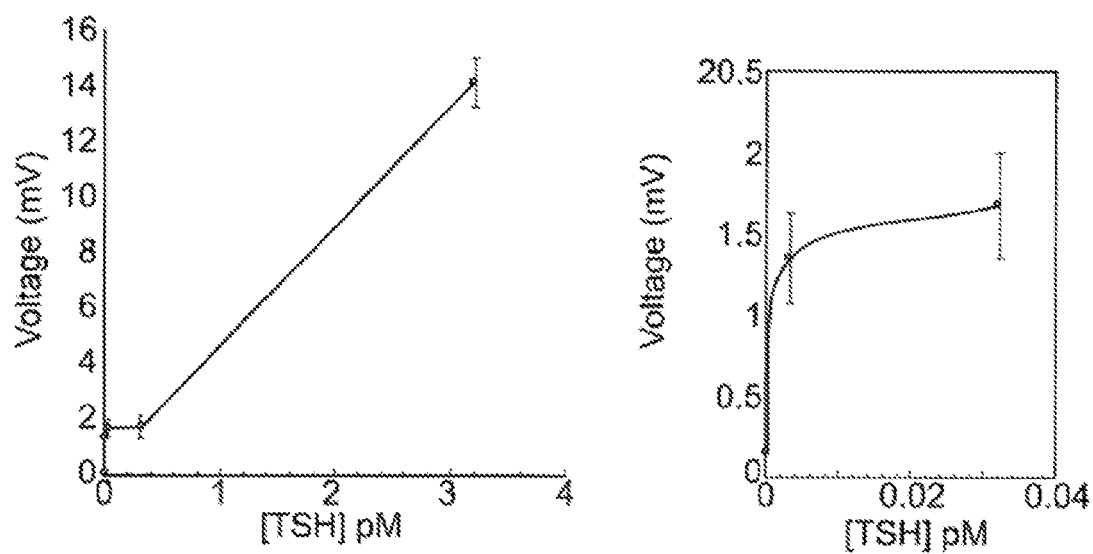
Figure 21:
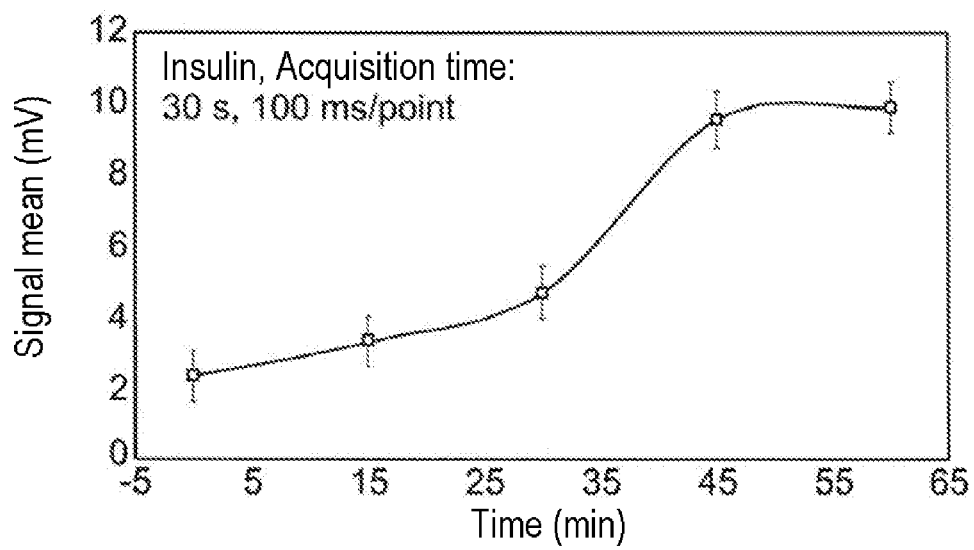
Figure 23:
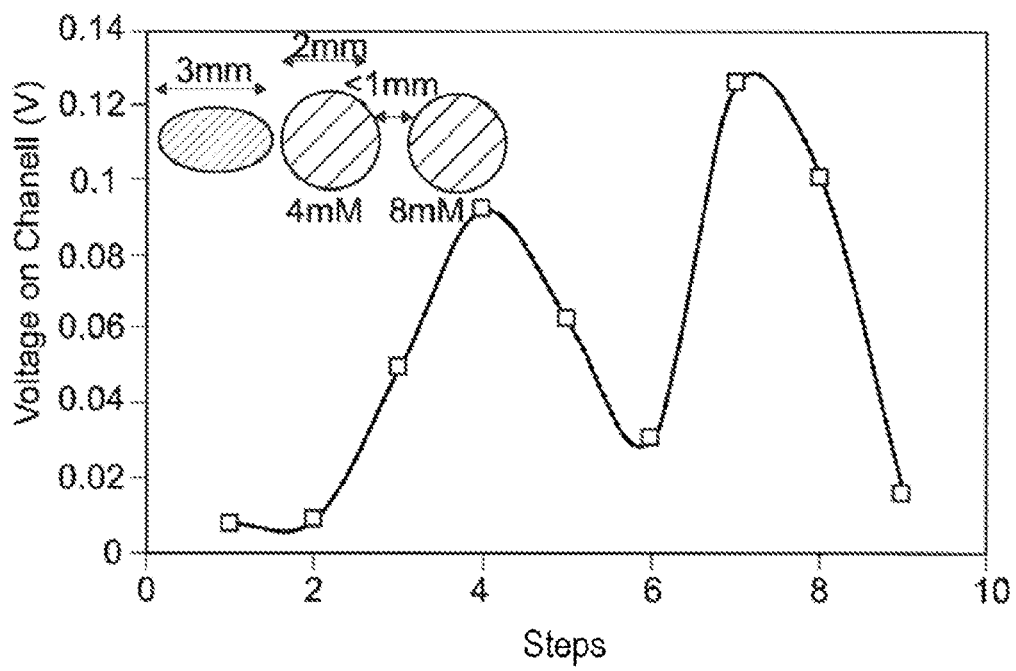

FIG. 7: Schematic representation of the reactions for the coupling of a nanoparticle according to the invention with streptavidin, according to Example 1;

FIG. 8: Schematic representation of the coupling of streptavidin-coupled nanoparticles with a biotinylated antibody;

FIG. 9: Schematic representation of the use of a rotating mechanical chopper to obtain periodic illumination, and time profile of the excitation intensity obtained. In the case of the time profile shown, the resulting excitation intensity increases or decreases gradually due to the finite beam size and the time required for the mechanical chopper blade to expose or hide the entire excitation beam;

FIG. 10: Signals obtained in evanescent wave excitation mode (TIRF) after half a closing half-cycle of the chopper with pure water (a), nanoparticles (3 mM vanadate ion concentration drop) in water (b) and in serum (c): raw signal (FIG. 10-a) and luminescence signal in delayed detection (detection restricted to 150 µs after the start of excitation beam blanking) (FIG. 10-b);

FIG. 11: Left: luminescence modelling with a two-level system. Right: averaged signal emitted by nanoparticles ($Y_{0.6}Eu_{0.4}VO_4$) deposited on a slide, collected during 500 opening-closing cycles (circles) of the chopper, in comparison with its adjustment (solid line), determining the quantity of nanoparticles. Results obtained in HI-LO excitation mode (i.e. the excitation beam forming a wide angle with the vertical on the sample support);

FIG. 12: Schematic representation of a detection device according to the invention, with downward emission detection (FIG. 12-a) and upward emission detection (FIG. 12-b);

FIG. 13: Schematic representation of a detection device according to the invention, with laser beam chopper 4 and excitation in total internal reflection (using a Plexiglas 13 parallelepiped with a refractive index greater than or equal to that of the material serving as sample support);

FIG. 14: Calibration curve of the detection device according to variant 2, with chopper and with evanescent wave excitation, following the protocol described in Example 3.2.ii (FIG. 14-a); and according to variant 3, without chopper and without evanescent wave excitation, following the protocol described in Example 3.2.ii. (FIG. 14-b);

FIG. 15: Detection of recombinant insulin in solution by an ELISA kit (ABCAM item ab100578). The detection limit specified by the kit supplier is 9 pM (50 pg/mL);

FIG. 16: Detection of recombinant insulin in solution up to concentrations of 9 fM (0.05 pg/mL) with variant 1 of the detection device described in Example 3 (acquisition time: 30 s; signal readout every 100 ms). In the insert, the signal corresponding to a concentration equal to zero has been subtracted;

FIG. 17: Detection of recombinant insulin in solution up to concentrations of 9 fM (0.05 pg/mL) with variant 2 of the detection device described in Example 3, without chopper and without evanescent wave excitation (acquisition time: 1 s; signal readout every 10 µs);

FIG. 18: Detection of recombinant insulin in solution up to concentrations of 9 fM (0.05 pg/mL) with variant 2 of the detection device described in Example 3, with chopper and with evanescent wave excitation (acquisition time: 1 s; signal readout every 10 µs);

FIG. 19: Detection of insulin in different serum samples on a multi-well plate according to variant 1 of the detection device described in Example 3 (acquisition time: 30 s; signal readout every 100 ms);

FIG. 20: Detection of recombinant TSH in solution up to concentrations of 3.2 fM according to variant 1 of the detection device described in Example 3 with chopper (acquisition time: 1 s; signal readout every 10 µs);

FIG. 21: Change in the detected luminescence signal according to variant 1 of the detection device as a function of the incubation time with antibody-nanoparticle conjugates according to Example 4;

FIG. 22: Schematic diagram of the principle of spatial multiplexing;

FIG. 23: Schematic representation of the two nanoparticle "spots" formed according to Example 5, and the luminescence signal detected for the different locations;

FIG. 24: Schematic representation of the detection and quantification of DNA/RNA using particles according to the invention coupled with single-stranded DNA. Single-stranded DNA partially complementary to the strand to be detected is fixed on a support. Then the sample containing the DNA or RNA to be detected is incubated with the functionalized support (left). After rinsing, the particles coupled with single-stranded DNA, partially complementary to the unpaired part of the DNA or RNA to be detected, are incubated with the support (middle). After rinsing, only the nanoparticles immobilized on the surface of the support after pairing with the DNA or RNA to be detected are present (right). They can be detected and quantified as described in the text.

FIG. 25: Schematic representation of the detection and quantification of DNA/RNA using particles according to the invention coupled with streptavidin molecules.

(a) This DNA or RNA detection/quantification variant uses a single-stranded "recognition" DNA coupled to a streptavidin molecule at each end to be attached to the detection support, the single-stranded DNA or RNA to be detected and a single-stranded DNA partially complementary to the DNA coupled to a biotin molecule. The streptavidin-coupled DNA is, with its non-complementary part to the biotin-coupled DNA, at least partially complementary to the DNA to be detected.

(b) The surface of the support is passivated with PEG and functionalized with biotin. DNA coupled with streptavidin at each end attaches to the surface of the functionalized support. Then, following incubation with the DNA to be detected, it matches the DNA immobilized on the surface of the support. After rinsing, the biotins remaining on the surface are passivated with streptavidin. The "detection" DNA attached to a biotin is incubated with the surface and pairs with the complementary part of the DNA coupled to two molecules of streptavidin.

(c) After rinsing, the particles of the invention coupled to streptavidin molecules are incubated with the surface and bind to the single stranded "detection" DNA via interaction with biotin.

After rinsing, particles immobilized on the surface can be detected and quantified as described in the text. It is also possible to use "recognition" DNA coupled to a single streptavidin molecule at one end. In this case, the "recognition" DNA is attached to the surface of the support by only one of its two ends, as in variant 1.

Figure 26A:
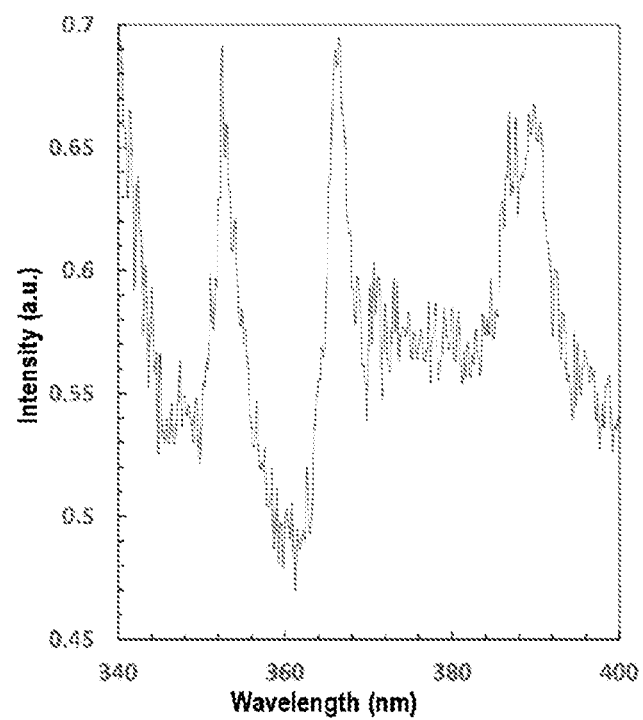
Figure 26B:
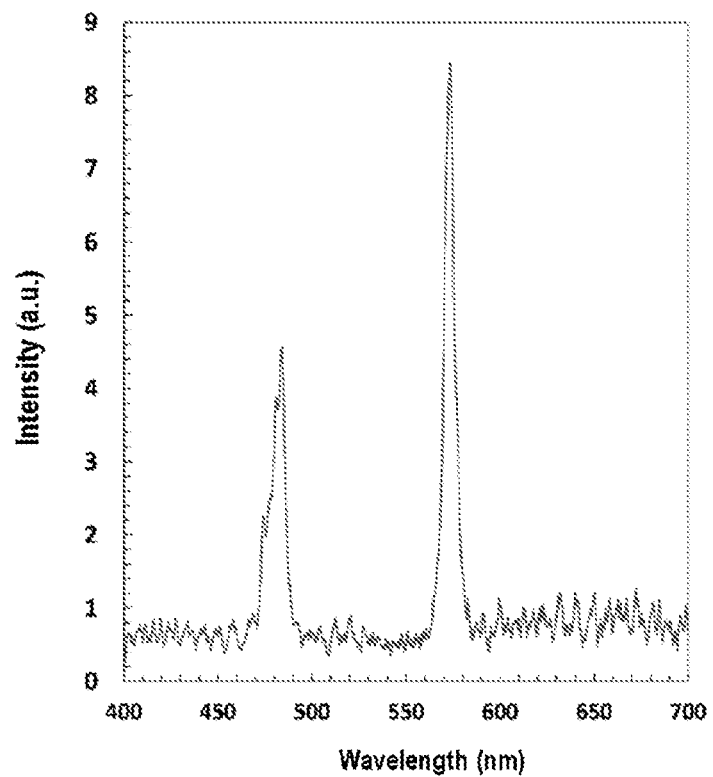

FIG. 26: Excitation and emission spectra of the nanoparticle solution $YVO_4$:Dy 3% prepared in Example 6: excitation spectrum in the region of direct absorption of $Dy^{3+}$ ions for detection at $\lambda=572$ nm (FIG. 26-$a$) and emission spectrum for excitation at $\lambda=278$ nm corresponding to the excitation of the vanadate matrix (FIG. 26-$b$).

Figure 27A:
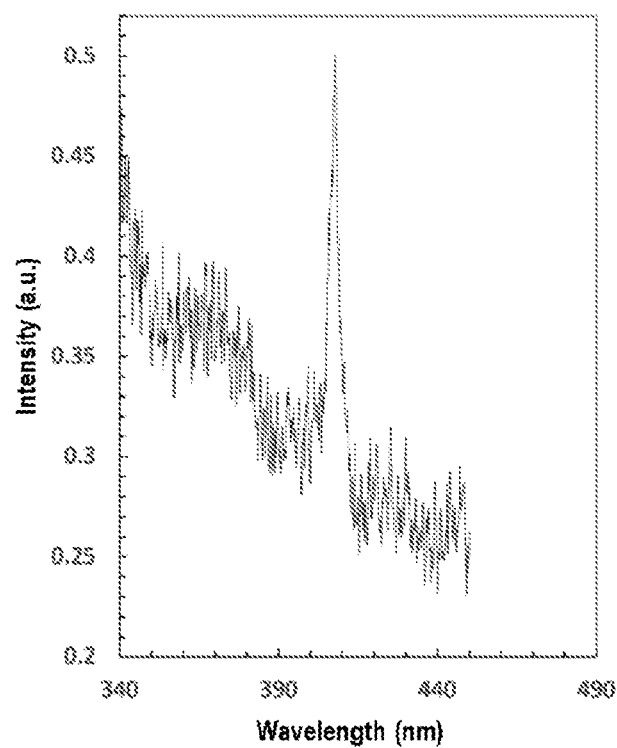
Figure 27B:
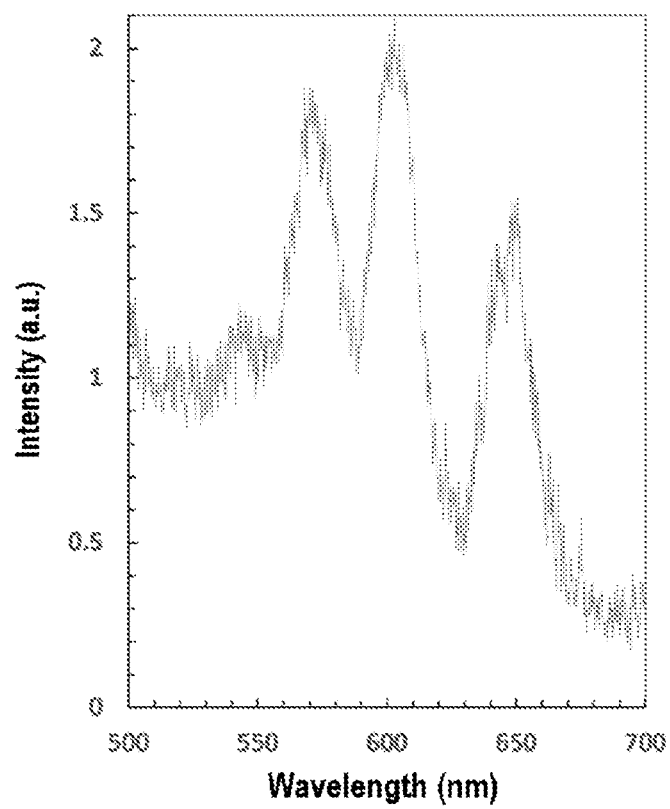

FIG. 27: Excitation and emission spectra of the nanoparticle solution $YVO_4$:Sm 3% prepared in Example 7: excitation spectrum in the region of direct absorption of $Sm^{3+}$ ions for detection at $\lambda=600$ nm (FIG. 27-$a$) and emission spectrum for excitation at $\lambda=278$ nm corresponding to the excitation of the vanadate matrix (FIG. 27-$b$).

EXAMPLES

Example 1

Preparation of Luminescent Particles 1.1. Synthesis of $Y_{0.6}Eu_{0.4}VO_4$ Nanoparticles Ammonium metavanadate $NH_4VO_3$ is used as a source of metavanadate $VO^{3-}$ ions, orthovanadate $VO_4^{3-}$ being obtained in situ by reaction with a base, in this case tetramethylammonium hydroxide, $N(CH_3)_4OH$. Yttrium and europium nitrates were used as sources of $Y^{3+}$ and $Eu^{3+}$ ions.

A 10 mL aqueous solution of 0.1 M $NH_4VO_3$ and 0.2 M $N(CH_3)_4OH$ (solution 1) is freshly prepared.

A volume of 10 mL of another solution of $Y(NO_3)_3$ and $Eu(NO_3)_3$ with 0.1 M ions ($Y^{3+}+Eu^{3+}$) is added dropwise by means of a syringe plunger to solution 1 at a flow rate of 1 mL/min.

The molar concentration ratio between $Y(NO_3)_3$ and $Eu(NO_3)_3$ is selected as a function of the desired ratio between $Y^{3+}$ and $Eu^{3+}$ ions in the nanoparticle, typically the molar ratio $Y^{3+}$:$Eu3^+$ is 0.6:0.4.

As soon as $Y(NO_3)_2$/$Eu(NO_3)_3$ solution is added, the solution becomes diffusive and appears milky/white without precipitate formation. Synthesis continues until $Y(NO_3)_2$/$Eu(NO_3)_3$ solution is fully added.

The final 20 mL solution must now be purified to remove excess counterions. To do this, centrifugations (typically three) at 11 000 g (Sigma 3K10, Bioblock Scientific) for 80 minutes each followed by redispersion by sonication (Bioblock Scientific, Ultrasonic Processor operating at 50% at 400 W power for 40 s) are used until a conductivity strictly below 100 µS·cm$^{-1}$ is reached.

Conductivity is measured using a chemical conductivity meter.

The synthesis of the nanoparticles $Y_{0.6}Eu_{0.4}VO_4$ on the surface of which the tetramethylammonium cations are immobilized can be schematically summarized as follows:

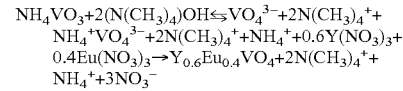

Two synthesis tests ("synthesis 1" and "synthesis 2") are carried out.

Result

Visual observation of the nanoparticle solution according to the invention, after being left to rest for 16 hours in a vial, shows a uniformly diffusing solution.

The final solution remains very stable in water, even after several months in the final pH of the synthesis (about pH 5). The solution remains stable even in the synthesis medium (before removal of excess counterions), which has a high ionic strength (>0.1 M).

The zeta potential of the nanoparticles is determined with a DLS-Zeta Potential device (Zetasizer Nano ZS90, Malvern). The results of the measured zeta potentials for nanoparticles from both syntheses are summarized in Table 1 below.

TABLE 1

|  | Synthesis 1 | Synthesis 2 |
| --- | --- | --- |
| Conductivity (µS/cm) | 93 | 80 |
| pH | 4.81 | 4.96 |
| Zeta potential ζ | −33.3 | −34.6 |

For transmission electron microscopy (TEM) observations, dilute solutions of nanoparticles are deposited on a carbon grid. The observations are made using a Philips CM30 microscope operating at 300 kV with a resolution of 0.235 nm.

The observation of nanoparticles by TEM (FIG. 3) shows that the nanoparticles have an elongated ellipsoid shape. Nanoparticle dimensions are determined from TEM images for a set of about 300 nanoparticles (FIG. 4). The nanoparticles of the invention have a major axis length, denoted a, of between 20 and 60 nm, with an average value of about 40 nm, and a minor axis length, denoted b, of between 10 and 30 nm, with an average value of about 20 nm.

The MET images (FIG. 3) do not distinguish between crystal planes, which is probably due to the fact that the nanoparticle is made up of several crystallites smaller than the size of the nanoparticle. The predominantly crystalline and polycrystalline nature of nanoparticles is confirmed by X-ray diffraction experiments.

The X-ray diffractogram obtained using a Philips X-pert diffractometer with the copper $K_{\alpha 1}$ line (=1.5418 Å) is shown in FIG. 5. The diffracted intensity is recorded using an X'Celerator area detector (PANalytical).

The coherence length in a crystallographic direction and thus the average size of the crystallites constituting the nanoparticle in this crystallographic direction can be estimated from the width of the peaks in the RX diffractogram by applying the Scherrer formula. The coherence length values obtained for the different crystallographic directions are between 3 and 40 nm. Since the coherence length in at least one crystallographic direction is smaller than the size of the nanoparticle in that direction, it can be deduced that nanoparticles are imperfectly crystalline (polycrystallinity, defects or porosity). In the (200) direction (FIG. 3, peak at $2\theta \cong 25°$), the coherence length is 10.2 nm, slightly shorter than the coherence length for the nanoparticles in Example 3 (11.1 nm).

1.2. Coupling of the Nanoparticles with Streptavidin Protein i.a. Grafting of Citrate onto the Surface of Nanoparticles After the synthesis of the nanoparticles according to Example 1.1. 250 µL of $Y_{0.6}Eu_{0.4}VO_4$ particles with a concentration of 5 mM vanadate ions are removed, the nanoparticle solution is centrifuged at 17 000 g for 30 minutes.

The pellet is removed and dispersed in 1 mL of a distilled water solution containing citrate ion (0.2 M concentration).

The solution is then sonicated for 5 minutes in an ice bath, centrifuged at 17 000 g for 30 minutes and the pellet is recovered and redispersed in distilled water containing citrate ion (0.2 M concentration). This step is repeated three times.

After this grafting, the particles are dispersed in distilled water, a solvent in which they are stable.

The functionalization of the nanoparticles by citrate can be replaced by functionalization by PAA (for example with a degree of polymerization between 3 and 10 000), using a PAA salt, such as a sodium or ammonium salt.

i.b. Grafting of PAAs onto the Surface of Nanoparticles

After the synthesis of the nanoparticles according to Example 1.1, 500 µL of $Y_{0.6}Eu_{0.4}VO_4$ particles with a concentration of 10 mM are removed and the nanoparticle solution is centrifuged at 17 000 g for 30 minutes.

The pellet is removed and dispersed in 1 mL of a distilled water solution containing 1800 Da molecular weight PAA (75 mM concentration).

The solution is then sonicated for 5 minutes, centrifuged at 17 000 g for 30 minutes and the pellet is recovered and redispersed in distilled water containing 1800 Da molecular weight PAA (75 mM concentration). This step is repeated three times.

After grafting, the particles are dispersed in distilled water, a solvent in which they are stable.

FIG. 6 schematically shows the nanoparticles of the invention functionalized with (a) citrate and (b) polyacrylic acid.

ii. Coupling Nanoparticles with Streptavidin

Nanoparticles (NPs) grafted with citrate ions or PAA are centrifuged at 16 000 g for 1 hour and the pellet is then recovered.

The coupling of the nanoparticles grafted on the surface by citrate with streptavidin is carried out according to the following protocol:

1. Freshly prepare a mixed solution of EDC[1]/Sulfo-NHS[2] (concentration 30 and 30 mg/mL, respectively) in MES buffer[3] (pH 5-6).
2. Disperse by sonication (ultrasonic bath) the pellet of NPs in 250 µL of the solution prepared in step 1. Since centrifugation losses are low, the concentration of vanadate ions remains around 5 mM, giving a nanoparticle concentration of 48 nM.
   (The vanadate concentration of the nanoparticle solutions was determined by dissolving the particles in an acidic medium followed by a colorimetric determination of the vanadate ion concentration as described in reference [34] Abdesselem et al., ACS Nano 8, 11126-11137 (2014). The molar concentration of nanoparticles was determined from the concentration of vanadate ions, as described in reference [35].
3. Prepare a 100 nM solution of streptavidin (SA) in pH 7.4 phosphate buffer with 10 mM NaCl. Dilute the streptavidin solution to a concentration determined by the number of grafted proteins per desired nanoparticle (for a streptavidin:NP ratio of 1:1, 5:1 and 10:1, choose concentrations of 4.8 nM, 24 nM and 48 nM, respectively). Preferably choose a ratio of at least 20:1, i.e. a SA concentration of 96 nM. Add 250 µL of this solution to the nanoparticle solution.
4. Allow to incubate for 2-4 hours at room temperature with stirring.
5. Add 1 mL of PBST[4] and vortex.
6. Centrifuge at 17 000 g for 30 min and recover the pellet to remove non-NP-coupled proteins. Completely remove the supernatant. Redisperse the protein-coupled NPs in 1 mL of PBST and sonicate in an ultrasonic bath. Repeat this step twice.
7. Recover protein-coupled NPs in 250 µL of PBS[5] with 1% BSA[6].
8. Store at 4° C. for immediate use or aliquot and store at −80° C.

The coupling of nanoparticles with streptavidin is shown schematically in FIG. 7.

Equipment used for functional testing:

[1] N-(3-Dimethylaminopropyl)-N'-ethylcarbodiimide hydrochloride (EDC) (Sigma, cat # E1769).
[2] N-Hydroxysulfosuccinimide sodium salt (Sulfo-NHS) (Sigma, cat #56485).
[3] 2-(N-Morpholino)ethanesulfonic acid (MES) (10 mM, pH 5-6).
[4] Phosphate buffered saline pH 7.4 (10 mM NaCl)+0.05% Tween 20 (PBST).
[5] Bovine serum albumin (BSA) (Sigma, cat # A3059).
[6] Phosphate buffered saline (PBS) (pH 7.4, 10 mM NaCl).

The number of streptavidin (SA) molecules per nanoparticle (NP), denoted R, characterized at the end of the coupling protocol, is determined by the determination of streptavidin by the so-called BCA method, according to the protocol detailed above.

Protocol for the Characterization of the Streptavidin:Nanoparticle (SA:NP) Ratio i. Determination of SA by the BCA Method Principle In an alkaline medium, proteins reduce $Cu^{2+}$ to Cu. The salt of bicinchoninic acid (BCA) forms a colored complex with $Cu^{2+}$ ions. This complex is quantifiable due to its absorption at 562 nm.

Procedure

BCA test kit from ThermoFisher (Pierce™ BCA Protein Assay Kit Cat. No. 23225)

Preparation of the $Cu^{2+}$/BCA test reagent according to the ThermoFisher kit protocol.

Preparation of SA for the calibration curve. For the calibration curve, the test is performed three times.

TABLE 2

Streptavidin concentration of calibration solutions

| Tubes | Final SA concentration (µg/mL) |
|---|---|
| A | 2000 |
| B | 1500 |
| C | 1000 |
| D | 750 |
| E | 500 |
| F | 250 |
| G | 125 |
| H | 25 |
| I | 0 = blank |

The procedure is as follows:

Take a 96-well plate. Place 25 µL of each tube of standard A-I (of known concentration of SA) or nanoparticle conjugated proteins to be assayed into the corresponding wells.

Add 200 µL of the $Cu^{2+}$/BCA test reagent to each well. Homogenize, cover and incubate 30 min at 37° C.

Read absorbances (A) at 562 nm as a function of the final concentration taking into account the dilution. Establish the calibration relationship A=f (SA concentration in µg/mL) by linear regression.

The concentration of the proteins conjugated to the nanoparticles to be assayed is deduced from the linear regression equation obtained from the calibration curve.

ii. Characterization of the SA:NP Ratio

The mass concentration of streptavidin obtained with the BCA test is converted to a molar concentration using the following formula:

$$[SA]_{molar}(\text{moles/L}) = \frac{[SA]\text{mass (g/L)}}{\text{Molar mass (g/mole)}}$$

To obtain the ratio (R) of the number of SA:NPs, we finally apply the following equation:

$$R = \frac{[SA]\text{molar}}{[NPs]\text{molar}}$$

Table 3 below summarizes the values obtained for the different concentration ratios between the streptavidin solution and the starting nanoparticle solution.

TABLE 3

Characterization of nanoparticle-streptavidin coupling for different concentration ratios between streptavidin solution and nanoparticle solution.

| Concentration ratios between streptavidin solution and nanoparticle solution | 1:1 | 5:1 | 10:1 |
|---|---|---|---|
| Determined number of streptavidin molecules per nanoparticle after coupling | 0.97 | 3.8 | 9.29 |

As can be seen from the results presented in Table 3, the number of streptavidin molecules per nanoparticle after coupling is of the same order as the concentration ratio in the initial solutions, thus indicating very good coupling efficiency.

1.3. Coupling Streptavidin-Coupled Nanoparticles (Nanoparticles-SA) with Biotinylated Antibodies The streptavidin-coupled nanoparticles are then coupled to a biotinylated antibody, specific for the substance to be assayed (insulin or thyroid stimulating hormone (TSH)), as shown schematically in FIG. 8.

The coupling protocol is as follows.

Between 10 and 50 µg/mL of biotinylated antibodies is brought into contact with the excess nanoparticles-SA for 1 h using a rotating wheel to promote diffusion and interaction between biotin and streptavidin. The concentration of antibodies is selected so as to have 3 antibodies per NP. Thus, it is certain that all antibodies will bind to the nanoparticles-SA and there is no need for a step to remove unbound antibodies. The concentration of antibodies is therefore three times higher than the concentration of nanoparticles.

Alternatively, it is also possible to directly couple antibodies to nanoparticles grafted with citrate ions. In this case, the same protocol as above should be used by replacing the streptavidin solution with an antibody solution.

1.4. Alternative Coupling Method by Direct Coupling of Nanoparticles with Antibodies According to an alternative method, the coupling of the nanoparticles with the non-biotinylated antibodies can be carried out directly by coupling the antibodies to nanoparticles functionalized with APTES (transformation of the amino groups into carboxyl groups, activation of the carboxyl groups and direct reaction with the amino groups on the surface of the antibodies), according to the following detailed protocol.

1.4.1. Coating Nanoparticles with a Silica Layer

After the synthesis of the nanoparticles in step 1.1, the nanoparticle solution is centrifuged at 17 000 g for 3 minutes to precipitate any nanoparticle aggregates and the supernatant is recovered. A size selection is made. To do this, several centrifugations at 1900 g for 3 min are carried out. Each centrifugation is followed by a redispersion of the nanoparticles in the sonicator, after which the size of the nanoparticles is determined using a DLS-Zeta Potential device (Zetasizer Nano ZS90, Malvern).

A volume of 25 mL of $Y_{0.6}Eu_{0.4}VO_4$ particles with a concentration of 20 mM vanadate ions is prepared. A volume of 2.5 mL of another pure sodium silicate solution (Merck Millipore 1.05621.2500) is added dropwise with a pipette to coat the surface of the particles. We let this solution work under stirring for at least 5 hours.

The solution is then purified to remove excess silicate and sodium counterions. The solution is centrifuged at 11 000 g (Sigma 3K10, Bioblock Scientific) for 60 minutes and then redispersed by sonication (Bioblock Scientific, Ultrasonic Processor, operating at 50% at 400 W). This step is repeated until the conductivity of the solution is below 100 µs/cm.

1.4.2. Grafting of Amines onto the Surface of Nanoparticles

In a 500 mL triple-neck round-bottom flask, place 225 mL of absolute ethanol and add 265 µL of 3-aminopropyltriethoxysilane (APTES) (Mw 221.37 g/mol Sigma Aldrich), which corresponds to a final concentration of 1.125 mM. This amount corresponds to 5 vanadate equivalents that are introduced. A refrigerant is then connected to the round-bottom flask. The assembly is then placed on a round-bottom flask heater and placed under a hood. The mixture is refluxed at 90° C. A colloidal solution of nanoparticles (vanadate ion concentration [V]=3 mM) in 75 mL water at pH 9 is added dropwise to one of the inlets of the triple-neck flask by means of a peristaltic pump at a flow rate of 1 mL/min. The assembly is heated under stirring for 24 h.

After 48 hours, we use a rotary evaporator (rotavapor R-100, BUCHI) to partially concentrate the nanoparticles. The solution is rotated in a suitable round-bottom flask and heated in a bath at 50° C.

The recovered solution is purified by several centrifugations in an ethanol:water (3:1) solvent. After purification, a size sorting is carried out following the protocol described above.

1.4.3 Grafting of Carboxyl to the Surface of Aminated Nanoparticles

Before starting the grafting, a solvent transfer is performed.

The grafting protocol is as follows.

Transfer the aminated NPs from EtOH:H$_2$O buffer to DMF or DMSO by performing several centrifugations (13 000 g, 90 min). The pellet is redispersed by sonication between each centrifugation (20 s at 75%). Measure and determine the concentration of NPs.

Recover the NPs in 5 mL of DMF and then add 10% of the succinic acid anhydride to a glass beaker (i.e. 0.5 g in the 5 mL). Allow to react at least overnight in an inert atmosphere while stirring.

Wash the carboxylated NPs at least twice by centrifugation (13 000 g for 60 min, Legend Micro 17R, Thermo Scientific) to remove DMF and excess succinic acid anhydride.

Resuspend the carboxylated particles in water or pH 6 MES buffer by sonication (Bioblock Scientific, Ultrasonic processor).

1.4.4 Direct Coupling of Nanoparticles with Antibodies

The coupling of the surface-grafted nanoparticles with COOH is carried out according to the protocol below:
 i) Freshly prepare a mixed solution of EDC/Sulfo-NHS (concentration 500 and 500 mg/mL, respectively) in MES buffer (pH 5-6).
 ii) In 3 mL of the previously prepared solution, add 90 nM NPs (in this case the nanoparticle concentration calculated from the vanadate ion concentration according to reference Casanova et al. [37]) and allow to react for 25 min at room temperature with stirring.
 iii) Quickly wash the NPs by at least 2 centrifugations (13 000 g for 60 min, Legend Micro 17R, Thermo Scientific) with Milli-Q water to remove excess reagents.
 iv) Recover the last pellet after sonication in sodium phosphate buffer at pH 7.3. Add the amount of antibody required according to the desired ratio (Protein:NPs), typically 2 µM for a ratio of 20:1.
 v) Allow this solution to react for 2 to 4 hours at room temperature while stirring.
 vi) Add the blocking agent (1% glycine) to react with the free COOHs and block the residual reaction sites on the surface of the NPs. Allow to react for 30 min.
 vii) Wash the protein-coupled NPs several times by centrifugation using centrifugal filters (Amicon Ultra 0.5 mL, item UFC501096, Millipore) with pH 7.2 PBS. Transfer the NPs to their storage medium: phosphate buffer+Tween 20 (0.05%)+0.1% glycine+10% glycerol. Collect 100 µL for BCA testing. The rest of the solution is aliquoted and frozen at −80° C.

The luminescent particles thus prepared according to either of the aforementioned methods, comprising photoluminescent nanoparticles $Y_{0.6}Eu_{0.4}VO_4$ coupled to a targeting antibody for the substance to be analyzed (NPs-Ab), can be used to detect and/or quantify said substance in a biological sample.

Example 2

Preparation of the Support on the Surface of which is Immobilized the Substance to be Analyzed i. Preparation of the Glass Slide Type Support In a first step, a support is prepared consisting of glass slides whose surface is previously cleaned, passivated and functionalized with biotinylated antibodies (capture antibodies).

The protocol for cleaning, passivation and functionalization of the glass slides is as follows. The functionalization can be done either by printing or by depositing drops using a spotter.

Cleaning the Slides
 Wash the slides in deionized water with 4% Hellmanex II detergent (Hellma) in an ultrasonic tank heated to 40-50° C. for 15 minutes.
 Rinse the slides with deionized water in an ultrasonic tank heated to 40-50° C. for 15 minutes.
 Rinse with absolute ethanol in an ultrasonic tank heated to 40-50° C. for 15 minutes.
 Dry in a stream of N$_2$ or under an extractor hood for 10-15 min.
 Just before the glass surface is functionalized, clean the slides one by one in a Plasma cleaner (Harrick Plasma, model PDC-002) for 2 minutes at medium intensity.

Passivation of the Slides

The passivation molecule used is a silane-polyethylene glycol (PEG) with 10 kDa PEG, marketed by Laysanbio under the item number M-SIL-5K.

Passivation only involves one stage of silanization of the glass. The longer the PEG, the better the resulting passivation will be.

The passivation protocol is as follows:
 Dissolve PEG at 10 mg/mL in absolute ethanol (EtOHAbs, molar concentration 2 mM or 1 mM depending on the size of the PEG respectively 5 kDa or 10 kDa). To dissolve the longer PEGs at 10 mg/mL, it may be necessary to heat them for a few minutes at 40° C.
 A few seconds before use, add in this solution a little H$_2$O and acetic acid (AcAc) to have the proportions v/v/v: EtOHAbs/H$_2$O/AcAc: 95/5/0.2.
 At the bottom of an airtight dish place a square of parafilm, then place a ~30 µL drop of the solution prepared above on top, then the glass slide (from the plasma cleaner) on top to take the drop as a sandwich. Put a small reservoir of ethanol in the hermetically sealed dish to saturate the air with ethanol and so that the 30 µL does not dry out. Allow to incubate overnight.
 Rinse with deionized water, then dry in a stream of nitrogen. Finally, place the strips on a hot plate at 110° C. for 5 min.

Functionalization of the Slides by Overnight Incubation

The protocol for functionalizing the slides previously passivated with biotinylated antibodies is as follows. This is the protocol used for the results shown in the figures.

Incubation of the slide in a solution containing the capture antibodies overnight at 4° C. The antibody solution contains 10-25 µg/mL antibodies in a solution of PBS at pH 7.4 or carbonate buffer at pH 9 according to the supplier's instructions.

Alternatively, the following two protocols can be used:

Functionalization by Streptavidin Printing and Biotinylated Antibodies

Cut a patch of PDMS (polydimethylsiloxane) with dimensions corresponding to the surface that is to be functionalized.

Place the patch on a flat surface. Incubate on the patch ~15-30 µL of streptavidin at 20 µg/mL in phosphate-buffered saline (PBS) for 1 min.

Rinse immediately with $H_2O$ (using a wash bottle) and pass under a stream of $N_2$ (10 sec).

Turn the patch over and place its inked surface on the slide for 1 min.

Remove the patch, being careful not to drag it across the surface.

After functionalization of the glass slide with streptavidin, incubate the necessary amount (1-10 µg/mL in bicarbonate buffer pH 7.4) of biotinylated antibodies for 2 h at room temperature or overnight at 4° C.

Remove the antibody incubation solution and wash with 100 µL of PBS buffer 3 times.

Add 100 µL of BSA 5% w/v (5 g in 100 mL) PBS and incubate for 1 h.

Functionality by Spotter

Spotter functionalization is performed with the SPRi-Arrayer device from Horiba according to the supplier's protocol using a 500 µm diameter needle to deposit drops containing the antibodies (1-10 µg/mL in bicarbonate buffer pH 7.4).

ii. Immobilization of the Substance to be Analyzed of the Samples on the Surface of the Support The protocol is as follows.

Add the samples to be assayed (insulin solution, insulin in serum or TSH solution) to each well and incubate for 2 hours. This time is the same as that indicated for the corresponding conventional ELISAs.

After 2 hours incubation, remove the solution and wash with 100 µL wash buffer (0.2% PBS 2× Tween 20) 3 times.

Example 3

Ultrasensitive Detection and Quantification 3.1. Association of Luminescent Particles with the Substance to be Analyzed The protocol is as follows:

Add the nanoparticles coupled to the biotinylated antibodies prepared as described in Example 1 and incubate for 1 hour. The incubation time required to maximize the signal during luminescence measurement can be determined beforehand, as described in Example 4.

After 1 hour incubation, remove the solution and wash with 100 µL wash Buffer (0.2% PBS 2× Tween 20) 4 times.

Add 100 µL of PBS and perform the luminescence measurement as described below.

3.2 Luminescence Measurement i. Experimental Arrangement for Measuring Luminescence The detection arrangement is as follows. It is shown schematically in FIG. 2 and FIGS. 12 and 13.

The detection device consists of a 1 W laser source (1) with a wavelength of 465 nm (ML-6500-465, Modulight or F465-HS-1W, Laser2000), a collimation and laser beam size reduction system (2) consisting of two lenses (two Ø½" bi-convex lenses of f=100 mm and f=30 mm (Thorlabs)), optionally a mechanical chopper (4) (MC2000B-EC, Thorlabs), a slide support (6) for the samples, and a detection system for the emitted photons.

To collect the luminescence emission by the nanoparticles in the sample, a high numerical aperture lens (10) (bi-convex lens, Ø=50.8 mm, f=100 mm (Thorlabs)) and two interference filters 620±14-25 (FF01-620/14-25, Semrock) to spectrally eliminate interfering signals and a photomultiplier (12) (PMM02, Thorlabs) are used.

An analog-to-digital converter (NI9215, National Instrument) allows the signal to be recorded using LabVIEW software.

All detection elements are located on the same axis. Thus, the arrangement is both more ergonomic and easier to adjust. A translation system of the slide support (Z8253, KCH301 Thorlabs) was implemented in order to be able to observe several biological samples successively by scanning.

Time-Resolved Detection for Measuring the Number of Nanoparticles in the Presence of Interfering Signals A mechanical chopper can be placed in the path of the laser beam to create laser excitation slots to eliminate interfering signals. Indeed, during the illumination of the biological sample by the laser beam, it is possible that molecules other than the nanoparticles of interest emit fluorescence. The use of a mechanical chopper and a signal detection frequency of 100 kHz by the photomultiplier (signal acquisition every 10 µs) makes it possible to avoid this interfering fluorescence.

It is thus possible due to the long emission time by the particles of the invention, to make a time-resolved detection of the emission, in particular a delayed detection of the emission, as described in detail below.

A time-modulated illumination allows to limit the contribution to the luminescence signal of interfering species present in the sample (serum, blood, etc.) or in the solid substrates used (glass, plastic, etc.). Indeed, the nanoparticles used ($YVO_4$:Eu or $GdVO_4$:Eu for example) can be placed (by illumination at 465 nm) in an excited state with a long lifetime, of the order of a few hundred µs, in comparison with the lifetime of usual fluorophores, which are in the nanosecond range. This allows the temporal separation of the interfering luminescence signals from the signal emitted by the nanoparticles.

The modulation can be implemented by the use of a rotating mechanical chopper, in order to obtain periodic illumination at frequencies between 100 and 1000 Hz. FIG. 9 schematically shows the illumination time profile obtained by mechanical chopping of the excitation laser.

The modulated signal obtained is the alternation of a decay phase (chopper closing) and a luminescence return phase (chopper opening) of all the emitters present in the sample. The decay/return of the luminescence signal is determined by two separate parameters: (i) the lifetimes of the excited states of the emitters, and (ii) the dynamics of occultation/uncovering of the exciter beam by the mechanical chopper. FIG. 10-*a* shows examples of luminescence decline after initiation of chopper closure (t=0). Digital post-processing analysis of the signal allows the signal due to nanoparticles to be isolated, for example by the following two methods.

Method 1: Delayed Detection.

In the phase of luminescence decay, the contribution of the interfering emitters is concentrated at short times, when the excitation beam is not yet fully occluded (FIG. 10-*a*). By removing this part (FIG. 10-*b*, detection restricted to 170 µs after the beginning of the occultation of the excitation beam by the chopper blade), a signal due exclusively to nanoparticles is obtained (superposition of curves (b) and (c), the contribution of the interfering fluorescence of the slide, serum and water is eliminated), which thus allows an estimation of their number despite the presence of other emitters.

Method 2: Time-Resolved Detection

The luminescence of nanoparticles and interfering fluorophores can be modelled by a two-level system (FIG. 11). In this case, the shape of the luminescence signal PL(t) can be determined from the characteristics of the transmitters:

$$PL(t) = k\varphi N^* = G[I(t), k, N, \varphi]$$

where I(t) is the excitation time profile; N is the total number of emitters of a type and N* is the number of emitters on the excited state; k its de-excitation rate; $\varphi$ its quantum efficiency; by numerically solving the system of differential equations resulting from the model.

The total signal can then be written, $$PL(t) = G[I(t), k_{NP}, N_{NP}, \varphi_{NP}] + F[I(t), k_F, N_F, \varphi_F] + BG$$

where NP and F denote nanoparticles and interfering fluorophores, respectively, and BG denotes the background signal.

Adjustment of the signal recorded by this function then makes it possible to determine the various parameters, notably $N_{NP}$ and $k_{NP}$ (FIG. 11). It is robust, as $k_{NP} \ll k_F$. The determination of the number of nanoparticles adhering to the $N_{NP}$ surface is then carried out unambiguously, despite the presence of interfering emitters in the sample contributing to the raw signal. In practice, the mechanical masking kinetics of illumination at the frequencies used (100-1000 Hz) is significantly slower than the fluorescence decay of interfering emitters $k_F \sim 10^9$ s$^{-1}$, so that F [I(t), $k_F$, $N_F$, $\varphi_F$]~K·I(t).

The measurement of $N_{NP}$ is then carried out by the following method: (i) experimental determination of the illumination time profile I(t)/I(0) by measuring the autofluorescence of a calibration sample without nanoparticles; (ii) measurement of the luminescence signal of the target sample; and (iii) non-linear adjustment (least squares method) of this signal by a function $$PL(t) = M \cdot \frac{I(t)}{I(0)} + G[I(t), k_{NP}, N_{NP}, \varphi_{NP}] + BG.$$

This adjustment allows the identification of the parameters M, $k_{NP}$ and $\varphi_{NP}N_{NP}$ to within an instrumental multiplicative factor: this last parameter then indicates, for fixed detection conditions, the number of nanoparticles deposited on the surface.

Variants of the Experimental Arrangement

The nanoparticles are excited:
either by using a high angle of incidence (angle between the direction of propagation of the laser beam and the vertical to the sample support) between 60° and 63° (as shown schematically in FIG. 12),
or by using a total internal reflection fluorescence (TIRF) type illumination arrangement, in particular using a Plexiglas 13 parallelepiped with a refractive index greater than or equal to that of the glass slide serving as sample support (as shown schematically in FIG. 13). This configuration provides an angle of incidence at the glass/water or glass/serum interface greater than 61.04°, resulting in total reflection of the beam at this interface and evanescent wave excitation of the nanoparticles anchored to the substance to be analyzed.

Three variants of the experimental arrangement were used.

Variant 1: Reflected (downward) detection without chopper (except where specified) and without evanescent wave excitation (FIG. 12-a). In the majority of cases, the acquisition time is fixed at 30 s with a voltage value recorded every 100 ms. The diameter of the collection lens is 30 mm instead of 50.8 mm.

Variant 2: Transmission detection (upwards) (FIG. 12-b). Measurements can be made with or without a chopper and with or without evanescent wave excitation. The acquisition time is fixed at 1 s with a voltage value recorded every 10 µs. This variant includes the blade support translation system (Z8253, KCH301 Thorlabs).

Variant 3: Transportable mounting with transmission detection (downwards). Measurements can be made with or without a chopper and with or without evanescent wave excitation. The acquisition time is fixed at 1 s with a voltage value recorded every 10 µs.

For each sample concentration to be detected, several measurements (N measurements, N greater than or equal to 5) at different positions of the slide are performed. Each measurement is the average of 100 000 values recorded for 1 s with an acquisition rate of 100 kHz (1 voltage value recorded every 10 µs) except in the case of variant 1 of the experimental arrangement where the acquisition time was 30 s with a voltage value recorded every 100 ms.

The signal value indicated on the graphs and its error bar correspond, respectively, to the mean of the N measurements and their standard deviation. In most cases, the signal value for a concentration of the molecule to be detected equal to zero was subtracted from all the measured values for the different concentrations. Thus the signal value for a concentration equal to zero, appears at zero. However, the standard deviation indicated is a measure of the ability to detect a given concentration. Typically, the detection limit is considered to be determined by the concentration generating a signal equal to 3 times the standard deviation of the signal obtained at zero concentration ("blank"). The limit of quantification is determined by the concentration generating a signal 10 times greater than this standard deviation at zero concentration.

For experiments performed with evanescent wave excitation, a collection of the luminescence from above is preferable. Indeed, the luminescence emission by the sample downwards is refracted towards wide angles by the Plexiglas parallelepiped and, as a result, a smaller fraction is collected by the collection lens in the presence of the parallelepiped allowing the evanescent wave excitation to take place.

ii. Calibration of the Detection Device

Prior to the measurements, the detection device was calibrated with nanoparticles in solution, according to variants 2 (upward detection with chopper and with evanescent wave excitation) and 3 (downward detection, without chopper and without evanescent wave excitation).

The calibration protocol is as follows:
The glass slides are activated beforehand with the plasma cleaner.
deposition of a solution of nanoparticles diluted in PBS of known concentration on the glass slide;
incubation for 2 hours;
rinse at least three times with ultrapure water.
The acquisition time is fixed at 1 s with a voltage value recorded every 10 µs.

The calibration curves of the detection device obtained from the two variants are shown in FIGS. 14-a and 14-b.

iii. Results of Detection/Quantification Tests
Detection and Quantification of a Substance in a Sample The concentration of a substance in a sample is detectable when the signal obtained is at least three times greater than the standard deviation of the signal for a sample of the same composition containing zero concentration of the substance.

In order to carry out the quantification of the substance to be analyzed (i.e. to determine its concentration), the following protocol must be implemented:
  i) perform a series of calibration measurements with the substance to be analyzed at different known concentrations, for example from commercially available substances or from purification. If possible, calibration samples should be prepared with the same or as close as possible to the composition of the samples to be measured. Make an adjustment of the points obtained (signal in mV versus concentration of the substance to be analyzed);
  ii) carry out measurements of the samples to be analyzed (obtaining the signal value in mV);
  iii) assign to each measured sample a concentration value of the substance from the measured signal (in mV) and from the calibration curve carried out in step i) and its fit.

The concentration of a substance in a sample is quantifiable when the signal obtained is at least 10 times greater than the standard deviation of the signal for a sample of the same composition containing zero concentration of the substance.

Detection of Insulin

The samples analyzed are either solutions of recombinant insulin in PBS+5% BSA or insulin in serum (samples provided by Cerba Specimen Services with insulin concentrations previously determined by reference techniques).

For recombinant insulin samples in solution in PBS+5% BSA, the recombinant insulin provided by the ELISA kit for the associated calibration experiments was used. The various samples were prepared by successive dilutions according to the protocol indicated by the kit supplier.

For serum insulin samples, the solutions were used as is for the highest concentrations. As very low concentration samples were not available, they were prepared by diluting the samples containing the lowest available concentrations in PBS+5% BSA.

Detection by ELISA

For comparison, the detection of recombinant insulin was carried out in solution by an ELISA kit in a 96-well plate. The experimental conditions followed are those indicated by the ELISA kit supplier. The absorbance of the well that was not incubated with insulin (zero concentration) was subtracted from the absorbance values measured for the wells that were incubated with the different insulin concentrations. Two wells were used for each concentration value and the standard deviation for these two measurements is shown as the error bar in FIG. 15. The lowest concentration measured is 187 pg/mL (or 33 pM). The standard deviation for zero concentration is 0.0035. The measured absorbance value for the concentration 187 pg/mL (or 33 pM) is 0.0085, just below the limit value of 0.0105 equal to 3 times the standard deviation determined for zero concentration. According to the supplier's specifications (ABCAM item ab100578), detection by a conventional ELISA kit will not detect concentrations below 50 pg/mL (or 9 pM) (FIG. 15).

Ultrasensitive Detection According to the Invention

FIG. 16 shows the signal obtained for samples of recombinant insulin in solution for different concentrations, with the lowest concentration being 0.05 pg/mL (or 9 fM), with variant 1 of the detection device. The acquisition time is 30 seconds, with a voltage value recorded every 100 ms.

In the inset in FIG. 16, the signal without insulin has been subtracted.

The minimum detectable concentration is thus 1000 times lower than the concentration detectable by ELISA (50 pg/mL or 9 pM) using the same antibodies as the ELISA kit.

FIG. 17 shows the signal obtained for samples of recombinant insulin in solution for different concentrations, with the lowest concentration being 0.05 pg/mL (or 9 fM), with variant 2 of the detection device (top detection), without chopper and without evanescent wave excitation. The acquisition time is 1 second, with a voltage value recorded every 10 µs.

The minimum concentration detected is thus 1000 times lower than the concentration detectable by ELISA (50 pg/mL or 9 pM) using the same antibodies as the ELISA kit.

FIG. 18 shows the signal obtained for samples of recombinant insulin in solution for different concentrations, with the lowest concentration being 0.05 pg/mL (or 9 fM), with variant 2 of the detection device (top detection), with chopper and with evanescent wave excitation. The acquisition time is 1 second, with a voltage value recorded every 10 µs.

The minimum concentration detected is thus 1000 times lower than the concentration detectable by ELISA (50 pg/mL or 9 pM) using the same antibodies as the ELISA kit.

FIG. 19 shows the signal obtained for serum samples containing insulin (samples provided by CERBA Specimen Services and diluted in PBS+5% BSA for the lowest concentrations. To obtain the lowest concentration samples, the sample containing insulin at approximately 8 pM was diluted on an IBIDI multiwell plate with variant 1 of the detection device.

The acquisition time is 30 seconds, with a voltage value recorded every 100 ms.

The minimum concentration detected is 9 fM (or 0.05 pg/mL), 1000 times lower than the concentration detectable by ELISA (50 pg/mL or 9 pM) using the same antibodies as the ELISA kit.

TSH Detection

The samples analyzed are solutions of recombinant TSH with a molecular weight of 15 639 Da in PBS+5% BSA. The antibodies used are those of the ABCAM kit item ab 100660.

Ultrasensitive Detection According to the Invention

FIG. 20 shows the signal obtained for recombinant TSH samples in solution for different concentrations, with the lowest concentration being 3.2 fM (1.4 fg/mL), using variant 1 of the detection device with chopper. The acquisition time is 1 second, with a voltage value recorded every 10 µs.

In comparison, the minimum concentration that can be detected by the ELISA kit is typically less than 4 pg/mL according to the supplier. Thus, the minimum concentration detected according to the invention is more than 1000 times lower than the concentration detectable by the ELISA kit.

Example 4

Incubation Time Adjustment

The incubation time required to maximize the signal in the case of the detection of recombinant insulin in solution (50 pg/mL insulin) can be determined beforehand by luminescence measurements obtained for different incubation times between sample supports with the substance to be analyzed (here recombinant insulin) immobilized on their surfaces (immobilization carried out according to the protocol described in Example 2ii) and antibody-nanoparticle conjugates (obtained according to the protocol described in Example 1 with 10 µg/mL antibody), step carried out according to the protocol described in Example 3.i.

The measurements were made with variant 1 of the detection device described in Example 3. The acquisition time is 30 seconds, with a voltage value recorded every 100 ms.

FIG. 21 shows the change in the detected luminescence signal as a function of the incubation time.

It appears necessary to incubate the antibody-coupled nanoparticles with the surface on which the substance to be analyzed (in this case recombinant insulin) is immobilized for at least 45 minutes to maximize the detected luminescence signal. This time required may vary depending on the substance to be analyzed and the antibody used.

Example 5

Spatial Multiplexing Experiment

To illustrate the possibility of performing "multiplexed" detection according to the process of the invention (schematic diagram of spatial multiplexing shown in FIG. 22), the following experiment was performed.

Two areas or "spots" containing nanoparticles were created by depositing two drops of two solutions of nanoparticles as obtained according to the protocol described in Example 1 (part 1.1, nanoparticles as obtained after synthesis) of two different concentrations (4 mM and 8 mM) on glass slides cleaned according to the protocol described in Example 2. Here the drops containing the nanoparticles were allowed to dry before the luminescence measurements began, without a rinsing step.

The diagram in FIG. 23 shows the diameter of the laser beam at the sample level according to the direction of travel (3 mm), the diameter (2 mm) and the distance between the two nanoparticle "spots" (1 mm).

The measurements are carried out with variant 2 of the experimental arrangement described in Example 3 (upward detection, with chopper and without evanescent wave excitation). Thanks to the motorized displacement system of the sample support, the signal emitted by the nanoparticles was detected at several locations: before the first "spot" (position 1), in the first "spot" (position 4), between the two "spots" (position 6), in the second "spot" (position 7) and finally after the second "spot" (position 9). For each position of the excitation laser beam, the acquisition time is 1 second, with a voltage value recorded every 10 µs.

FIG. 23 shows the luminescence signal detected for the different locations mentioned above. The two peaks with different locations and amplitudes show the possibility of differentiating spatially organized deposits, as is necessary for a multiplexed measurement.

Example 6

Synthesis of 3% $YVO_4$:Dy Nanoparticles.

The protocol used is even the same as that for the synthesis of the $Y_{0.6}Eu_{0.4}VO_4$ nanoparticles indicated in point 1.1. of Example 1 above, with the only difference being that instead of the precursor $Eu(NO_3)_3$, we use the precursor $Dy(NO_3)_3$ at a concentration of 0.03 M.
Result FIG. 26 shows the luminescence excitation and emission spectra of a solution of these nanoparticles after their synthesis. The excitation spectrum shows peaks of direct excitation of $Dy^{3+}$ ions. The following steps of functionalization and coupling to streptavidin (Example 1, point 1.2.) and then to a biotinylated targeting agent (Example 1, point 1.3.), or direct coupling to a targeting agent (Example 1, point 1.4.), can be reproduced identically with these nanoparticles, thus producing probes emitting at a different emission wavelength.

Example 7

Synthesis of 3% $YVO_4$:Sm Nanoparticles.

The protocol used is even the same as that for the synthesis of the $Y_{0.6}Eu_{0.4}VO_4$ nanoparticles indicated in point 1.1. of Example 1 above, with the only difference being that instead of the precursor $Eu(NO_3)_3$, we use the precursor $Sm(NO_3)_3$ at a concentration of 0.03 M.
Result FIG. 27 shows the luminescence excitation and emission spectra of a solution of these nanoparticles after their synthesis. The excitation spectrum shows peaks of direct excitation of $Sm^{3+}$ ions. The following steps of functionalization and coupling to streptavidin (Example 1, point 1.2.) and then to a biotinylated targeting agent (Example 1, point 1.3.), or direct coupling to a targeting agent (Example 1, point 1.4.), can be reproduced identically with these nanoparticles, thus producing probes emitting at a different emission wavelength.

REFERENCES

[1] Hermanson, *Bioconjugate Techniques*, Academic Press, 1996;
[2] Mason, *Fluorescent and Luminescent Probes for Biological Activity. A Practical Guide to Technology for Quantitative Real-Time Analysis*, Second Edition, Academic Press, 1999;
[3] Medintz et al., Nat. Mat., 2005, 4, pp. 435-446;
[4] Nam et al., Science, 2003, 301, pp. 1884-1886;
[5] H. Li et al., Analyst, 2011, 136, pp. 1399-1405;
[6] Z. Cao et al., Anal. Chim. Acta, 2011, 698, pp. 44-50;
[7] Pisanic et al., Analyst, 2014, 139(12), pp. 2968-2981;
[8] Geissler et al., Angewandte Chemie International Edition, 2010, 49(8), pp. 1396-1401;
[9] Howes et al., Bionanotechnology, 2014, 346(6205), pp. 53-63;
[10] Giljohann et al., Angewandte Chem, 2010, 49, pp. 3280-3294;
[11] De La Rica et al., Nature Nanotechnology, 2012, 7, pp. 821-824;
[12] Zhu et al., Anal. Chem., 2013, 85(2), pp 1058-1064;
[13] Cordeiro et al., Diagnostics, 2016, 6(4):43;
[14] Riwotzki et al., J. Phys. Chem. B, 1998, 105, pp. 12709-127;
[15] Huignard et al., Chem. Mater., 2000, 12, pp. 1090-1094;
[16] Bouzigues et al., ACS Nano, 2011, 5(11) pp. 8488-8505;
[17] Dosev et al., J. Biomed. Opt., 2005, 10(6), 064003;
[18] Yi et al., Nano Letters, 2004, 4(11), pp. 2191-2196;
[19] Beaurepaire et al., Nano Letters, 2004, 4(11), pp. 2079-2083;
[20] Turkcan et al., Biophysical Journal, 2012, 102, pp. 2299-2308;
[21] Yuan et al., Trends in Analytical Chemistry, 2006, 25(5), pp. 490-500;
[22] Tang et al., Clin Vaccine Immunol, 2009, 16(3), pp. 408-413;

[23] Härmä et al., 2001, Clinical Chemistry, 47(3), pp. 561-568;
[24] Corstjens et al., Clinical Biochemistry, 2008, 41(6) pp. 440-444;
[25] Hemmilä et al., Analytical Biochemistry, 1984, 137(2), pp. 335-343;
[26] Jiang et al., Journal of Fluorescence, 2010, 20(1), pp 321-328;
[27] Tanja et al., Analytical and Bioanalytical Chemistry, 2004, 380(1), pp 24-30;
[28] Zhou et al., Angewandte Chimie, 2014, 126(46), pp. 12706-12710;
[29] Riwotzki et al. J. Phys. Chem. B, 1998, 102, 10129;
[30] Meza et al. J. Phys. Chem. A, 2014, 118, 1390;
[31] Dordevic et al. J. Res. Phys., 2013, 37, 47;
[32] Casanova et al., J. Am. Chem. Soc., 2007, 129, 12592;
[33] Giaume et al., Langmuir, 2008, 24, pp. 11018-11026;
[34] Abdesselem et al., ACS Nano, 2014, 8(11), pp. 11126-11137;
[35] Casanova et al., Appl. Phys. Lett, 2006, 89, 253103;
[36] Son et al., Journal of Nanoscience and Nanotechnology, vol. 8, 2463-2467, 2008;
[37] Nichkova et al., Anal. Chem. 2005, 77, 6864-6873.

The invention claimed is:

1. A process for the ultrasensitive in vitro detection and/or quantification of a target substance of biological or chemical interest by detecting luminescence emission by photoluminescent inorganic nanoparticles, comprising at least the following steps:
    providing a sample having the target substance in an amount below 10 pM;
    immobilizing the target substance to a functionalized surface;
    providing photoluminescent particles to the immobilized target substance on the functionalized support to associate with the target substance, the photoluminescent particles consisting, in whole or in part, of a photoluminescent inorganic nanoparticle consisting of a crystalline matrix having at least $10^3$ rare-earth ions, and coupled to at least one targeting agent for the target substance to be analyzed, under conditions conducive to their association with the target substance to be analyzed of the sample, said nanoparticles having an average size greater than or equal to 20 nm and strictly less than 1 μm, and being capable of emitting luminescence after absorption of a photon;
wherein the nanoparticle is of the following formula (I):

$$(A_{1-x}Ln_x)_a(M_pO_q) \quad (I)$$

wherein:
    M represents one or more elements capable of associating with oxygen (O) to form a crystalline compound;
    Ln corresponds to one or more luminescent lanthanide ion(s);
    A corresponds to one or more constituent ion(s) of the crystalline matrix whose electronic levels are not involved in the luminescence process;
    $0 < x < 1$; and
        the values of p, q and a are such that the electroneutrality of $(A_{1-x}Ln_x)_a(M_pO_q)$ is respected;
        illuminating of the rare-earth ions of the photoluminescent particles associated with the target substance, by an illumination device, with a power of at least 50 mW, and an excitation intensity of at least 1 W/cm²;
        detecting luminescence emitted by the photoluminescent particles after single-photon absorption, and
        determining of the presence and/or concentration of the substance by interpretation of said luminescence measurement, where appropriate by reference to a standard or calibration, wherein the target substance is determined to be present in the sample in an amount below 10 pM;
    said process providing detection and/or quantification of a substance of interest present in a sample in a content strictly below 10 pM; and
    the process using a light intensity 2D detection device comprising a single detector allowing simultaneous measurement of the emission signal of nanoparticles from different areas corresponding to different target substances to be analyzed on the surface of the functionalized support and does not require any movement of the support or the excitation beam.

2. The process as claimed in claim 1, wherein the substance to be analyzed of said sample is previously immobilized on the surface of a support, said surface being passivated so that said luminescent particles do not attach thereto in the absence of the substance to be analyzed.

3. The process as claimed in claim 1, wherein the sample is a biological sample.

4. The process as claimed in claim 1, for the detection and/or quantification of biomarkers, antibodies, DNA and/or RNA in a biological sample.

5. The process as claimed in claim 1, wherein said targeting agent is selected from a polyclonal or monoclonal antibody, an antibody fragment, a nanobody, an oligonucleotide, a peptide, a hormone, a ligand, a cytokine, a peptidomimetic, a protein, a carbohydrate, a chemically modified protein, a chemically modified nucleic acid, a chemically modified carbohydrate which targets a known cell surface protein, an aptamer, a protein and DNA/RNA assembly or a chloroalkane.

6. The process as claimed in claim 1, wherein the product between the doping rate of rare-earth ions and the quantum efficiency of the emission from the nanoparticle is maximized.

7. The process as claimed in claim 1, wherein the nanoparticles have an emission lifetime greater than or equal to 5 μs.

8. The process as claimed in claim 1, wherein the nanoparticles have an average size of between 20 nm and 500 nm.

9. The process as claimed in claim 1, wherein the lanthanide ions are selected from europium (Eu), dysprosium (Dy), samarium (Sm), praseodymium (Pr), neodymium (Nd), erbium (Er), ytterbium (Yb), cerium (Ce), holmium (Ho), terbium (Tb), thulium (Tm) and mixtures thereof.

10. The process as claimed in claim 1, the nanoparticles being of formula:

$$A_{1-x}Ln_xVO_{4(1-y)}(PO_4)_y \quad (II)$$

wherein:
    A is selected from yttrium (Y), gadolinium (Gd), lanthanum (La), lutetium (Lu) and mixtures thereof;
    Ln is selected from europium (Eu), dysprosium (Dy), samarium (Sm), neodymium (Nd), erbium (Er), ytterbium (Yb), thulium (Tm), terbium (Tb) and mixtures thereof;
    $0 < x < 1$; and
    $0 \leq y < 1$.

11. The process as claimed in claim 10, wherein said nanoparticles of formula (II) have on their surface tetraalkylammonium cations.

12. The process as claimed in claim 11, said nanoparticles being of formula (II')

   (II')

wherein:
- A is selected from yttrium (Y), gadolinium (Gd), lanthanum (La), lutetium (Lu) and mixtures thereof;
- Ln is selected from europium (Eu), dysprosium (Dy), samarium (Sm), neodymium (Nd), erbium (Er), ytterbium (Yb), thulium (Tm), terbium (Tb) and mixtures thereof;
- $0<x<1$;
- $0 \leq y < 10$;
- R, which may be identical or different, represent a $C_1$-$C_6$-alkyl; and
- z represents the number of tetraalkylammonium cations $NR_4^+$ located on the surface of said nanoparticle.

13. The process as claimed in claim 1, wherein said nanoparticles are of formula $Y_{1-x}Eu_xVO_4$, wherein $0<x<1$.

14. The process as claimed in claim 1, wherein the nanoparticles have, at the end of their synthesis, a zeta potential, denoted ζ, less than or equal to −28 mV, in aqueous medium of pH≥5, and of ionic conductivity strictly less than 100 μS·cm$^{-1}$.

15. The process as claimed in claim 2, further comprising at least the following steps:
(a) providing a support whose surface is previously passivated and functionalized with a targeting agent for the substance to be detected/quantified;
(b) contacting said sample to be analyzed with the support of step (a) under conditions conducive to the association of said substance with the targeting agent; and
(c) contacting the photoluminescent particles coupled with at least one targeting agent with said support from step (b) to associate the particles with said substance immobilized on the surface of the support.

16. The process as claimed in claim 2, wherein said support is of the slide, multiwell plate, microplate, membrane gel, strip or microchannel type.

17. The process as claimed in claim 2, wherein the excitation is carried out with a laser excitation beam oriented so as to form an angle of incidence greater than or equal to 55° with the vertical of the support having at the surface said particles associated with the substance to be analyzed.

18. The process as claimed in claim 2, comprising the excitation of the particles by evanescent wave.

19. The process as claimed in claim 1, wherein the lifetime of emission by the nanoparticles is greater than or equal to 1 μs, the detection of the light intensity comprising a time-resolved detection of the emission.

20. The process as claimed in claim 1, for the simultaneous detection and/or quantification of at least two different substances in a sample.

21. The process as claimed in claim 20, wherein the substances to be analyzed of said sample are immobilized in predefined and distinct areas on the surface of a support, said surface being passivated so that photoluminescent particles do not bind to it in the absence of the substances to be analyzed.

22. The process as claimed in claim 20, using at least two types of nanoparticles having distinct emission wavelengths and coupled to targeting agents for each of the substances to be analyzed.

23. The process as claimed in claim 1, wherein the laser illumination device comprises an optical arrangement, arranged in the path of the laser beam so as to control the size of the beam at the area of the support having the particles associated with the substance to be analyzed.

24. The process as claimed in claim 1, wherein the detection device comprises an optical arrangement, for focusing the luminescence emission to the detector.

25. The process as claimed in claim 1, wherein the sample is provided with the target substance in an amount below 1 pM, and the target substance is determined to be present in the sample in an amount below 1 pM.

26. The process as claimed in claim 1, wherein the sample is provided with the target substance in an amount below 0.1 pM, and the target substance is determined to be present in the sample in an amount below 0.1 pM.

27. The process as claimed in claim 1, wherein the sample is provided with the target substance in an amount below 0.01 pM, and the target substance is determined to be present in the sample in an amount below 0.01 pM.

* * * * *